(12) United States Patent
Imahashi et al.

(10) Patent No.: US 8,394,392 B2
(45) Date of Patent: Mar. 12, 2013

(54) ANTIBACTERIAL AGENT COMPOSED OF SILVER-CONTAINING ALUMINUM SULFATE HYDROXIDE PARTICLES AND USE THEREOF

(75) Inventors: Takeshi Imahashi, Sakaide (JP); Xing Dong Wang, Sakaide (JP); Akira Okada, Sakaide (JP); Yoshie Inoue, Sakaide (JP)

(73) Assignee: Kyowa Chemical Industry Co., Ltd., Kagawa (JP)

( * ) Notice: Subject to any disclaimer, the term of this patent is extended or adjusted under 35 U.S.C. 154(b) by 1444 days.

(21) Appl. No.: 11/988,009

(22) PCT Filed: Jun. 30, 2006

(86) PCT No.: PCT/JP2006/313527
§ 371 (c)(1),
(2), (4) Date: Dec. 28, 2007

(87) PCT Pub. No.: WO2007/004713
PCT Pub. Date: Jan. 11, 2007

(65) Prior Publication Data
US 2009/0047311 A1    Feb. 19, 2009

(30) Foreign Application Priority Data

Jun. 30, 2005 (JP) .................. 2005-192471
Jul. 1, 2005 (JP) .................. 2005-194071

(51) Int. Cl.
*A61K 9/00*    (2006.01)
(52) U.S. Cl. ................................... 424/400
(58) Field of Classification Search .............. 424/400
See application file for complete search history.

(56) References Cited

U.S. PATENT DOCUMENTS

| | | | |
|---|---|---|---|
| 2,584,041 A * | 1/1952 | Nowak et al. | 530/230 |
| 3,856,805 A * | 12/1974 | Margraf | 548/109 |
| 3,896,138 A * | 7/1975 | Kreider | 252/301.35 |
| 4,533,435 A * | 8/1985 | Intili | 162/161 |
| 4,626,567 A * | 12/1986 | Chang | 524/493 |
| 5,094,847 A * | 3/1992 | Yazaki et al. | 424/618 |
| 5,807,641 A * | 9/1998 | Oku et al. | 428/701 |
| 6,344,218 B1 * | 2/2002 | Dodd et al. | 424/605 |
| 6,436,422 B1 * | 8/2002 | Trogolo et al. | 424/405 |
| 6,723,428 B1 * | 4/2004 | Foss et al. | 428/370 |
| 2003/0004065 A1 * | 1/2003 | Belmonte | 504/152 |
| 2003/0168127 A1 * | 9/2003 | Hamamura et al. | 148/248 |
| 2004/0053048 A1 * | 3/2004 | Guevel et al. | 428/373 |

FOREIGN PATENT DOCUMENTS

| | | |
|---|---|---|
| JP | 5-57002 | 3/1993 |
| JP | 5-221638 | 8/1993 |
| JP | 6-212019 | 8/1994 |
| JP | 10-273324 | 10/1998 |
| JP | 2000-7326 | 1/2000 |
| JP | 2000007326 | * 1/2000 |
| JP | 2005-111733 | 4/2005 |
| WO | 2005/085168 | 9/2005 |
| WO | 2006/109847 | 10/2006 |

OTHER PUBLICATIONS

Coulter. Comparison of Sizing Results Obtained From Electrical Sensing Zone and Laser Diffraction Methods, Beckman Coulter, 2006.*
Zhao and Stevens. Biometals. Jan. 1998;11(1):27-32.*
Huang J, Aoyama K, Ueda A, Matsushita T. Bull Environ Contam Toxicol. Aug. 1995;55(2):320-4.*
Chapman J. International Biodeterioration & Biodegradation 41(1998) 241-245.*
JP 10-273324 machine translation.*

* cited by examiner

*Primary Examiner* — David J Blanchard
*Assistant Examiner* — Devang Thakor
(74) *Attorney, Agent, or Firm* — Wenderoth, Lind & Ponack, L.L.P.

(57) ABSTRACT

An antibacterial agent composed of silver-containing aluminum sulfate hydroxide particles represented by the following formula (X-I) or (Y-I).

$$(Ag_aB_{b-a})_bAl_cA_x(SO_4)_y(OH)_z \cdot pH_2O \quad \text{(X-I)}$$

$$[Ag_aB_{b-a}]_b[Ti_{3-c}Al_c](SO_4)_y(OH)_z \cdot pH_2O \quad \text{(Y-I)}$$

The above antibacterial agent of the present invention provides antibacterial molded articles and further antifungal agents, cosmetics, antibacterial paper, antibacterial deodorizing sprays and agricultural chemicals when it is mixed with a resin.

30 Claims, 11 Drawing Sheets

2um

1um

2um

2um

ANTIBACTERIAL AGENT COMPOSED OF SILVER-CONTAINING ALUMINUM SULFATE HYDROXIDE PARTICLES AND USE THEREOF

FIELD OF THE INVENTION

The present invention relates to an antibacterial agent composed of silver-containing aluminum sulfate hydroxide particles. More specifically, it relates to an antibacterial agent composed of silver-containing aluminum sulfate hydroxide particles having specific particle properties (particle shape, particle size uniformity, average secondary particle diameter, specific surface area, etc.). It also relates to a method of manufacturing the antibacterial agent.

Further, it relates to an antibacterial resin composition (including a master batch) having excellent filter passability at the time of kneading and extrusion and dispersibility as performances required when the antibacterial agent is kneaded and mixed with a resin. It also relates to antibacterial resin molded articles which are formed from the resin composition and excellent in dispersibility, transparency, whiteness and antibacterial properties (including antibacterial action retention characteristics after contact with tap water) and to antibacterial resin products such as antibacterial films, antibacterial fibers, antibacterial coatings, antibacterial nonwoven fabrics and antibacterial caulking materials. Further, it relates to antifungal agents, antibacterial deodorizing agents, antibacterial paper, agricultural chemicals and cosmetics.

DESCRIPTION OF THE PRIOR ART

In general, the multiplication of bacteria proceeds in a high-temperature and high-humidity environment, which may cause a serious problem in a residential environment from the viewpoints of safety and hygiene. To solve this problem, there is proposed a technology such as antibacterial resin compositions which are prepared by mixing an organic antibacterial agent or an inorganic antibacterial agent with a resin or others to be made antibacterial so as to prevent damage from bacteria. Out of these antibacterial agents, demand for the inorganic antibacterial agent is growing because the inorganic antibacterial agent is relatively safe.

As the inorganic antibacterial agent, there are proposed a large number of antibacterial resin compositions comprising an antibacterial agent which has silver carried on an inorganic compound or is ion exchanged with silver because silver has relatively high antibacterial activity and relatively high safety.

For example, JP-A 6-212019 discloses a technology for an antibacterial resin composition comprising silver carried on zirconium phosphate. However, the antibacterial resin composition prepared by mixing an antibacterial agent with a resin has slightly improved whiteness but is not perfect in terms of all of antibacterial properties, dispersibility, transparency and antibacterial action retention characteristics after contact with tap water and still has a problem to be solved.

Particularly, this prior art has a problem that when the antibacterial resin composition is used in contact with tap water for a while, the antibacterial activity of the resin composition is totally lost or greatly reduced, whereby it cannot be used for a long time and damage from bacteria cannot be prevented. Therefore, it is important to solve this problem.

Describing this problem with reference to a specific example, tap water is always used in kitchens, bathrooms and toilets and clothes are used many times by washing them in tap water. Therefore, antibacterial resin products used in these places or under the above condition must exhibit antibacterial properties to prevent damage from bacteria even when they come into contact with tap water for a long time. Although the antibacterial resin product of the prior art exhibits antibacterial properties to a certain extent right after the manufacture of the resin product, the antibacterial activity of the resin product is totally lost or greatly reduced after it is used in contact with tap water for a while and the resin product cannot prevent damage from bacteria at all after the passage of a long time.

JP-A 2000-7326 discloses a spindle-shaped or spherical alkali aluminum sulfate hydroxide which is represented by the formula $MAl_3(SO_4)_2(OH)_6$ (M is an alkali metal or ammonium group) and has a BET specific surface area of 30 $m^2$/g or less. In this document, particles having a sharpness $Rs=D_{25}/D_{75}$ of a particle size distribution obtained by dividing the particle diameter $D_{25}$ (on the large particle diameter side) of the 25% value by the particle diameter $D_{75}$ (on the small particle diameter side) of the 75% value of a volume-based cumulative particle diameter measured by a Coulter counter method of 1.45 to 1.61 are shown in Examples and the methods of manufacturing the particles and a resin composition comprising the particles are introduced.

The above patent document includes a general description that M of the compound can include an element having the effect of exhibiting antibacterial properties, such as Ag, Zn or Cu to obtain antibacterial particles. However, there are no descriptions and examples of an antibacterial agent and an antibacterial resin product.

JP-A 2000-7326 fails to disclose that particles having a high sharpness of 1.4 or less can be manufactured uniformly and the particles can be dispersed in a resin perfectly in a monodisperse state, thereby improving the performance of the particles and filter passability at the time of kneading and extrusion, and have excellent whiteness.

This patent document has no detailed description of an antibacterial resin composition prepared by mixing the antibacterial agent particles with a resin, antibacterial resin molded articles formed from the resin composition, and antibacterial resin products such as antibacterial films, antibacterial fibers, antibacterial coatings and antibacterial caulking materials, and antifungal agents, antibacterial deodorizing agents, antibacterial paper, agricultural chemicals and cosmetics.

SUMMARY OF THE INVENTION

It is therefore an object of the present invention to provide an antibacterial agent composed of silver-containing aluminum sulfate hydroxide particles which have solved the problems of the inorganic antibacterial agent of the prior art, have high dispersibility, transparency, whiteness and also excellent antibacterial properties, especially antibacterial action retention characteristics after contact with tap water when they are mixed with a substance to be made antibacterial such as a resin as the performances of an antibacterial agent, and contain silver in a specific amount, an antibacterial agent composed of silver-containing aluminum sulfate hydroxide particles which are designed to be excellent particularly in the above characteristic properties of the antibacterial agent and have specific particle properties (particle shape, particle size uniformity, average secondary particle diameter, specific surface area, etc.), and further a method of manufacturing the antibacterial agent.

It is another object of the present invention to provide an antibacterial resin composition (including a master batch) having excellent filter passability at the time of kneading and extrusion when an antibacterial agent is kneaded and mixed by using a resin kneading extruder and excellent dispersibility, antibacterial resin molded articles formed from the resin composition and having excellent dispersibility, transparency, whiteness and antibacterial properties, especially antibacterial action retention characteristics after contact with tap water, and antibacterial resin products such as antibacterial films, antibacterial fibers, antibacterial nonwoven fabrics, antibacterial coatings and antibacterial caulking materials.

The prior art has a problem that when an antibacterial resin product is used under a tap water contact environment for a while, its antibacterial activity is totally lost or greatly reduced in a short period of time. In view of this, it is still another object of the present invention to provide an antibacterial resin composition which can retain antibacterial properties for a long time even in places where tap water is always used, such as kitchens, bathrooms and toilets, or under the condition that products such as cloths are washed in tap water many times, products formed from the composition, an antibacterial agent to be mixed with the resin composition and a method of manufacturing the antibacterial agent.

Another important target is to attain a technology which is generally carried out before an antibacterial resin product is obtained, that is, to solve a problem that the machine cannot be operated for a long time and a filter must be exchanged in a short period of time due to low filter passability (pressure of an extruder) at the time of kneading and extruding a resin when a master batch (MB) is manufactured from a resin and an antibacterial agent by using a resin kneading extruder. If the machine can be operated for a longer time, resources, energy, labor and time required for exchanging the filter can be cut, thereby making it possible to provide an antibacterial resin composition and an antibacterial resin product to the society at a lower cost, which is of great industrial value.

It is a further object of the present invention to provide products other than the above antibacterial resin products, making use of the characteristic properties of the antibacterial agent, that is, antifungal agents, antibacterial deodorizing agents, antibacterial paper, agricultural chemicals and cosmetics.

The inventors of the present invention have conducted intensive studies to attain the above objects and have found that silver-containing aluminum sulfate hydroxide particles represented by the following formula (X-I) or (Y-I) have excellent antibacterial properties as the performance of an antibacterial agent, a resin composition comprising the particles and molded articles formed from the composition are also excellent in antibacterial properties as well as filter passability at the time of kneading and extrusion, whiteness, transparency and antibacterial action retention characteristics after contact with tap water, and antibacterial resin products such as antibacterial films, antibacterial fibers, antibacterial nonwoven fabrics, antibacterial coatings and antibacterial caulking materials are also excellent in whiteness, transparency and antibacterial action retention characteristics after contact with tap water. The present invention has been accomplished based on this finding.

The inventors have further found that the above particles can be advantageously used in antifungal agents, antibacterial deodorizing agents, agricultural chemicals and cosmetics other than molded articles, making use of their antibacterial properties. The present invention has also been accomplished based on this finding.

According to the present invention, there is provided an antibacterial agent composed of silver-containing aluminum sulfate hydroxide particles represented by the following formula (X-I) or (Y-I).

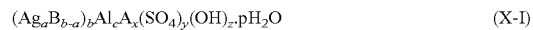

$(Ag_aB_{b-a})_bAl_cA_x(SO_4)_y(OH)_z \cdot pH_2O$            (X-I)

In the formula (X-I), a, b, c, x, y, z and p satisfy $0.00001 \leq a < 0.5$, $0.7 \leq b \leq 1.35$, $2.7 < c < 3.3$, $0.001 \leq x \leq 0.5$, $1.7 < y < 2.5$, $4 < z < 7$ and $0 \leq p \leq 5$, respectively, B is at least one monovalent cation selected from the group consisting of $Na^+$, $NH_4^+$, $K^+$ and $H_3O^+$, the total value (1b+3c) obtained by multiplying the valences by the numbers of mols of the cations satisfies $8 < (1b+3c) < 12$, and A is an organic acid anion.

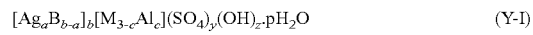

$[Ag_aB_{b-a}]_b[M_{3-c}Al_c](SO_4)_y(OH)_z \cdot pH_2O$            (Y-I)

In the formula (Y-I), a, b, c, y, z and p satisfy $0.00001 \leq a < 0.5$, $0.8 \leq b \leq 1.35$, $2.5 \leq c \leq 3$, $1.7 < y < 2.5$, $4 < z < 7$ and $0 \leq p \leq 5$, respectively, B is at least one monovalent cation selected from the group consisting of $Na^+$, $NH_4^+$, $K^+$ and $H_3O^+$, and M is Ti or Zn.

BEST MODE FOR PRACTICAL EMBODIMENT OF THE INVENTION

Figure 1:
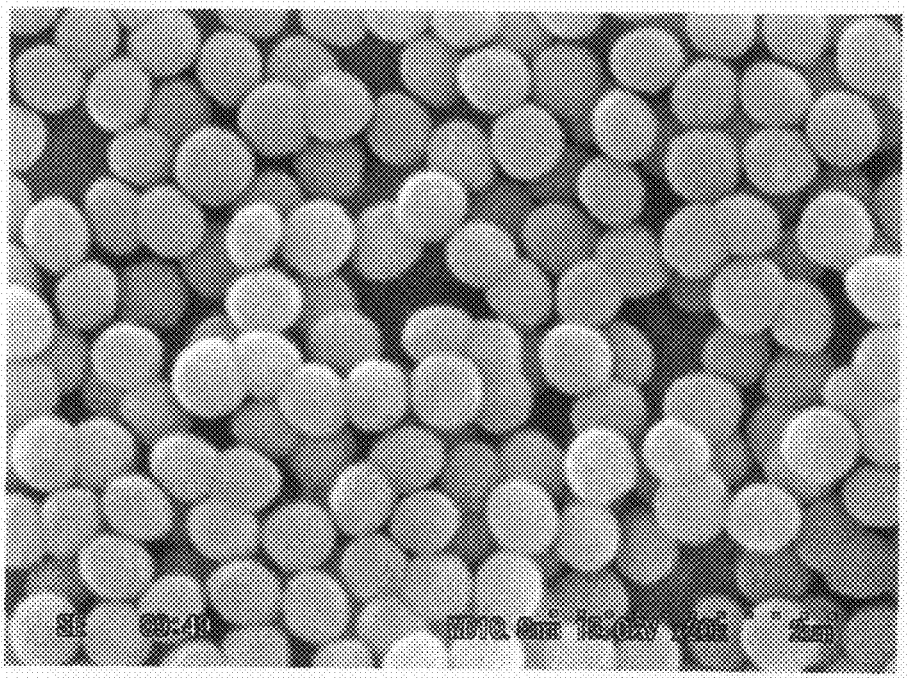
FIG. 1 is a SEM photomicrograph of spherical particles A1 in Example X-I-1.

The antibacterial agent of the present invention and its use will be described hereinunder in detail.

Aluminum sulfate hydroxide particles as the antibacterial agent of the present invention are a compound represented by the above formula (X-I) or (Y-I). The compounds represented by the formula (X-I) and (Y-I) contain silver and exhibit an excellent antibacterial function based on this. The particles of the compounds represented by the above formulas (X-I) and (Y-I) are very unique in terms of particle shape, particle distribution, particle size, cohesiveness and uniformity and excellent in terms of dispersibility in a resin, affinity, stability and moldability.

Out of the aluminum sulfate hydroxide particles of the present invention, the compound represented by the formula (X-I) contains silver and an organic acid anion (A) in the molecule and the compound represented by the formula (Y-I) contains silver in the molecule but not the organic acid anion (A).

In the text below, the compound represented by the formula (X-I) may be referred to as "silver- and organic acid anion-containing aluminum sulfate hydroxide". The particles of the compound represented by the formula (X-I) may be referred to as "particles (X-I)" and the antibacterial agent composed of the particles (X-I) may be referred to as "antibacterial agent particles (X-I)".

Further, the particles of the compound represented by the formula (Y-I) may be referred to as "particles (Y-I)" and the antibacterial agent composed of the particles (Y-I) may be referred to as "antibacterial agent particles (Y-I)".

In this text, it is to be understood that the term "antibacterial agent of the present invention" or "antibacterial agent" embraces both the antibacterial agent particles (X-I) and the antibacterial agent particles (Y-I).

The particles of the compound represented by the formula (X-I) and the particles of the compound represented by the formula (Y-I) of the present invention will be described hereinbelow in this order.

I). Aluminum Sulfate Hydroxide Particles Represented by the Formula (X-I):

According to the present invention, it has been found that the antibacterial agent particles represented by the above formula (X-I) have the following characteristic properties (i), (ii) and (iii) independently.

(i) an average secondary particle diameter measured by a laser diffraction scattering method of 0.1 to 12 μm, preferably 0.1 to 5 μm
(ii) a BET specific surface area of 0.1 to 250 $m^2/g$, preferably 1 to 100 $m^2/g$
(iii) a sharpness of the particle size distribution defined as $Dr=D_{75}/D_{25}$ ($D_{25}$ is the particle diameter (on the small particle diameter side) of the 25% value of a volume-based cumulative particle size distribution curve measured by the laser diffraction scattering method and $D_{75}$ is the particle diameter (on the large particle diameter side) of the 75% value) of 1.0 to 1.8, preferably 1.01 to 1.5, more preferably 1.01 to 1.3, most preferably 1.01 to 1.2

The above average secondary particle diameter (i), BET specific surface area (ii) and sharpness (Dr) of the particle size distribution (iii) are independent from one another. Particles which have two out of the three properties at the same time are preferred and particles which have all of them are most preferred to attain the object of the present invention.

Further, when the antibacterial agent particles (X-I) of the present invention are characterized in that they are not agglomerated but monodisperse and have the following particle shapes.

Although the antibacterial agent particles (X-I) of the present invention have various shapes, they are characterized in that they are uniform in shape and size, rarely agglomerated and monodisperse. As for particle shapes, the particles of the antibacterial agent are roughly divided into spherical, disk-like ("go" stone-like), paired (hamburger-like), rice grain-like, rectangular parallelepiped, hexagonal plate-like, columnar (cask-like) and octahedral particles. These particle shapes will be described in detail with reference to FIGS. 1 to 13.

FIGS. 1 to 13 are SEM photomicrographs of typical particles obtained in Examples of the present invention. The shapes of the particles are observed based on their SEM photomicrographs enlarged at about 10,000× to 2,0000×. FIG. 14 is a SEM photomicrograph of conventionally known alkali aluminum sulfate hydroxide particles.

Examples of the spherical particles are shown in FIGS. 1 to 6. These spherical particles can be divided into spherical particles having a smooth surface shown in FIG. 1, spherical particles having small grains on the surface shown in FIG. 2, spherical particles having a rough surface and wrinkles (scratches or cracks) shown in FIG. 3, spherical particles having small holes (unevenness) shown in FIG. 4, spherical particles having a smooth surface and more linear portions than those of FIG. 1 shown in FIG. 5, and spherical particles having a rough surface and wrinkles shown in FIG. 6.

Figure 7:
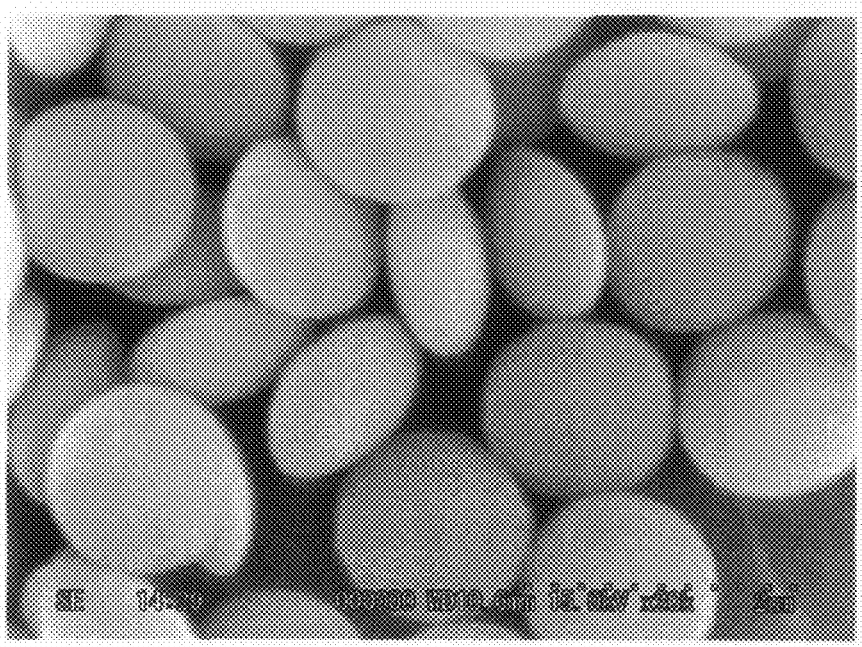
FIG. 7 is a SEM photomicrograph of disk-like particles B1-1 in Example X-I-32-1.

An example of the disk-like particles is shown in FIG. 7. The particles have almost symmetrical and domed front and rear sides and are shaped like a "go" stone. The disk-like particles shown in FIG. 7 have a smooth surface.

Figure 8:
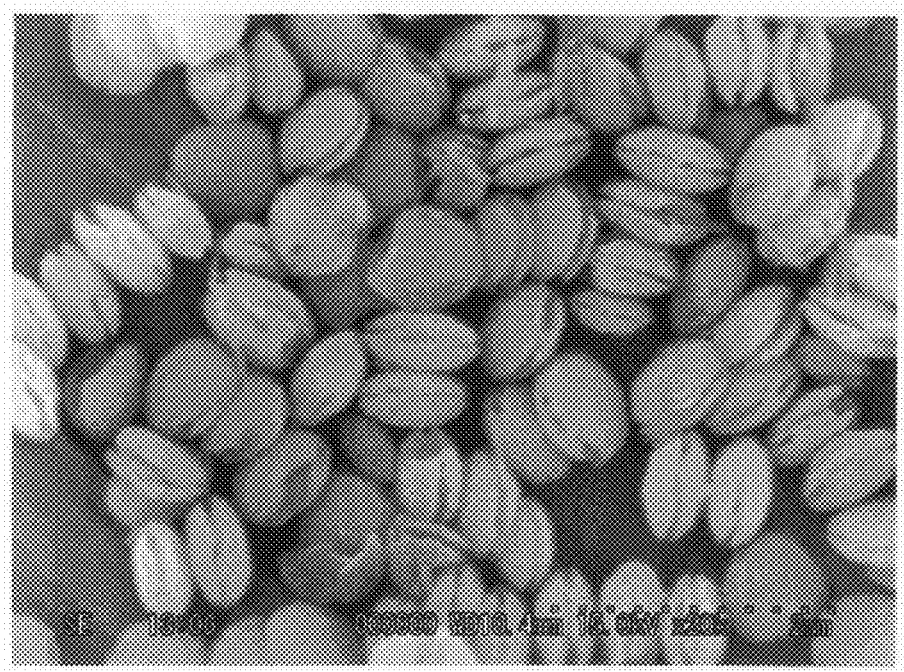
FIG. 8 is a SEM photomicrograph of paired particles C1 in Example X-I-35.

An example of the paired particles is shown in FIG. 8. The characteristic feature of the particles is that two disk-like particles having a flat bottom surface and a domed opposite surface are paired with the bottom surfaces as symmetry planes, and a space exists between the peripheries of the two particles. An aluminum salt hydroxide for bonding the two disks exists in the center portions of the mating surfaces. This paired particles look like a hamburger.

Figure 9:
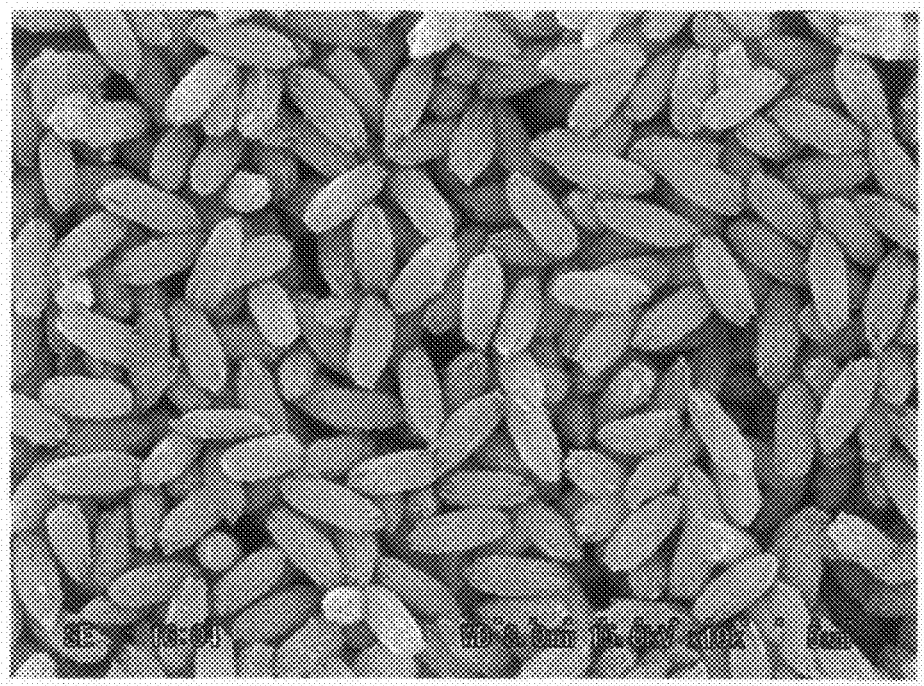
FIG. 9 is a SEM photomicrograph of rice grain-like particles D1 in Example X-I-38.

An example of the rice grain-like particles is shown in FIG. 9. The projected shape of each rice grain-like particle is elliptic and its section in the direction perpendicular to the longitudinal direction is almost circular. The particles of FIG. 9 have small wrinkles on the surface.

Figure 10:
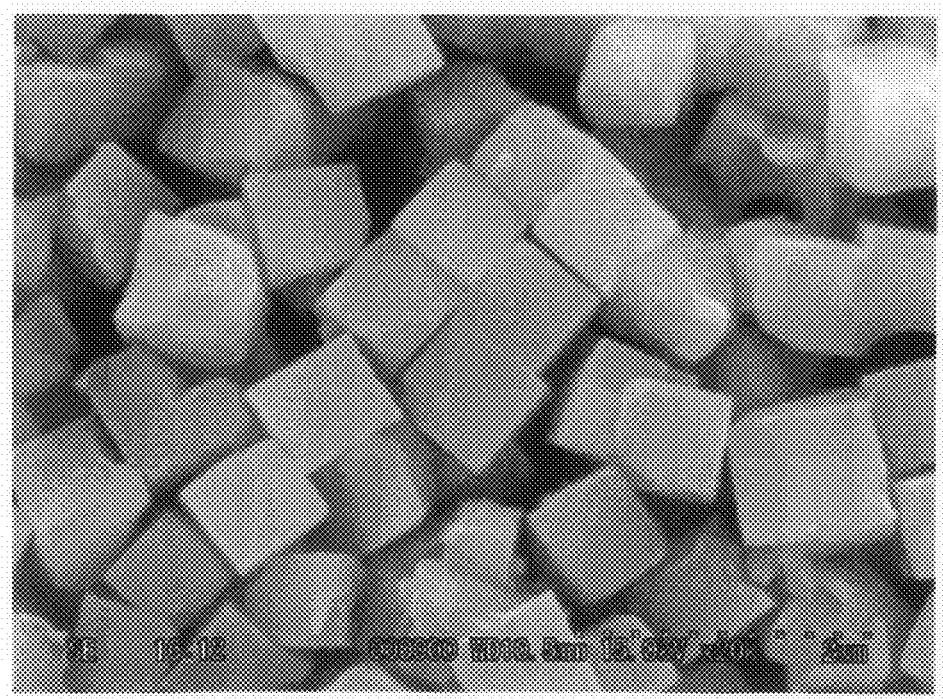
FIG. 10 is a SEM photomicrograph of rectangular parallelepiped particles E1 in Example X-I-41.

An example of the rectangular parallelepiped particles is shown in FIG. 10 and they are a rectangular parallelepiped close to a regular hexahedron and have a smooth surface.

Figure 11:
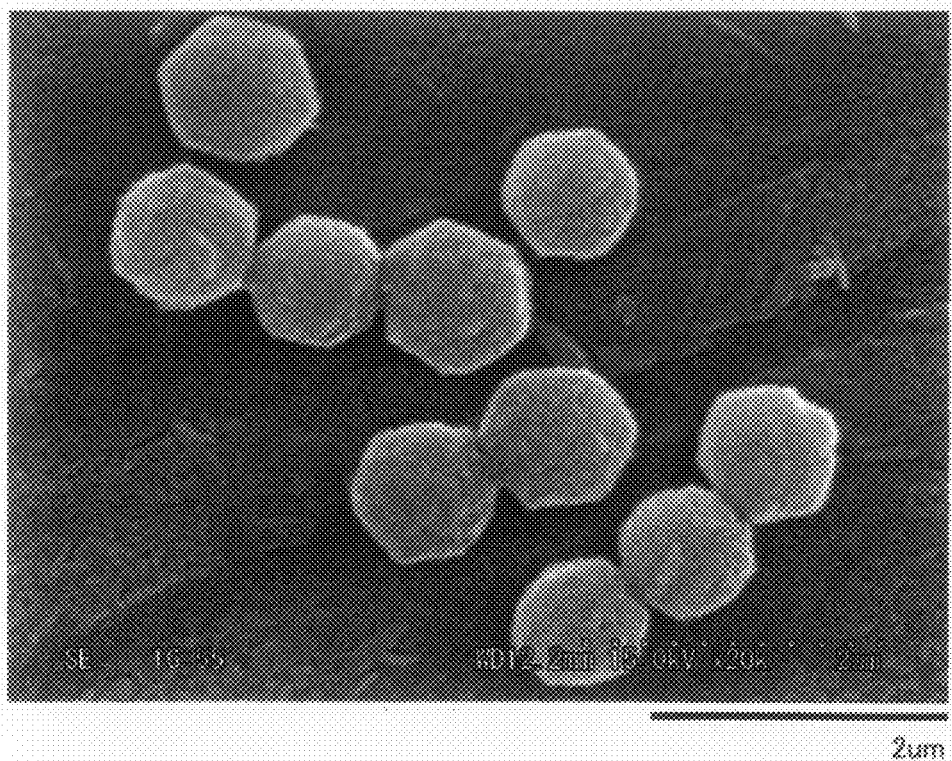
FIG. 11 is a SEM photomicrograph of hexagonal plate-like particles F1 in Example X-I-45.

An example of the hexagonal plate-like particles is shown in FIG. 11. The hexagonal plate-like particles are shaped like a plate having the faces of a hexahedron formed by six sides. The six sides do not need to have the same length and contact points between adjacent two sides may be round.

Figure 12:
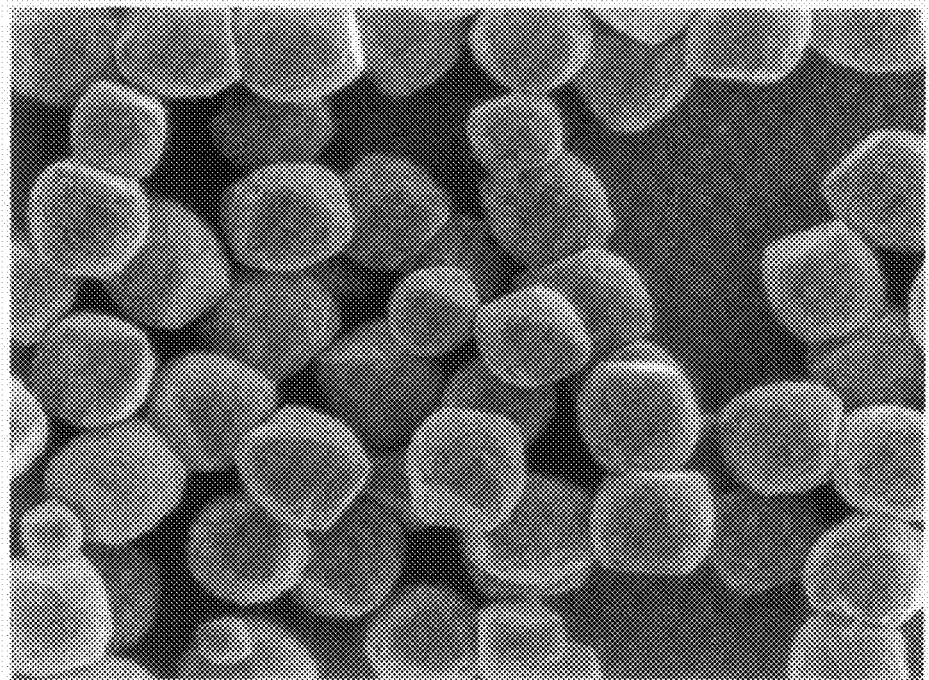
FIG. 12 is a SEM photomicrograph of octahedral particles G1 in Example X-I-46.

An example of the octahedral particles is shown in FIG. 12. They are shaped like an octahedral assembly of two pyramids or biased octahedron.

Figure 13:
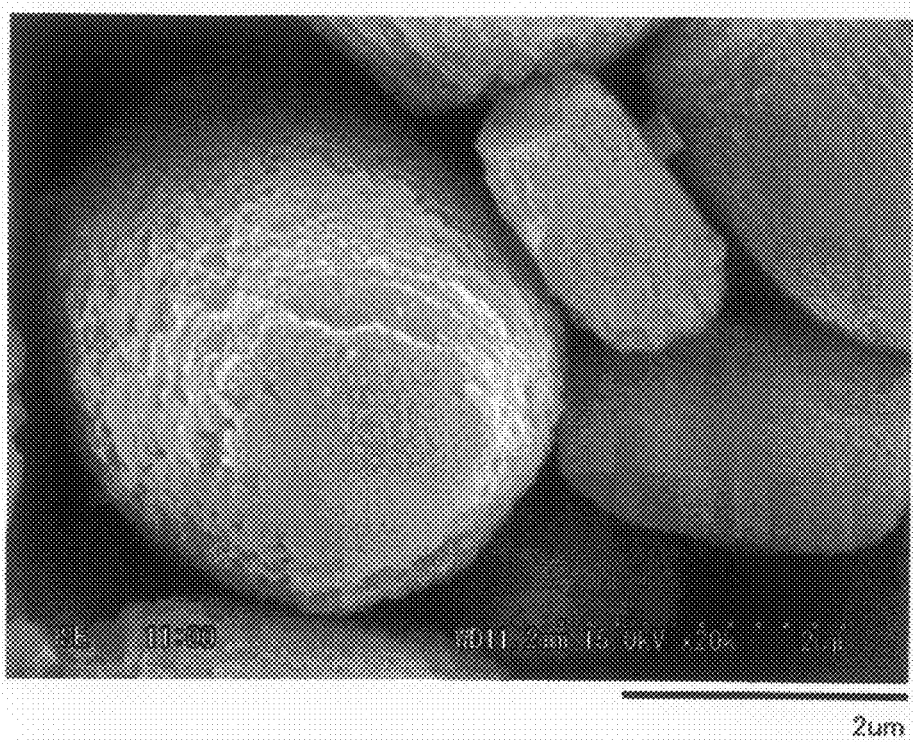
FIG. 13 is a SEM photomicrograph of columnar particles H1 in Example X-I-47.
Figure 14:
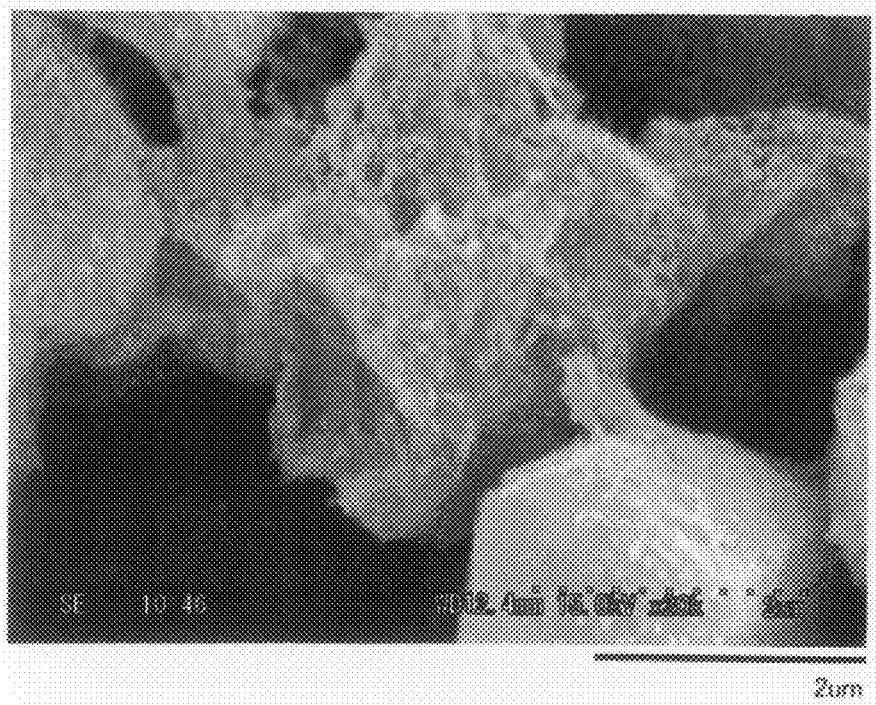
FIG. 14 is a SEM photomicrograph of agglomerated particles V1 in Comparative Example X-I-1.

An example of the columnar particles is shown in FIG. 13. Each columnar particle may have a swelling middle portion substantially like a sake cask (or wine cask) or may be shaped like a cylinder having an almost round section.

The particles of FIG. 13 have a large number of irregularities on the surface.

As understood from FIGS. 1 to 13, the particles of the present invention are uniform in shape and size in the figures (photomicrographs) and have high dispersibility. The shapes of the above particles are expressed to classify the particles, and the particles may be slightly deformed or include other particles in a small amount. The surface smoothness, fine irregularities and small wrinkles on the surface of each particle are not particularly limited and may be existent or nonexistent.

A description is subsequently given of the method of specifying the shape of the particles (X-I) of the present invention.

One of the indices for specifying the shape of the particles is Wadell's circularity and sphericity which have been used in the field of the powder industry.

Wadell's sphericity "s" is defined as s=(surface area of sphere having the same volume as particle)/(surface area of particle). As "s" is closer to 1, the particle is more spherical.

Wadell's circularity "c" is defined as c=(circumference of the same area as projected area of particle)/(circumference of plane of projection of particle) As "c" is closer to 1, the particle is more circular.

In the present invention, the spherical shape of the particle means that the particle may be shaped like a ball as shown in FIGS. 1 to 6 and has a Wadell's sphericity "s" which preferably satisfies $0.95 \leq s \leq 1$.

In the present invention, the disk-like shape ("go" stone-like shape) of the particle means a spheroidal shape with the short diameter as the axis of rotation as shown in FIG. 7. More specifically, the projected image of the particle when seen in the direction of the axis of rotation has a Wadell's circularity "c" which satisfies $0.95 \leq s \leq 1$ and a (short diameter/long diameter) ratio "a" of the elliptic section which preferably satisfies $0.05 \leq a \leq 0.5$.

In the present invention, the paired shape (hamburger-like shape) of the particle means that two hemispherical particles are paired as shown in FIG. 8. There exist a gap (groove) between the peripheries of the mating surfaces of the two hemispherical particles. Preferably, the (short diameter/long diameter) ratio "t" of the paired particles satisfies $0.1 < t < 0.5$ and the (width of gap between mating surfaces of hemispheres)/(short diameter) ratio "u" satisfies $0.05 < u < 0.5$.

In the present invention, the rice grain-like shape of the particle means a spheroidal shape with the short diameter as the axis of rotation as shown in FIG. 9. Preferably, the (short diameter/long diameter) ratio "a" of the ellipse satisfies $0.1 \leq a \leq 0.5$ and the Wadell's sphericity "s" satisfies $0.4 \leq s < 0.75$.

In the present invention, the rectangular parallelepiped shape of the particle means that the particle may have a shape similar to a hexahedron as shown in FIG. 10 or a regular hexahedron. The Wadell's sphericity "s" preferably satisfies $0.5 \leq s \leq 0.8$.

In the present invention, the hexagonal plate-like shape of the particle means a flat regular hexagonal pillar-like shape as shown in FIG. 11. Preferably, the Wadell's circularity "c" of the projected image of the particle when it is seen from the top surface or the bottom surface satisfies $0.95 \leq c < 0.99$ and the (thickness/(length of diagonal line of regular hexagon) ratio "b" satisfies $0.05 \leq b \leq 0.5$.

In the present invention, the octahedral shape of the particle means that the particle is considered to be shaped like an octahedral assembly of two pyramids or a biased octahedron as shown in FIG. 12. The above Wadell's sphericity "s" preferably satisfies $0.5 \leq s \leq 0.9$. Without gazing intently at this octahedral particle, it may look like a hexahedral particle due to an unclear image caused by the insufficient resolution of the SEM photomicrograph.

In the present invention, the columnar (cask-like) shape of the particle includes a columnar shape as shown in FIG. 13 and covers a shape having a radius of the center portion in the height direction of a column which is 1.0 to 1.2 times the radius of the top surface and the bottom surface. Preferably, the above Wadell's circularity "c" based on the projected images of the top surface and the bottom surface satisfies $0.95 \leq c < 0.99$ and the (height)/(diameter of top surface or bottom surface) ratio "d" satisfies $1.5 \leq d \leq 3$.

According to the present invention, as described above, silver- and organic acid anion-containing aluminum sulfate hydroxide particles (X-I) which are various in shape such as spherical, disk-like ("go" stone-like), paired, rectangular parallelepiped, hexagonal plate-like, rice grain-like, octahedral and columnar can be provided according to application and purpose, and the particle diameters of the particles can be controlled.

Meanwhile, silver- and organic acid anion-containing aluminum sulfate hydroxide particles having an optimum particle diameter can be provided according to application and required packing.

The particles are not agglomerated and are excellent in dispersibility in a resin, and the agglomeration of the antibacterial agent in the resin does not occur or rarely occurs when they are mixed with the resin, which is considered as one of factors that a resin product comprising the antibacterial agent and a resin exhibits antibacterial properties even when the content of silver in the resin product is very low. Only this monodisperse technology exhibits unexpectedly high antibacterial activity which can be hardly attained by the technology of the prior art.

As for the mechanism of the antibacterial agent particles (X-I) of the present invention which exhibit such unexpectedly high antibacterial activity, the following second factor is also presumed.

The reason why the antibacterial agent particles (X-I) of the present invention exhibit such high antibacterial properties is presumed to be that a radical such as a hydroxyl radical ($OH^-$) is readily formed from the antibacterial agent particles for a long time when the antibacterial agent of the present invention is exposed to light as the organic acid is introduced into the internal structure of the molecule of each of the antibacterial agent particles as an anion, which is one of the factors for enabling the antibacterial performance of the antibacterial agent of the present invention to be maintained for a long time.

Most of silver-based inorganic antibacterial agents of the prior art have a fatal defect that they do not exhibit antibacterial properties any more after they release silver ions though they exhibit antibacterial properties while they can release silver ions. The present invention basically solves this problem.

In addition, according to the present invention, as a third factor of an antibacterial property development improving effect which is obtained by introducing the organic acid into the molecular structure of each of the antibacterial agent particles (X-I) of the present invention as an anion, it is presumed that higher antibacterial performance can be provided not only by the above dispersion effect and the radical forming effect but also by the effect of improving compatibility between the carbons of the organic acid of the antibacterial agent particle and the resin, that is, the multiplication of these three effects in the present invention.

The composition of the compound of the formula (X-I) will be described in detail hereinunder.

In the formula (X-I) of the present invention, "a" represents the amount of silver ion exchanged into the antibacterial agent particles. As the numerical value "a" becomes larger, more silver is ion exchanged into the antibacterial agent particles with the result of improved antibacterial properties.

When the numerical value "a" becomes too large, silver may separate out or elute from an ion exchanger (solid solution) in the environment to become silver oxide, whereby the color of a resin molded article comprising the antibacterial agent may become dark brown and it is not economical. When "a" is 0.5 or more, ion exchange becomes difficult. When the numerical value "a" becomes too small, the amount of silver ion exchanged into the antibacterial agent particles is small and antibacterial properties are hardly developed. Therefore, to balance antibacterial property developing force with the color problem properly, "a" is desirably set to a fixed range. In this sense, "a" in the formula (X-I) is in the range of 0.00001 to 0.5, preferably 0.00001 to 0.35, more preferably 0.001 to 0.3.

In the present invention, the word "containing" in the expression "bacterial agent composed of silver- and organic acid anion-containing aluminum sulfate hydroxide particles" means that the antibacterial agent is a substance containing such a small amount of a compound comprising silver and an organic acid represented by a formula other than the formula (X-I) that a peak derived from the compound other than the compound of the formula (X-I) does not appear when the particles are measured by the powder X-ray diffraction method.

Therefore, it is considered that the antibacterial agent particles are particles carrying a small amount of silver not only in the form of an ion exchanger but also in other form which does not appear as a peak measured by the powder X-ray diffraction method and/or particles having a small amount of an organic acid anion adsorbed to the surface.

In this case, when paying attention to silver, it is considered that the antibacterial agent particles consisting of a solid solution alone ion exchanged with silver within an ion exchange allowable range have a small influence upon the color of a resin product. In this sense, the antibacterial agent particles preferably consist of a perfect silver ion exchanger (solid solution) alone.

In the formula (X-I) of the present invention, B may be any type of monovalent cation. In fact, when it is taken into consideration that "B" has an ion radius relatively close to that of the silver ion and can form an ion exchanger strongly at a wide range, that is, silver does not separate from the ion exchanger to become silver oxide when it is mixed with a resin with the result that a reduction in the whiteness of a resin product (the resin product changes its color from white to dark brown or brown right after molding along the passage of time by the function of light) hardly occurs and further safety and economy are taken into account, $Na^+$, $NH_4^+$, $K^+$ or $H_3O^+$ is suitable as B. B is relatively preferably $Na^+$, $NH_4^+$ or $H_3O^+$, more preferably $NH_4^+$ or $H_3O^+$, most preferably $NH_4^+$ for the above purpose. From the viewpoint of preventing discoloration, the amount of $Na^+$ and/or $K^+$ used as B is preferably as small as possible and the amount of $K^+$ is preferably smaller than ½ of the total molar amount of the monovalent cations as B when $K^+$ is used. Discoloration can be prevented by adding a fluorescent brightener to a resin in an amount of 0.000001 to 0.1%. Therefore, when $Na^+$ and $K^+$ are used as B in large quantities, it is preferred to use a fluorescent brightener for the prevention of discoloration.

In the case of antibacterial agent particles comprising three different monovalent cations which are $Na^+$, $NH_4^+$ and $H_3O^+$ as part of the antibacterial resin composition of the present invention as a relatively preferred example, in order to obtain a resin product which does not discolor or rarely discolors without using a fluorescent brightener, the molar amount of Na should be smaller than ½ of the total molar amount of the monovalent cations as B. Thereby, a resin product which does not discolor or rarely discolors can be obtained in the present invention.

When the fluorescent brightener is used, benzohexazole-based fluorescent brighteners such as 2,5-thiophenediyl(5-tert-butyl-1,3-benzohexazole, 4,4'-bis(benzohexazol-2-yl) stilbene, and pyrazoline-based fluorescent brighteners and coumarine-based fluorescent brightness may be used as the fluorescent brighter, out of which fluorescent brighteners registered at FDA (Food & Drag Administration of the U.S.) and the Polyolefin Hygiene Council are preferably used.

When "b" in the formula (X-I) of the present invention is 0.7 to 1.35, preferably 0.8 to 1.2, most preferably 0.9 to 1.1, the antibacterial agent particles of the present invention are readily formed. When "c" is 2.7 to 3.3, preferably 2.8 to 3.2, most preferably 2.9 to 3.1, the antibacterial agent particles of the present invention are readily formed.

The valences of the cations in the formula (X-I) x the numbers of mols of the cations is expressed as (1b+3c). When (1b+3c) satisfies 8<(1b+3c)<12, preferably 9<(1b+3c)<11, the antibacterial agent particles of the present invention are readily formed.

In order to manufacture the particles by selecting the particle shape and the particle size, to make uniform the particle size distribution and to disperse the particles into a resin in a monodisperse state as much as possible in the synthesis of the antibacterial agent particles (X-I) of the present invention, an organic acid must be added during a reaction so that the organic acid added can be incorporated into the molecular structures of the antibacterial agent particles.

The organic acid is, for example, an organic acid whose organic acid anion (A) in the formula (X-I) is at least one selected from anions based on organic carboxylic acids and organic oxycarboxylic acids. The organic acid anion (A) is preferably at least one selected from anions based on organic carboxylic acids and organic oxycarbooxylic acids having 1 to 15 carbon atoms, preferably 1 to 10 carbon atoms and 1 to 4 carboxyl groups, such as dicarboxylic acid, monocarboxylic acid, tricarboxylic acid, chain carboxylic acid, aromatic carboxylic acid, hydroxy acid, ketonic acid, aldehydeacid, phenolicacid, aminoacid, halogenocarboxylic acid and salts thereof. Out of these, the organic acid anion (A) is most preferably at least one selected from the group consisting of oxalic acid ion, citric acid ion, malic acid ion, tartaric acid ion, glyceric acid ion, gallic acid ion and lactic acid ion.

When the amount "x" of the organic acid anion (A) in the formula (X-I) satisfies $0.0001 \leq x \leq 0.5$, preferably $0.0001 \leq x \leq 0.4$, more preferably $0.001 \leq x \leq 0.2$, the above object is attained and antibacterial agent particles having the above particle shape and particle size uniformity are obtained. When "x" is larger than 0.5, this effect is not enhanced any more and it is not economical.

When "x" is smaller than 0.0001, antibacterial agent particles having the above shape and particle size uniformity are hardly obtained, and the object of the present invention such as the improvement of antibacterial properties considered to be caused by the formation of the above hydroxyl radical and the effect of improving compatibility between the organic acid and the resin is hardly attained.

When "y" in the formula (X-I) of the present invention satisfies 1.7<y<2.5, preferably 1.8<y<2.2, the antibacterial agent particles of the present invention are readily formed. When "z" satisfies 4<z<7, preferably 5<z<7, the antibacterial agent particles of the present invention are more readily formed.

"P" in the formula (X-I) represents the amount of crystal water and generally satisfies $0 \leq p \leq 5$. To make "p" as close to "0" as possible or make it "0", drying at 350° C. or lower or baking must be carried out additionally. Baking is preferably carried out at 600° C. or lower. When the baking temperature is 500° C. or higher, further 550° C. or higher, particularly 600° C. or higher, a water-soluble aluminum sulfate represented by the following formula may be partially formed and the water resistance of a resin product comprising the same may deteriorate. When the amount of the aluminum sulfate is small, there is no problem with the water resistance.

$$(Ag_aB_{b-a})_bAlA_x(SO_4)_y$$

When the baking temperature is 500° C. or lower, particularly 450° C. or lower, the water-soluble aluminum sulfate represented by the above formula is not formed and even when a large amount of this aluminum sulfate is used in a resin product, water resistance does not lower. When the antibacterial agent particles (X-I) of the present invention are baked at 600° C. or higher, the particle shapes of the antibacterial agent particles of the present invention as shown in FIGS. 1 to 13 may not be maintained. From the viewpoints of water resistance and shape retention, the baking temperature of the antibacterial agent particles of the present invention is 350 to 600° C., preferably 350 to 550° C., more preferably 350 to 500° C., most preferably 350 to 450° C.

It is preferred to carry out the above drying or baking step in a nitrogen atmosphere from the viewpoint of preventing the discoloration of the antibacterial agent particles and a resin product comprising the antibacterial agent particles. Carrying out the drying step in a vacuum is preferred from the viewpoint of preventing the coloration.

When there is no problem in the processing of a resin if p is not "0", for example, when the amount of the antibacterial agent is very small or when a resin has a water content which does not cause a problem at the time of processing, a resin composition can be manufactured by mixing the particles of the formula (X-I) in which p satisfies $0 \leqq p \leqq 5$, preferably $0 \leqq p \leqq 3$ and which are not dried or baked with a resin.

On the other hand, when there is a problem if p is not "0" or not close to "0", the particles of the formula (X-I) in which p is "0" or close to "0" obtained by adding a drying or baking step must be used.

For example, in the case of a polyester resin such as PET or PBT, polyamide-based resin, polyurethane-based resin, polycarbonate resin or polyacetal resin, it can be recommended to use the antibacterial agent which is dried or baked under the above condition to make "p" (water content) "0" or close to "0".

It is considered that the particles of the formula (X-I) of the present invention can be dispersed into a resin completely without being agglomerated by controlling the sharpness (Dr) of the particle size distribution measured by the laser diffraction scattering method to a range that satisfies $1.0 \leqq Dr \leqq 1.8$, preferably $1.0 \leqq Dr \leqq 1.5$, more preferably $1.01 \leqq Dr \leqq 1.3$, most preferably $1.01 \leqq Dr \leqq 1.2$, which is a factor for improving an antibacterial effect. Further, even when a filter (screen mesh) is used at the time of extruding a resin, particularly the manufacture of a master batch, the screen mesh is not or rarely clogged up with the antibacterial agent advantageously.

For the purpose of providing high antibacterial properties to an antibacterial resin product comprising the antibacterial agent of the present invention, particles having a small average secondary particle diameter, specifically 0.1 to 12 μm, preferably 0.1 to 5 μm, more preferably 0.1 to 2 μm, much more preferably 0.1 to 1 μm, most preferably 0.1 to 0.5 μm are used.

When the average secondary particle diameter of the antibacterial agent particles (X-I) is smaller than 0.1 μm, the particles may be hardly manufactured and when the average secondary particle diameter is larger than 12 μm, the antibacterial properties of a resin composition comprising the particles may not be improved. For the purpose of providing not only antibacterial properties but also high transparency to a resin composition, when super fine particles having an average secondary particle diameter of 0.1 to 0.5 μm, preferably 0.1 to 0.4 μm, more preferably 0.1 to 0.3 μm are used out of the antibacterial agents of the present invention, most use can be made of the characteristic properties of the antibacterial agent particles of the present invention whose refractive index overlaps or is close to the refractive index of a resin and the effect of providing higher transparency which cannot be attained by the prior art to a resin product is provided to a great extent.

The antibacterial agent used in the present invention has a BET specific surface area of 0.1 to 250 m²/g.

To provide high antibacterial properties to the resin composition, antibacterial agent particles having a larger BET specific surface area are advantageous. However, when the particles have a too large BET specific surface area, it may be difficult to charge the particles into a resin and when the particles have a too small BET specific surface area, they may be unable to provide sufficiently high antibacterial properties to the resin composition.

In this sense, the BET specific surface area of the antibacterial agent is 0.1 to 250 m²/g, preferably 1 to 100 m²/g, more preferably 10 to 100 m²/g, most preferably 30 to 100 m²/g.

A description is subsequently given of the method of manufacturing the antibacterial agent particles (X-I) represented by the formula (X-I) of the present invention.

The antibacterial agent particles (X-I) of the present invention can be basically manufactured by ion exchanging the monovalent cation (B) of organic acid anion-containing aluminum sulfate hydroxide particles represented by the following formula (X-II) which can be manufactured by the method described in the specification of PCT/JP2005/003831 (filing date: Mar. 1, 2005). Examples of this method will be described in the paragraphs 1 to 4 hereinafter.

$$[B]_bAl_cA_x(SO_4)_y(OH)_z \cdot pH_2O \quad (X\text{-}II)$$

In the formula, b, c, x, y, z, p, B and A are as defined in the above formula (X-I).

To synthesize the compound of the formula (X-II), aluminum and sulfuric acid source materials such as aluminum sulfate, sodium sulfate, potassium sulfate, ammonium sulfate and calcium sulfate, an organic acid source material such as oxalic acid, and an alkali source material such as sodium hydroxide, potassium hydroxide or ammonia aqueous solution are reacted with one another by a dry or wet process to synthesize organic acid anion-containing aluminum sulfate hydroxide particles but not containing sodium-, potassium- or ammonium-type silver as B [spherical, disk-like ("go" stone-like), paired (hamburger-like), rice grain-like, hexagonal plate-like, octahedral and columnar particles will be described in the paragraphs 1 to 3 hereinafter] which are then brought into contact with a silver solution in a suspension such as water under agitation to ion exchange silver into the organic acid anion-containing aluminum sulfate hydroxide particles, thereby making it possible to manufacture the antibacterial agent particles of the present invention.

The method of manufacturing rectangular parallelepiped silver- and organic acid anion-containing aluminum sulfate hydroxide particles will be described in the paragraph 4 hereinafter.

In either case, in order to manufacture silver- and organic acid anion-containing aluminum sulfate hydroxide particles by selecting their shape and particle size, make the particle size distribution uniform and disperse the particles into a resin perfectly in a monodisperse state, the above organic acid must be added during the above reaction so that the added organic acid can be incorporated into the structures of the antibacterial agent particles.

It is considered that part of the organic acid may adsorb to the surfaces of the antibacterial agent particles. Anyway, the organic acid can be contained in the antibacterial agent in order to attain the object of the present invention.

When the organic acid is added not during the reaction but after the end of the reaction, the antibacterial agent particles of the present invention having the above particle shape, particle size uniformity and dispersibility cannot be manufactured.

To grind the manufactured antibacterial agent particles of the present invention, strong mechanical force does not need to be used unlike the prior art and non-agglomerated particles are obtained even when weak force is used, which is the feature of the technology of the present invention.

Examples of the method of manufacturing sodium, potassium, ammonium and hydrogen type silver- and organic acid anion-containing aluminum sulfate hydroxide particle antibacterial agents are given below.

1. Method of manufacturing sodium type silver- and organic acid anion-containing aluminum sulfate hydroxide particles;

The above sodium type silver- and organic acid anion-containing aluminum sulfate hydroxide particles are manufactured from a sulfate such as aluminum sulfate or sodium sulfate, an Al source material, a $SO_4$ source material, a Na source material such as sodium hydroxide, an organic acid source material such as oxalic acid and a soluble silver salt such as silver nitrate which is used for an ion exchange reaction as a silver source material by the following method.

For example, after $Al_2(SO_4)_3+Na_2SO_4$ (or $NaNO_3$)+$H_2C_2O_4$ are fully dissolved in water, sodium hydroxide is added to the resulting solution under agitation. After addition, they are preferably stirred for another 20 minutes to disperse sodium hydroxide in the solution completely. Thereafter, a hydrothermal treatment is preferably carried out. The hydrothermal treatment temperature is preferably 100 to 250° C. and the treatment time is preferably 1 to 30 hours.

The thus obtained organic acid anion-containing aluminum sulfate hydroxide particles are filtered and optionally rinsed.

When the particles are suspended in a liquid such as water and stirred together with a solution of a soluble silver salt such as silver sulfate or silver nitrate, an ion exchange reaction can be carried out to manufacture the silver- and organic acid anion-containing aluminum sulfate hydroxide particles of the present invention.

The temperature of the ion exchange reaction is preferably 0 to 100° C., and the treatment time is preferably 0.1 to 30 hours under shaded light.

When the ion exchange reaction temperature is too low or the treatment time is too short, the amount of silver ion exchanged may be small. When the ion exchange reaction temperature is too high or the treatment time is too long, the ion exchanged product may be colored brown. The agitation means during the ion exchange reaction is vibration or revolution.

After the ion exchanged product is separated by filtration/centrifugal separation, rinsing, surface treatment, drying and grinding are optionally carried out to collect the product. When filtration is difficult, a coagulant may be used in limits not prejudicial to the object of the present invention to improve the filtration operation. The coagulant is, for example, a polymer coagulant such as polyacrylamide. The amount of the polymer coagulant is preferably 0.2% or less. When it is added in an amount of more than 0.2%, the filtration operation is not further improved.

2. Method of manufacturing potassium type silver- and organic acid anion-containing aluminum sulfate hydroxide particles;

The above potassium type silver- and organic acid anion-containing aluminum sulfate hydroxide particles are manufactured from a sulfate such as aluminum sulfate or potassium sulfate, an Al source material, a $SO_4$ source material, a K source material such as potassium hydroxide, an organic acid source material such as oxalic acid and a soluble silver salt such as silver nitrate which is used for an ion exchange reaction as a silver source material by the following method.

For example, after $Al_2(SO_4)_3+K_2SO_4$ (or $KNO_3$)+$H_2C_2O_4$ are fully dissolved in water, potassium hydroxide is added to the resulting solution under agitation. The subsequent operation is carried out in accordance with the method described in the above paragraph 1.

3. Method of manufacturing ammonium type silver- and organic acid anion-containing aluminum sulfate hydroxide particles;

The above ammonium type silver- and organic acid anion-containing aluminum sulfate hydroxide particles are manufactured from a sulfate such as aluminum sulfate or ammonium sulfate, an Al source material, a $SO_4$ source material, a $NH_4$ source material such as ammonium nitrate, an organic acid source material such as oxalic acid and a soluble silver salt such as silver nitrate which is used for an ion exchange reaction as a silver source material by the following method.

For example, after $Al_2(SO_4)_3$, +$K_2SO_4$ (or $KNO_3$)+$H_2C_2O_4$ are fully dissolved in water, an ammonia aqueous solution is added to the resulting solution under agitation. The subsequent operation is carried out in accordance with the method described in the above paragraph 1.

4. Method of manufacturing hydrogen type {($H_3O$)+type} rectangular parallelepiped silver- and organic acid anion-containing aluminum sulfate hydroxide particles;

The above hydrogen type rectangular parallelepiped silver- and organic acid anion-containing aluminum sulfate hydroxide particles represented by the chemical formula $(H_3O)Al_3(SO_4)_2(OH)_6$ can be obtained by mixing together an aqueous solution of aluminum sulfate, a suspension of aluminum hydroxide and an organic acid such as oxalic acid under agitation and subjecting the resulting solution to a hydrothermal treatment at 100 to 250° C., preferably 120 to 200° C. for 0.5 hour or more, preferably 0.5 to 30 hours, more preferably 2 to 20 hours.

Examples of the aluminum hydroxide used include crystalline gibbsite, beyerite, boehmite, pseudoboehmite, diaspore and amorphous aluminum hydroxide. Amorphous aluminum hydroxide is preferred as the particle size uniformity becomes high.

Examples of the amorphous aluminum hydroxide include the dried aluminum hydroxide gel S-100 and FM of Kyowa Chemical Industry. Co., Ltd.

In order to reduce the particle size and improve the particle size uniformity in this method, when a reaction product obtained by mixing together an aqueous solution of aluminum sulfate and a suspension of aluminum hydroxide under agitation is subjected to a hydrothermal treatment not right after the reaction but after it is left or stirred for some time, for example, 0.5 hour or more, preferably 5 hours or more, more preferably 16 hours or more from the reaction, aluminum sulfate hydroxide fine particles having particle size uniformity can be obtained. The subsequent operation is carried out in accordance with the method described in the above paragraph 1.

The silver- and organic acid anion-containing aluminum sulfate hydroxide particles (X-I) of the present invention can be identified by the powder X-ray diffraction method. Since the diffraction pattern of the particles becomes the same as that of the particles before ion exchange if silver is ion exchanged into the particles, the X-ray diffraction pattern may be closely inspected with reference to the chemical analytical values of the particles. If a product containing silver as an impurity such as silver oxide without being ion exchanged into the particles is mixed with a resin, the obtained resin product becomes dark brown and it is impossible to obtain a white resin product which is one of the important objects of the present invention disadvantageously.

In the present invention, some of aluminum (Al) ions which are trivalent cations of the antibacterial agent of the formula (X-I) may be replaced by at least one cation selected from the group consisting of $Zn^{2+}$ and $Ti^{4+}$ and/or some of the monovalent cations B may be replaced by $Ca^{2+}$ in limits not prejudicial to the object of the present invention.

In this case, to prevent a reduction in the transparency of a resin product obtained by mixing the antibacterial agent with a resin, $Zn^{2+}$ and $Ti^{4+}$ may be contained in the antibacterial agent particles in a total molar amount which is preferably ½ or less, preferably ⅓ or less of the molar amount of aluminum, and $Ca^{2+}$ may be contained in the particles in a molar amount which is ½ or less, preferably ⅓ or less of the total molar amount of the monovalent cations (B).

As means of replacing part of aluminum (Al) which is a trivalent cation of the antibacterial agent of the formula (X-I), a salt such as zinc sulfate, titanium sulfate or calcium sulfate containing the metal cation is used at the time of synthesizing the compound of the above formula (X-II) to incorporate the metal cation into the formula (X-II), or a compound containing the metal cation is used to ion exchange the cation into the compound of the formula (X-II) in a solvent, and then silver is ion exchanged into the obtained product by the above method. In this case, as $Zn^{2+}$ and $Ti^{4+}$ are elements having the effect of developing antibacterial properties, they exhibit antibacterial properties even when the relative content of $Ag^{1+}$ in the formula (X-I) is reduced with the result that the discoloration of a resin molded article obtained by mixing the compound of the formula (X-I) containing one of them with a resin is suppressed advantageously. In this sense, replacement by these elements is preferred.

In the present invention, some of, preferably ½ or less of the "y" mols of $(SO_4)_y$ of the antibacterial agent of the formula (X-I) can be replaced by other inorganic acid ion. If the amount replaced is ½ or less, the particle shape and particle size uniformity of the present invention can be maintained without a problem, thereby attaining the object of the present invention. Examples of the inorganic acid ion include $SO_3^{2-}$, $PO_4^{3-}$, $HPO_3^{2-}$, $CO_3^{2-}$, $NO_3^-$, $SiO_4^{4-}$ and $BO_3^{3-}$. In order to replace part of $(SO_4)_y$ of the antibacterial agent of the formula (X-I) by other inorganic acid ion, a salt containing the inorganic acid ion is used in place of aluminum sulfate, sodium sulfate or potassium sulfate during the reaction of the compound of the formula (X-II) to incorporate the inorganic acid ion into the formula (X-II), or a compound containing the inorganic acid ion is used to ion exchange the inorganic acid ion into the compound of the formula (X-II) in a solvent, and then silver is ion exchanged into the obtained product by the above method. The particles may be further dried, baked, surface treated or coated with an acid resistant film to be used as an antibacterial agent or may be mixed with a resin to obtain an antibacterial resin product like the antibacterial agent particles of the formula (X-I).

In the present invention, part of $(OH)_z$ of the antibacterial agent of the formula (X-I) may be replaced by $Cl^-$. The content of $Cl^-$ is 0.1 mol or less, preferably 0.01 mol or less, most preferably 0.001 mol or less in the formula (X-II) of the antibacterial agent to prevent discoloration.

II). Aluminum Sulfate Hydroxide Particles Represented by the Formula (Y-I);

The aluminum sulfate hydroxide particles represented by the above formula (Y-I) are preferably spherical, disk-like or rectangular parallelepiped and uniform in size and shape and have a narrow particle size distribution width.

Particularly preferably, the aluminum sulfate hydroxide particles represented by the formula (Y-I) are spherical, disk-like or rectangular parallelepiped and have a suitable particle size distribution (sharpness Dr) according to their shape. The shapes of the aluminum sulfate hydroxide particles will be described hereinbelow.

(1) Spherical Particles:

A spherical silver-containing aluminum sulfate hydroxide particle antibacterial agent represented by the following formula (Y-I) and having a sharpness $Dr=D_{75}/D_{25}$ of the particle size distribution obtained by dividing the particle diameter $D_{75}$ (on the large particle diameter side) of the 75% value by the particle diameter $D_{25}$ (on the small particle diameter side) of the 25% value of a volume-based cumulative particle diameter measured by the laser diffraction scattering method of 1 to 1.4.

$$[Ag_aB_{b-a}]_b[M_{3-c}Al_c](SO_4)_y(OH)_z \cdot pH_2O \quad (Y\text{-}I)$$

In the formula (Y-I), a, b, c, y, z and p satisfy $0.00001 \leq a<0.5$, $0.8 \leq b \leq 1.35$, $2.9 \leq c \leq 3$, $1.7<y<2.5$, $4<z<7$ and $0 \leq p \leq 5$, respectively, B is at least one monovalent cation selected from the group consisting of $Na^+$, $NH_4^+$, $K^+$ and $H_3O^+$, and M is Ti.

(2) Disk-Like Particles:

A disk-like silver-containing aluminum sulfate hydroxide particle antibacterial agent represented by the following formula (Y-I).

$$[Ag_aB_{b-a}]_b[M_{3-c}Al_c](SO_4)_y(OH)_z \cdot pH_2O \quad (Y\text{-}I)$$

In the formula (Y-I), a, b, c, y, z and p satisfy $0.00001 \leq a<0.5$, $0.8 \leq b \leq 1.35$, $2.5 \leq c<3$, $1.7<y<2.5$, $4<z<7$ and $0 \leq p \leq 5$, respectively, B is at least one monovalent cation selected from the group consisting of $Na^+$, $NH_4^+$, $K^+$ and $H_3O^+$, and M is Zn.

Preferably, the disk-like particles have a sharpness $Dr=D_{75}/D_{25}$ of the particle size distribution obtained by dividing the particle diameter $D_{75}$ (on the large particle diameter side) of the 75% value by the particle diameter $D_{25}$ (on the small particle diameter side) of the 25% value of a volume-based cumulative particle diameter measured by the laser diffraction scattering method of 1 to 1.8.

(3) Rectangular Parallelepiped Particles:

A rectangular parallelepiped silver-containing aluminum sulfate hydroxide particle antibacterial agent represented by the following formula (Y-I).

$$[Ag_aB_{b-a}]_bAl_3(SO_4)_y(OH)_z \cdot pH_2O \quad (Y\text{-}I)$$

In the formula (Y-I), a, b, y, z and p satisfy $0.00001 \leq a<0.5$, $0.8 \leq b \leq 1.35$, $1.7<y<2.5$, $4<z<7$ and $0 \leq p \leq 5$, respectively, and B is $H_3O^+$.

Preferably, the rectangular parallelepiped particles have a sharpness $Dr=D_{75}/D_{25}$ Of the particle size distribution obtained by dividing the particle diameter $D_{75}$ (on the large particle diameter side) of the 75% value by the particle diameter $D_{25}$ (on the small particle diameter side) of the 25% value of a volume-based cumulative particle diameter measured by the laser diffraction scattering method of 1 to 1.8.

The particles of the antibacterial agent (Y-I) of the present invention are spherical, disk-like or rectangular parallelepiped as shown in the SEM photomicrographs of FIGS. 15 to 20, uniform in shape and not agglomerated and have high dispersibility in a resin. Further, when they are mixed with a resin, the agglomeration of the antibacterial agent in the resin does not occur or rarely occurs (high dispersibility), which is one of the factors of exhibiting antibacterial properties with an extremely low content of silver in a resin product obtained by mixing the antibacterial agent with the resin. Unexpectedly high antibacterial activity which cannot be attained by the prior art is obtained from this feature alone.

Aluminum sulfate hydroxide particles represented by the formula (Y-I) which are disk-like or rectangular parallelepiped and uniform in shape are novel as far as the inventors of the present invention know.

One of the indices for specifying the shape of the particle is Wadell's circularity and sphericity which have been used in the field of the powder industry.

Wadell's sphericity "s" is defined as s=(surface area of sphere having the same volume as particle)/(surface area of particle). As "s" is closer to 1, the particle is more spherical.

Wadell's circularity "c" is defined as c=(circumference of the same area as projected area of particle)/(circumference of plane of projection of particle). As "c" is closer to 1, the particle is more circular.

The spherical shape of the particle means that the particle may be shaped like a ball as shown in the SEM photomicrographs of FIGS. 15, 16, 17 and 19 and has a Wadell's sphericity "s" which preferably satisfies $0.95 \leqq s \leqq 1$.

Figure 20:
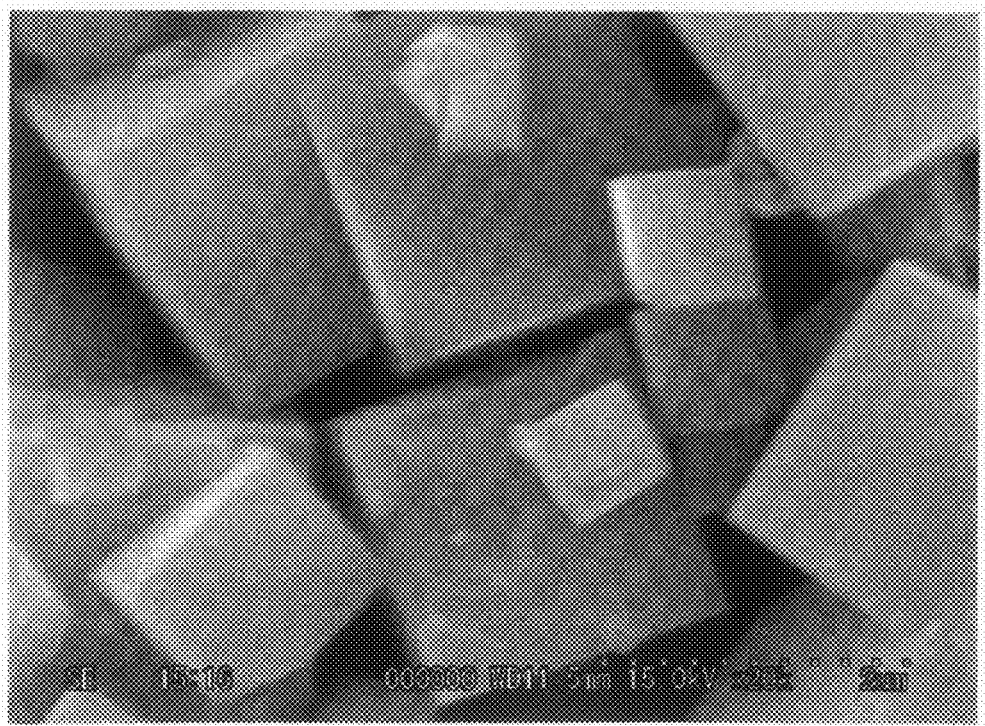
FIG. 20 is a SEM photomicrograph of rectangular parallelepiped particles Y-I-30 in Example Y-I-30.

The rectangular parallelepiped shape of the particle means that the particle may have a shape similar to a hexahedron as shown in the SEM photomicrograph of FIG. 20 or a regular hexahedron and has a Wadell's sphericity "s" which preferably satisfies $0.5 \leqq s \leqq 0.8$.

The disk-like shape of the particle means a flat columnar shape. Preferably, the above Wadell's circularity "c" of a projected image of the particle when seen in the direction of the top surface or the bottom surface satisfies $0.95 \leqq c \leqq 1$ and the thickness/(diameter of circle) ratio "d" satisfies $0.05 \leqq d \leqq 0.6$. The disk-like particles are shown in the SEM photomicrograph of FIG. 18.

A detailed description is subsequently given of silver-containing aluminum sulfate hydroxide particles represented by the above formula (Y-I) of the present invention.

In the formula (Y-I), "a" represents the amount of silver ion exchanged into the antibacterial agent particles. As the numerical value "a" becomes larger, more silver is ion exchanged into the antibacterial agent particles with the result of improved antibacterial properties. When the numerical value "a" becomes too large, silver may separate out or elute from an ion exchanger to become silver oxide, whereby the color of a resin molded article comprising the antibacterial agent may become dark brown and it is not economical. When "a" is 0.5 or more, ion exchange becomes difficult.

When the numerical value "a" becomes too small, the amount of silver ion exchanged into the antibacterial agent particles is small and antibacterial properties are hardly exhibited. Therefore, to balance antibacterial property developing force with the color problem properly, "a" must be limited to a fixed range.

In this sense, silver is suitably used in a resin in such an amount which ensures that "a" in the formula (Y-I) becomes 0.00001 to 0.5, preferably 0.00001 to 0.35, more preferably 0.001 to 0.3.

The word "containing" in the expression "silver-containing aluminum sulfate hydroxide particles" means that the particles contain such a small amount of a compound other than the compound of the formula (Y-I) that a peak derived from the compound other than the compound of the formula (Y-I) does not appear when the particles are measured by the powder X-ray diffraction method. For example, it is conceivable that a trace amount of a silver compound such as silver oxide is carried on the particles.

It is considered that when the particles consist of a solid solution ion exchanged with silver alone, the discoloration of the particles rarely occurs. In this sense, a perfect silver ion exchanger (solid solution) is more preferred than a substance containing the above silver compound carrier.

When it is taken into consideration that "B" has an ion radius relatively close to that of the silver ion and can form an ion exchanger strongly at a wide range and further safety and economy are taken into account, "B" is at least one monovalent cation selected from the group consisting of $Na^+$, $NH_4^+$, $K^+$ and $H_3O^+$.

To suppress a reduction in the whiteness of a resin product (the resin product changes its color from white to dark brown or brown right after molding along the passage of time by the function of light) when the antibacterial agent particles (Y-I) of the present invention are mixed with a resin, the amount of $K^+$ as "B" is preferably as small as possible. That is, the amount of $K^+$ is preferably smaller than ½ of the total molar amount of the monovalent cations as "B".

This discoloration can be prevented by adding 0.000001 to 0.1% of a fluorescent brightener to the resin. When a large amount of $K^+$ is used, the prevention of discoloration becomes difficult without a fluorescent brightener. By adding the fluorescent brightener, a resin product which does not discolor or rarely discolors can be obtained in the present invention.

Examples of the fluorescent brightener include benzohexazole-based fluorescent brighteners such as 2,5-thiophenediyl(5-tert-butyl-1,3-benzohexazole and 4,4'-bis (benzohexazol-2-yl)stilbene, and pyrazoline-based and coumarine-based fluorescent brighteners, out of which fluorescent brighteners registered at FDA (Food & Drag Administration of the U.S.) and the Polyolefin Hygiene Council are preferably used. The fluorescent brightener include benzohexazole-based fluorescent brighteners and 2,5-thiophenediyl(5-tert-butyl-1,3-benzohexazole.

When "b" in the formula (Y-I) is 0.8 to 1.35, preferably 0.9 to 1.25, the antibacterial agent particles of the present invention are readily formed. When "y" in the formula (Y-I) satisfies $1.7 < y < 2.5$, preferably $1.9 < y < 2.4$, the antibacterial agent particles of the present invention are readily formed. When "z" satisfies $4 < z < 7$, preferably $5 < z < 6.5$, the antibacterial agent particles of the present invention are readily formed.

Further, "p" in the formula (Y-I) represents the amount of crystal water and generally satisfies $0 \leqq p \leqq 5$.

To make "p" as close to "0" as possible or make it "0", drying at 350° C. or lower or baking must be carried out additionally. Baking is preferably carried out at 600° C. or lower. When the baking temperature is 500° C. or higher, further 550° C. or higher, particularly 600° C. or higher, a water-soluble aluminum sulfate represented by the following formula may be partially formed and the water resistance of a resin product comprising the same may deteriorate. When the amount of the aluminum sulfate is small, there is no problem with the water resistance.

$$(Ag_aB_{b-a})_b[M_{3-c}Al_c](SO_4)_y$$

When the baking temperature is 500° C. or lower, particularly 450° C. or lower, the water-soluble aluminum sulfate represented by the above formula is not formed and even when this aluminum sulfate is used in a resin product, water resistance does not lower. When the antibacterial agent particles of the present invention are baked at 600° C. or higher, the particle shapes of the antibacterial agent particles may not be maintained.

From the viewpoints of water resistance and shape retention, the baking temperature of the antibacterial agent particles of the present invention is 350 to 600° C., preferably 350 to 550° C., more preferably 350 to 500° C., most preferably 350 to 450° C.

It is preferred to carry out the above drying or baking step in a nitrogen atmosphere from the viewpoint of preventing the discoloration of the antibacterial agent particles and a resin product comprising the antibacterial agent particles. Drying step in vacuum is preferred from the viewpoint of preventing the coloration. When there is no problem in the processing of a resin if "p" is not "0", for example, when the amount of the antibacterial agent is very small or when a resin has a water content which does not cause a problem at the time of processing, a resin composition can be manufactured by mixing the particles of the formula (Y-I) in which p satisfies $0 \leq p \leq 5$, preferably $0 \leq p < 3$ with a resin.

On the other hand, when there is a problem if "p" is not "0" or not close to "0", the particles of the formula (Y-I) in which "p" is "0" or close to "0" obtained by adding a drying or baking step must be used.

For example, in the case of a polyester resin such as PET or PBT, polyamide-based resin, polyurethane-based resin, polycarbonate resin or polyacetal resin, it can be recommended to use the antibacterial agent which is additionally dried or baked under the above condition to make "p" (water content) "0" or close to "0".

A description is subsequently given of the physical properties such as shape, particle diameter, particle size distribution, BET specific surface area and refractive index of the antibacterial agent particles of the present invention.

The antibacterial agent particles of the present invention are spherical, disk-like or rectangular parallelepiped and uniform in shape. Out of these, disk-like or rectangular parallelepiped antibacterial agent particles have been utterly unknown.

Further, the antibacterial agent has a sharpness $Dr=D_{75}/D_{25}$ of the particle size distribution obtained by dividing the particle diameter $D_{75}$ (on the large particle diameter side) of the 75% value by the particle diameter $D_{25}$ (on the small particle diameter side) of the 25% value of a volume-based cumulative particle diameter measured by the laser diffraction scattering method of 1.0 to 1.8, preferably 1.0 to 1.4, more preferably 1.01 to 1.3, most preferably 1.01 to 1.2. When this sharpness Dr is small, the particles can be dispersed into the resin completely without being agglomerated, which is considered as a factor for improving an antibacterial effect. Further, when a filter (screen mesh) is used at the time of kneading and extruding a resin, the filter is not or rarely clogged up with the antibacterial agent advantageously.

For the purpose of providing high antibacterial properties to an antibacterial resin product comprising the antibacterial agent of the present invention, particles having a small average secondary particle diameter are suitably used. In this sense, the average secondary particle diameter of the antibacterial agent particles is 0.1 to 12 μm, preferably 0.1 to 5 μm, more preferably 0.3 to 2 μm. To prevent the filter from being clogged up with the antibacterial agent particles, it can be recommended to reduce the total amount of particles having a particle diameter of 15 μm or more to 0.1% or less, preferably 0.01% or less, more preferably 0% of the total.

It is difficult to manufacture the antibacterial agent particles having an average secondary particle diameter of 0.1 μm or less and even when antibacterial agent particles having an average secondary particle diameter of 12 μm or more are mixed with a resin, the antibacterial properties of the obtained resin composition may not be improved.

The BET specific surface area of the antibacterial agent particles (Y-I) of the present invention is 0.1 to 250 m²/g. To provide high antibacterial properties to the resin composition, antibacterial agent particles having a larger BET specific surface area are advantageous. However, when the particles have a too large BET specific surface area, it may be difficult to charge the particles into a resin and when the particles have a too small BET specific surface area, they may be unable to provide sufficiently high antibacterial properties to the resin composition. In this sense, the BET specific surface area of the antibacterial agent is 0.1 to 250 m²/g, preferably 1 to 250 m²/g, more preferably 3 to 100 m²/g, most preferably 30 to 100 m²/g.

A description is subsequently given of the method of manufacturing the antibacterial agent particles (Y-I) represented by the formula (Y-I) of the present invention.

As the method of manufacturing the antibacterial agent particles (Y-I) of the present invention, spherical, disk-like or rectangular parallelepiped aluminum sulfate hydroxide particles represented by the following formula (Y-II) and having particle size uniformity are first manufactured in accordance with the method described in the specification of JP-A 2005-111733 (filed on Apr. 8, 2005) previously proposed by some of the inventors of the present invention, and some of the monovalent cations of the particles are ion exchanged with silver ions to manufacture the silver-containing aluminum sulfate hydroxide particles of the present invention represented by the formula (Y-I).

Spherical or disk-like aluminum sulfate hydroxide particles represented by the formula (Y-II) can be basically manufactured by the above proposed method.

$$[B]_b[M_{3-c}Al_c](SO_4)_y(OH)_z \cdot pH_2O \qquad (Y\text{-}II)$$

In the formula (Y-II), b, c, y, z and p satisfy $0.8 \leq b \leq 1.35$, $2.5 \leq c < 3$, $1.7 < y < 2.5$, $4 < z < 7$ and $0 \leq p \leq 5$, respectively, B is at least one monovalent cation selected from the group consisting of Na⁺, NH₄⁺, K⁺ and H₃O⁺, and M is Zn or Ti.

To obtain the spherical and disk-like antibacterial agent particles of the present invention, the following four factors, that is, (1) the alkali equivalent ratio (=hydroxide having a monovalent cation/aluminum sulfate), (2) the (sulfate having a monovalent cation)/(aluminum sulfate) molar ratio in the case of spherical particles and the (sulfate having a monovalent cation)/(aluminum sulfate+zinc compound) molar ratio in the case of disk-like particles, (3) the hydrothermal treatment temperature and (4) the hydrothermal treatment time in the following chemical reaction formula (b) are desirably controlled to certain ranges.

In the method of the prior art in which these factors are not controlled to certain ranges, a reaction product obtained by mixing together solutions of aluminum sulfate Al₂(SO₄)₃ and sodium sulfate Na₂SO₄ under agitation is subjected to a hydrothermal treatment represented by the following chemical reaction formula (a). Aluminum sulfate hydroxide particles obtained by this method are agglomerated, and uniformity in the particle size of the particles is not observed at all.

(a) Manufacture of Spherical Particles

Surprisingly, aluminum sulfate hydroxide particles manufactured by adding a certain amount of sodium hydroxide to ensure that the amount of an alkali becomes 3.2 to 4.0 based on the alkali equivalent ratio (=[NaOH]/[Al$_2$(SO$_4$)$_3$]=4), that is, the alkali equivalent ratio becomes 0.78 to 1.2 in the following chemical reaction formula (b) and controlling the above factors (2), (3) and (4) to certain ranges in this method have a D$_{75}$/D$_{25}$ which is an index of particle size uniformity of 1.0 to 1.4 and are spherical, which is utterly unexpected.

Hydrothermal Treatment

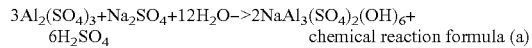
chemical reaction formula (a)

(Agglomerated Particles)
Hydrothermal Treatment

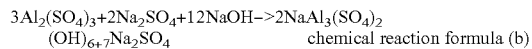
chemical reaction formula (b)

(Spherical Particles Having Uniform in Particle Size)

When the manufacture of the spherical aluminum sulfate hydroxide particles of the present invention is aimed, it is found that in the above chemical reaction formula (b) of aluminum sulfate hydroxide particles manufactured by adding an aqueous solution of alkali hydroxide BOH containing a monovalent cation to a mixed solution of aluminum sulfate Al$^{3+}_2$(SO$_4$)$_3$, a zinc compound and a sulfate B$_2$SO$_4$ having the above monovalent cation and subjecting the resulting solution to a hydrothermal reaction, the amount of the alkali hydroxide added is desirably such that the alkali equivalent ratio becomes 0.60 to 1.0, preferably 0.7 to 0.90, more preferably 0.75 to 0.90.

When the alkali equivalent ratio is lower than 0.6, the spherical aluminum sulfate hydroxide particles having excellent particle size uniformity of the present invention may not be obtained. When the alkali equivalent ratio is higher than 1.1, particularly 1.2, spherical aluminum sulfate hydroxide particles having excellent particle size uniformity may not be obtained and also boehmite which is a type of aluminum hydroxide crystal may be contained in the aluminum sulfate hydroxide particles.

The above (sulfate having a monovalent cation)/(aluminum sulfate) molar ratio is 0.3 to 3.0, preferably 0.6 to 2.5, most preferably 0.6 to 2.0. When the molar ratio is lower than 0.3 or higher than 3.0, the spherical aluminum sulfate hydroxide fine particles having excellent particle size uniformity of the present invention may not be manufactured.

The inventors of the present invention have found that spherical aluminum sulfate hydroxide particles having excellent particle size uniformity can be manufactured by adding a sulfate having a monovalent cation such as potassium sulfate K$_2$SO$_4$ or ammonium sulfate in place of sodium sulfate and a hydroxide having a monovalent cation such as potassium hydroxide or ammonium water in place of sodium hydroxide in the above chemical reaction formula (b).

The inventors of the present invention have also found that spherical aluminum sulfate hydroxide particles having excellent particle size uniformity can be manufactured by adding a titanium compound, preferably titanium sulfate to a mixed solution of aluminum sulfate and a monovalent cation aqueous solution to replace 1/10 or less of the number of mols of Al by Ti in the above chemical formula (b).

(b) Manufacture of Disk-Like Particles

The inventors of the present invention have also found that disk-like aluminum sulfate hydroxide particles having a uniform particle size, that is, a D$_{75}$/D$_{25}$ of 1.0 to 1.8 can be manufactured by adding a certain amount of a zinc compound, preferably zinc oxide or zinc sulfate to a mixed solution of aluminum sulfate and a monovalent cation aqueous solution to replace 1/6 or less of the "c" mols of Al in (Y-II) by Zn in the above chemical reaction formula (b).

The aluminum sulfate hydroxide particles are represented by the above formula (Y-II), and it has been found that when "c" satisfies 2.5≦c<3, preferably 2.5≦c≦2.99, more preferably 2.61≦c≦2.9, the disk-like aluminum sulfate hydroxide particles having excellent particle size uniformity of the present invention can be obtained.

When the manufacture of the disk-like aluminum sulfate hydroxide particles of the present invention is aimed, it has further been found that it is advantageous to set the amount of the above alkali hydroxide added such that the alkali equivalent ratio becomes 0.60 to 1.0, preferably 0.70 to 0.90, more preferably 0.75 to 0.90 in the above chemical reaction formula (b) for obtaining the aluminum sulfate hydroxide particles by adding an aqueous solution of an alkali hydroxide B$^{1+}$OH containing a monovalent cation to a mixed solution of aluminum sulfate Al$^{3+}_2$(SO$_4$)$_3$, a zinc compound and a sulfate B$_2$SO$_4$ having the above monovalent cation to carry out a hydrothermal reaction.

When the above alkali equivalent ratio is lower than 0.6 in the case of disk-like particles, disk-like aluminum sulfate hydroxide particles having excellent particle size uniformity may not be obtained and when the alkali equivalent ratio is higher than 1.0, aluminum sulfate hydroxide particles having excellent particle size uniformity may not be manufactured.

The above hydrothermal treatment temperature is 90 to 250° C., preferably 100 to 250° C., more preferably 120 to 250° C., most preferably 150 to 200° C. when the aluminum sulfate hydroxide particles are spherical and the alkali equivalent ratio is 0.78 to 0.9. When the hydrothermal treatment temperature is 100° C. or lower, particularly 90° C. or lower, the aluminum sulfate hydroxide particles having excellent particle size uniformity of the present invention may not be manufactured. Even when the hydrothermal treatment temperature is 250° C. or higher, the effect of improving particle size uniformity is not obtained and it is not economical. When the alkali equivalent ratio is 0.9 to 1.1, the hydrothermal treatment temperature is 110 to 250° C., preferably 150 to 250° C., more preferably 150 to 200° C. When the hydrothermal treatment temperature is 110° C. or lower, the aluminum sulfate hydroxide particles having excellent particle size uniformity of the present invention may not be manufactured. Even when the hydrothermal treatment temperature is 250° C. or higher, the effect of improving particle size uniformity is not obtained and it is not economical.

The above hydrothermal treatment time is 0.3 to 30 hours, preferably 1 to 20 hours, more preferably 1.5 to 6 hours when the alkali equivalent ratio is 0.78 to 0.9 and 0.5 to 30 hours, preferably 1 to 20 hours, more preferably 1.5 to 6 hours when the alkali equivalent ratio is 0.9 to 1.1.

When the hydrothermal treatment time is 0.3 hour or less or 0.5 hour or less, the aluminum sulfate hydroxide particles having excellent particle size uniformity of the present invention may not be manufactured. Even when the hydrothermal treatment time is 30 hours or more, the effect of improving particle size uniformity is not obtained and it is not economical.

The inventors of the present invention have confirmed that for the manufacture of the spherical or columnar antibacterial agent particles (Y-I) having particle size uniformity of the present invention, it is desired to control the following four factors, i.e., (1) the alkali equivalent ratio (=hydroxide having a monovalent cation/aluminum sulfate) in the above chemical reaction formula (4), (2) the (sulfate having a monovalent cation)/(aluminum sulfate) molar ratio in the case of spherical particles or (sulfate having a monovalent cation)/(aluminum sulfate+zinc oxide) molar ratio in the case of disk-like particles, (3) the hydrothermal treatment temperature and (4) the hydrothermal treatment time to certain ranges.

(c) Manufacture of Rectangular Parallelepiped Particles

The inventors of the present invention have further found the method of manufacturing rectangular parallelepiped antibacterial agents having excellent particle size uniformity.

Unlike the method of manufacturing the above spherical and disk-like particles, rectangular parallelepiped hydrogen type aluminum sulfate hydroxide particles represented by the chemical formula $(H_3O)Al_3(SO_4)_2(OH)_6$ can be obtained by subjecting a reaction product obtained by mixing together an aqueous solution of aluminum sulfate and a suspension of aluminum hydroxide under agitation to a hydrothermal treatment at 100 to 250° C., preferably 120 to 200° C. for 0.5 hour or more, preferably 0.5 to 30 hours, more preferably 2 to 20 hours, and then the antibacterial agent particles of the present invention can be manufactured by ion exchanging monovalent cations with silver ions in accordance with the above method.

The aluminum hydroxide used is preferably amorphous aluminum hydroxide because the effect of making the particles rectangular parallelepiped and the effect of making the particles uniform in size are high. Examples of the amorphous aluminum hydroxide include dry aluminum hydroxide gel S-100 and FM manufactured by Kyowa Chemical Co., Ltd.

To reduce the size of the particles and improve the particle size uniformity of the particles in this method, it is recommended to subject the reaction product obtained by mixing together the aqueous solution of aluminum sulfate and the suspension of aluminum hydroxide under agitation to a hydrothermal treatment not right after the reaction but after a certain time passes from the reaction, for example, after it is left or stirred for 1 hour or more, preferably 1 to 300 hours, more preferably 5 to 200 hours, thereby obtaining aluminum sulfate hydroxide fine particles having excellent particle size uniformity.

The spherical, disk-like and rectangular parallelepiped aluminum sulfate hydroxide particles described above can be represented by the formula (Y-II) as described above.

$$[B]_b[M_{3-c}Al_c](SO_4)_y(OH)_z \cdot pH_2O \quad (Y\text{-}II)$$

The silver-containing aluminum sulfate hydroxide particles of the present invention represented by the formula (Y-I) can be obtained from these spherical, disk-like and rectangular parallelepiped particles by ion exchanging monovalent cations with silver ions.

That is, the inventors of the present invention have developed their studies based on the above findings and have found that the antibacterial agent fine particles having the above specific particle shape and particle size uniformity of the present invention represented by the above formula (Y-I) can be manufactured by first synthesizing aluminum sulfate hydroxide particles represented by the formula (b) containing no silver and bringing the aluminum sulfate hydroxide particles into contact with a solution containing silver such as silver nitrate or silver sulfate in a suspension such as water under agitation to ion exchange silver ions into the aluminum sulfate hydroxide particles.

The ion exchange reaction temperature is 0 to 100° C., preferably 10 to 80° C., most preferably 20 to 80° C. The ion exchange is preferably carried out for 0.1 to 30 hours under shaded light. When the ion exchange temperature is too low or the ion exchange time is too short, the amount of silver ion exchanged may become small. When the ion exchange temperature is too high, the ion exchange time is too long, or ion exchange is not carried out under shaded light, the ion exchanged product may turn brown. Stirring during the ion exchange reaction may be carried out by vibration or revolution.

When filtration, rinsing, surface treatment, drying and grinding are optionally carried out after ion exchange to collect the particles, an antibacterial agent represented by the formula (Y-I) can be obtained. When filtration by putting the particles through a filter is difficult, decantation or centrifugal separation may be employed, or a coagulant may be used in limits not prejudicial to the object of the present invention. Examples of the coagulant include polymer coagulants such as polyacrylamide. The amount of the polymer coagulant is preferably 0.2% or less. When the amount of the coagulant is 0.2% or less, the monodisperse particles of the present invention are not affected and the filtration work is improved.

Meanwhile, strong force does not need to be used to grind the particles as can be understood from SEM photomicrographs. Even when grinding is simply carried out with weak force, silver-containing aluminum sulfate hydroxide particles which are monodisperse or almost monodisperse and not agglomerated are obtained, which is the feature of the present invention.

The silver-containing aluminum sulfate hydroxide particles of the present invention can be identified by the powder X-ray diffraction method.

Since the diffraction pattern of the particles becomes the same as that of the particles before ion exchange if silver is ion exchanged into the particles, the X-ray diffraction pattern may be closely inspected with reference to the chemical analytical values of the particles. If a product containing silver as an impurity such as silver oxide without being ion exchanged into the particles is mixed with a resin, the obtained resin product becomes dark brown and it is impossible to obtain a white resin product which is one of the important objects of the present invention disadvantageously.

In the present invention, ⅕ or less of the "y" mols of $(SO_4)_y$ in the formula (Y-I) can be replaced by other inorganic acid ion. When ¹/₁₀ or less of the "y" mols of $(SO_4)_y$ is replaced, the particle shape and particle size uniformity of the present invention can be maintained without a problem, thereby attaining the object of the present invention. Examples of the other inorganic acid ion include $SO_3^{2+}$, $PO_4^{3-}$, $HPO_3^{2-}$, $CO_3^{2-}$, $NO_3^-$, $SiO_4^{4-}$ and $BO_3^{3-}$. In order to replace part of $(SO_4)_y$ of the antibacterial agent of the formula (Y-I), a compound containing the inorganic acid ion is added to a suspension containing the compound of the formula (Y-II) to carry out ion exchange in a solvent and then silver is ion exchanged into the obtained product by the above method.

The particles obtained by ion exchanging part of the antibacterial agent of the formula (Y-I) with the inorganic acid ion may be dried, baked, surface treated and coated with an acid resistant film to be used as an antibacterial agent or mixed with a resin to obtain an antibacterial resin product like the antibacterial agent particles of the formula (Y-I).

In the present invention, part of $(OH)_z$ of the antibacterial agent of the formula (Y-I) may be replaced by $Cl^-$. However, the content of $Cl^-$ is 0.1 mol or less, preferably 0.01 mol or less, most preferably 0.001 mol or less from the viewpoint of preventing discoloration.

For the manufacture of the silver-containing aluminum sulfate hydroxide particles of the present invention, with a view to obtaining high-purity antibacterial agent particles having low contents of heavy metals such as lead and cadmium specified by the Notice No. 20 of the Ministry of Welfare of the Food Hygiene Act industrially and containing heavy metals such as iron, manganese, chromium, copper and nickel in amounts of 1% or less, preferably 0.1% or less, more preferably 0.01% or less, most preferably 0.001% or less so as to prevent the thermal deterioration (improvement of thermal deterioration resistance) and discoloration of a resin product, it is preferred to use high-purity raw materials and a corrosion resistant material such as Hastelloy steel or stainless SUS-316 steel in a hydrothermal treatment step wherein chemical operation devices are easily corroded out, so as to prevent heavy metal compounds such as manganese, chromium, copper and nickel eluting from the material of the device from being contained in the antibacterial agent particles of the present invention as a solid solution and/or an impurity.

III). Use of Antibacterial Agent of the Present Invention in Resin Composition

In the present invention, an antibacterial resin composition having excellent filter passability at the time of kneading and extrusion, antibacterial properties, dispersibility, whiteness and also antibacterial action retention characteristics after contact with tap water can be provided by mixing 0.001 to 300 parts by weight of the antibacterial agent represented by the above formula (X-I) or (Y-I) with 100 parts by weight of a resin, and a resin product can be formed from the composition. When importance is attached to an additional value, that is, high transparency of the resin product, it can be recommended to mix 0.001 to 10 parts by weight, preferably 0.001 to 2 parts by weight of the antibacterial agent. When the amount of the antibacterial agent is smaller than 0.001 part by weight, satisfactory antibacterial properties may not be obtained and when the amount of the antibacterial agent is larger than 300 parts by weight, depending on the content of silver, it is uneconomical and transparency may lower.

The refractive index of the antibacterial agent of the present invention is about 1.48 to about 1.56 which overlaps or is close to those of many resins. Therefore, even when a large amount of the antibacterial agent of the present invention is mixed with a resin, it does not impair transparency so much. In order to maintain high transparency, it can be recommended to use the antibacterial agent in an amount of 10 parts or less by weight, preferably 2 parts or less by weight.

Although the antibacterial resin product comprising the antibacterial agent particles of the present invention has high acid resistance originally, in order to provide higher acid resistance to the resin product or to prevent the discoloration of the resin product, the surfaces of the antibacterial agent particles of the present invention are treated with at least one acid resistant modifier or discoloration inhibitor selected from the group consisting of silicon compounds, phosphorus compounds, boron compounds, aluminum compounds, zirconium compounds, titanium compounds, zinc compounds and tin compounds to further improve acid resistance or prevent discoloration.

As examples of the acid resistant modifier or the discoloration inhibitor, the silicon compounds include sodium metasilicate, sodium orthosilicate, potassium metasilicate, potassium orthosilicate, water glass, silicic acid and silicone oil; the boron compounds include sodium tetraborate, sodium metaborate, potassium tetraborate, potassium metaborate and boric acid; the aluminum compounds include sodium orthoaluminate, sodium metaaluminate, potassium orthoaluminate, potassium metaaluminate, aluminum chloride, aluminum nitrate, aluminum sulfate and aluminum phosphate; the phosphorus compounds include potassium phosphate, sodium phosphate and phosphoric acid; the zirconium compounds include zirconium phosphate, sodium zirconate, potassium zirconate and zirconic acid; the titanium compounds include titanium chloride, sodium titanate, potassium titanate and titanic acid; the zinc compounds include zinc chloride, zinc nitrate, zinc carbonate, zinc sulfate and zinc acid salts; the tin compounds include sodium stannate and potassium stannate; and the ammonium salts include ammonium sulfate, ammonium nitrate, ammonium phosphate, ammonium carbonate and ammonium acetate.

Since the antibacterial agent particles of the present invention are originally monodisperse particles, they have extremely excellent dispersibility into a resin. In order to further improve the dispersibility, prevent the discoloration of a resin product formed from the particles or suppress a reduction in the mechanical strength when a relatively large amount of the antibacterial agent particles of the present invention is mixed with a resin, the surfaces of the antibacterial agent particles of the present invention may be treated with at least one selected from the group consisting of higher fatty acids, silane-based coupling agents, aluminate-based coupling agents, alcohol phosphates and surfactants.

Examples of the surface treating agent include high fatty acids and salts thereof such as stearic acid, oleic acid, erucic acid, palmitic acid, lauric acid and behenic acid, surfactants such as sulfates of polyethylene ether, amide-bonded sulfates, ester-bonded sulfates, ester-bonded sulfonates, amide-bonded sulfonates, ether-bonded sulfonates, ether-bonded alkyl allyl sulfonates and amide-bonded alkyl allyl sulfonates, sulfates of a higher fatty acid such as stearyl alcohol and oleyl alcohol, acid or alkali metal salts or amine salts of mono- or di-esters of orthophosphoric acid and stearyl alcohol or oleyl alcohol, and mixtures thereof, silane coupling agents such as vinylethoxysilane, vinyl-tolyl(2-methoxyethoxy)silane, γ-methacryloxypropyltrimethoxysilane, γ-aminopropyltrimethoxysilane, N-phenyl-γ-aminopropyltrimethoxysilane, N-β(amionoethyl)γ-aminopropyltrimethoxysilane, N-β(amionoethyl)γ-aminopropyltriethoxysilane, N-phenyl-γ-aminopropyltriethoxysilane, β(3,4-epoxycyclohexyl)ethyltrimethoxysilane and γ-mercaptopropyltrimethoxysilane, titanate coupling agents such as isopropyltriisostearoyl titanate, isopropyltri(aminoethyl)titanate and isopropyltridecylbenzenesulfonyl titanate, and aluminate coupling agents such as acetoalkoxyaluminum diisopropyrate.

In the present invention, the resin to be made antibacterial is not particularly limited and may be a synthetic resin-rubber or natural resin-rubber which is processed to produce resin products such as molded articles, fibers, nonwoven fabrics, coatings, caulking materials and films. Some examples of the resin are given below.

Thermoplastic resins include polyolefin-based resins such as olefin (α-olefin) polymers and copolymers having 2 to 12 carbon atoms including polypropylene, ethylene-propylene copolymer, high-density polyethylene, low-density polyethylene, super high molecular weight polyethylene, linear low-density polyethylene, polybutene and poly-4-methyl-penetene-1, copolymers of one of these olefins and a diene, ethylene-vinyl acetate copolymer, ethylene-acrylate copolymer and TPO (thermoplastic polyolefin) resin; styrene-based resins such as polyethylene oxide resin, polystyrene, ABS (acrylonitrile butadiene styrene) resin, AAS (acrylonitrile acryl styrene) resin, AS (acrylonitrile styrene) resin, AES (acrylonitrile EPDM styrene) resin, MBS (methyl methacrylate butadiene styrene) resin and polyparamethyl styrene resin; polyamide-based resins such as ACS (acrylonitrile chlorinated polyethylene styrene) resin, vinyl acetate resin, vinyl propionate resin, phenoxy resin, ionomer resin, polyacetal resin, nylon 6 and nylon 66; polyester-based resins such as polyethylene terephthalate and polybutylene terephthalate; polyamide-imide resin, polysulfone resin, polyarylate resin, polyether imide resin, polyether ketone resin, polyphenylene ether resin, polyphenylene sulfide resin, methacrylic resin, cellulose resin, polycarbonate resin, fluororesin, polyurethane resin, silicone resin, polyvinyl ether resin, polyvinyl formal resin, polyvinyl butyral resin, polyvinyl alcohol resin and isobutylene-maleic anhydride copolymer resin, resins having chlorine in the molecular structure such as polyvinyl chloride resin, ethylene-vinyl chloride copolymer resin, ethylene-vinyl acetate copolymer resin, chlorinated vinyl chloride resin, chlorinated polyethylene, chlorinated polypropylene, coumarone resin, ketone resin, polyvinylidene chloride, polyvinyl dichloride resin and chlorinated polyethers, acetate plastics, cellulose acetate, celluloid, liquid crystal polymer and water absorptive resins.

Thermosetting resins include epoxy resin, phenolic resin, melamine resin, unsaturated polyester resin, alkyd resin, guanamine resin, polyimide resin, urea resin, silicone resin, phenol formaldehyde resin, melamine formaldehyde resin, polyparabenzoic acid resin, polyurethane resin, maleic acid resin, urea resin, furan resin, xylene resin and diallyl phthalate resin.

Rubbers include EPDM (ethylene propylene diene copolymer rubber), EPM (ethylene propylene copolymer rubber), butyl rubber, isoprene rubber, SBR (styrene butadiene rubber), NIR (nitrile isoprene rubber), NBR (nitrile butadiene rubber), urethane rubber, chloroprene rubber, hydrogenated nitrile rubber, polyether-based rubber, ethylene tetrafluoride-propylene rubber, chlorosulfonated rubber, butadiene rubber, acrylic rubber, chlorinated polyethylene, epichlorohydrin rubber, propylene oxide rubber, ethylene-acrylic rubber, norbornene rubber, polysulfide rubber, fluorine rubber, silicone rubber and natural rubber.

These resins and rubbers may be used alone or in combination. When more than one resin and more than one rubber are used, they may be polymer alloyed, blended or molded into a laminate. These synthetic resins are not limited by the manufacturing method. As for a polymerization catalyst for polyolefins, for example, Ziegler, Ziegler Natta, Friedel Crafts, metallocene or Phillips method may be employed.

Additives, reinforcements and fillers which are generally used may be mixed with the antibacterial resin composition of the present invention in limits not prejudicial to the object of the present invention. Some of them are given below.

They are an antioxidant, ultraviolet light absorber, optical stabilizer, thermal stabilizer, metal inactivating agent, plasticizer, antistatic agent, flame retardant, curing agent, curing accelerator, age resistor, peptizer, adhesion providing agent, perfume, lubricant, colorant, nucleating agent, foaming agent, deodorizer and polymer alloy compatibilizing agent.

As the method of obtaining the antibacterial resin composition of the present invention, which is not particularly limited, the above resin and rubber and the bacterial agent particles of the present invention are mixed and kneaded together as uniformly as possible by using a device such as a double-screw extruder, pressure kneader, open roll or Banbury mixer, and the resulting kneaded product is formed into a pellet or powder by using a device such as a pelletizer or mill to obtain the resin composition, or the antibacterial agent particles of the present invention are mixed with a solution of the above resin and rubber dissolved in a solvent.

As the method of obtaining a molded article of the antibacterial resin composition of the present invention, which is not particularly limited, the antibacterial resin composition obtained by the above method is directly formed into a resin product such as a molded article, a master batch comprising a large amount of the resin composition is diluted to a concentration to be used for the final resin product and the diluted composition is formed into an antibacterial resin product by using an injection molding machine, extrusion molding machine, blow molding machine, calender molding machine, injection molding machine or laminate molding machine, or a mixture of the antibacterial agent particles and the resin is directly injected into the above machine to be directly injection molded or extrusion molded.

The shape, size, thickness, length and use of the obtained molded article are not particularly limited. The molded article may be shaped like a plate, bottle, ball, disk, sheet or wire sheath, or a foam or laminate and can be advantageously used in fields which require antibacterial properties, such as products for use in kitchens, bathrooms and toilets, medical supplies and the blowout hole of an air-conditioner.

As the method of obtaining the antibacterial film of the present invention which is not particularly limited, an antibacterial resin composition obtained by the above method is manufactured from a resin suitable for the manufacture of a film, and a film can be obtained from the composition by an inflation, T die, calendar or casting method and may be further stretched. The antibacterial agent particles of the present invention may be used as an antibacterial agent only in a layer which must be antibacterial of a laminate film consisting of two or more layers and obtained by coextrusion, which is very economical.

The shape, size and use of the obtained film are not particularly limited. The film may be used in fields which require antibacterial properties to keep fresh such as a film for packing foods such as vegetables, confectionery and dried fish and meat.

As the method of manufacturing the fiber of the present invention which is not particularly limited, a resin composition which can be spun into a fiber out of the resin compositions is used, spun by conventionally known melt extrusion, dry spinning or wet spinning, further stretched or twisted optionally, and/or mixed with a natural fiber such as cotton, wool or hemp to obtain a product. The use of the obtained fiber is not particularly limited and the fiber can be used in fields which require antibacterial properties such as carpets, clothes, towels, napkins, handkerchiefs, globes, socks, hats and mufflers.

Examples of the fiber include polypropylene, polyethylene, polyamide (nylon), aramide, acrylic, polyurethane, fluorine, polyclar, polyester, polyvinyl chloride, vinylon, vinylidene, acetate, triacetate, rayon, cupra, noboroid, promix, polyacetal, polynosic and plastic optical fibers.

The method of manufacturing the antibacterial nonwoven fabric of the present invention is not particularly limited and a conventional known method may be employed.

For example, papermaking web, random web, parallel web, cross laid web, thread crossing web, tow expanding web, short fiber web, filament web, microfiber web and split film web methods may be employed. Since antibacterial nonwoven fabrics obtained by these methods have antibacterial properties, are light in weight and have excellent properties such as gas permeability and shrinkproofing properties, they can be used in fields which require antibacterial properties such as sanitary items, the hair cloths and linings of clothes, and the foundations of vinyl leather and artificial leather.

The method of manufacturing the antibacterial coating of the present invention on an industrial scale is not particularly limited and conventionally known methods may be employed. The silver- and organic acid anion-containing aluminum sulfate hydroxide particle antibacterial agent of the present invention is mixed in the step of mixing a pigment, vehicle, weather resisting agent, solvent, co-solvent, diluent and plasticizer, kneaded with them optionally and put through a sieve to obtain a product. For private use at home, a commercially available coating may be mixed with the antibacterial agent particles of the present invention before use. When the antibacterial coating of the present invention is used at hospitals, homes for the aged, schools and restaurants, damage from bacteria such as *Escherichia coli* and *Staphylococcus aureus* can be prevented to attain the object of the present invention. Examples of the coating include synthetic resin coatings (alkyd, aminoalkyd, epoxy, fluorine, urethane, vinyl acetate, acrylic esters, unsaturated polyester, phenolic, guanamine, butyral, styrene butadiene, styrene, vinyl chloride, vinylidene chloride and chlorinated rubber-based coatings, rust preventing paints, powder coatings, electric insulating coatings), cellulose coatings, rubber-based coatings, water-soluble synthetic resin coatings (water-soluble alkyd, water-soluble epoxy, water-soluble polybutadiene, water-soluble melamine, water-soluble urea, water-soluble phenolic and water-soluble acrylic coatings, etc.), ethyl alcohol coatings and oily coatings.

The method of obtaining the antibacterial caulking material of the present invention is not particularly limited. For instance, an organopolysiloxane and a ketoxisiminolane-based adhesion accelerator such as γ-aminopropyl bis(methylethylketoxyamino)methoxysilane as basic components of a caulking material are mixed together, a tetrafunctional or trifunctional silane crosslinking agent and a thickener such as silica aerosol and optimally a catalyst for promoting a reaction between a polymer and a crosslinking agent, such as an organic tin carboxylate, and further an antioxidant, ultraviolet light absorber and plasticizer are added to the mixture together with the antibacterial agent particles of the present invention to obtain an antibacterial caulking material in accordance with a conventionally known method.

IV). Use of the Antibacterial Agent of the Present Invention for Purposes Other than the Above Purposes III)

The antibacterial agents of the formula (X-I) and (Y-I) of the present invention can provide valuable products as molded articles when they are mixed with a resin. Meanwhile, the antibacterial agents of the present invention may be used in application fields other than resins, making use of their dispersibility, whiteness, particle shape uniformity and particle size uniformity.

That is, they can be also used in antibacterial paper, agricultural chemicals and cosmetics, making use of their antibacterial properties. Since the antibacterial agents of the present invention are safe for the human body and do not give a stimulus to the human body when they come into contact with the human body, they can be used as an antibacterial agent and antifungal agent in products for use in the kitchens, bathrooms and toilets of housings where people live. They can be directly sprayed over vegetables and fruits as an agricultural chemical. Further, they can be advantageously used in cosmetics.

Methods of measuring the physical properties of an antibacterial agent composed of the antibacterial agent particles of the present invention, an antibacterial resin composition comprising the antibacterial agent particles and molded articles formed from the antibacterial resin composition are shown below.

Method of measuring the properties of a silver- and organic acid anion-containing aluminum sulfate hydroxide particle antibacterial agent;

A laser diffraction scattering method is now most widely used for the measurement of the average secondary particle diameter and particle size distribution of fine particles. The laser diffraction scattering method was used for the measurement of these properties in the present invention.

(1) average secondary particle diameter: measured by using the LA-910 particle size distribution measuring instrument (laser diffraction scattering method) of Horiba Ltd.

(2) sharpness of particle size distribution $Dr=D_{75}/D_{25}$

The sharpness of a particle size distribution obtained by dividing the particle diameter $D_{75}$ (on the large particle diameter side) of the 75% value by the particle diameter $D_{25}$ (on the small particle diameter side) of the 25% value of a volume-based cumulative particle size distribution curve measured by the laser diffraction scattering method using the LA-910 particle size distribution measuring instrument of Horiba Ltd. was defined as $Dr=D_{75}/D_{25}$. As the value of Dr becomes smaller, the sharpness of a particle size distribution is observed; which means uniformity in particle size.

The particle diameter of a spherical particle was evaluated by combining $D_{75}/D_{25}$ measured by the laser diffraction scattering method and the method of measuring a particle size distribution from a SEM photomicrograph below. In this case, the value of $D_{75}/D_{25}$ measured by the laser diffraction scattering method was almost equal to the value of $D_{75}/D_{25}$ measured from the SEM photomicrograph at an error range of about −10 to +10%. Therefore, $D_{75}/D_{25}$ measured by the laser diffraction scattering method was adopted in the present invention.

Method of Measuring a Particle Size Distribution from an Electron Photomicrograph (SEM Photomicrograph) (in the Case of Spherical Particles);

The long diameters and short diameters of all the spherical particles (50 to several hundreds of particles) observed in one SEM photomicrograph were measured with vernier calipers down to 1/50 mm to obtain the average value of the long diameters and the short diameters as the particle diameter of each spherical particle (μm) and particle diameters corresponding to $D_{75}$% and $D_{25}$% of the cumulative particle diameter from that value so as to calculate $Dr=D_{75}/D_{25}$.

(3) BET specific surface area; measured by using the Multisorb-12 12-specimen full automatic surface measuring instrument of Yuasa Ionics Co., Ltd.

(4) particle shape; Observed through a scanning electron microscope (SEM photomicrograph).

The relationships between the antibacterial agent particles of Examples and Comparative Examples and the figures (photomicrographs) of particle shapes are given below.

FIG. 1: spherical particles having a smooth surface (particles A1)

Figure 2:
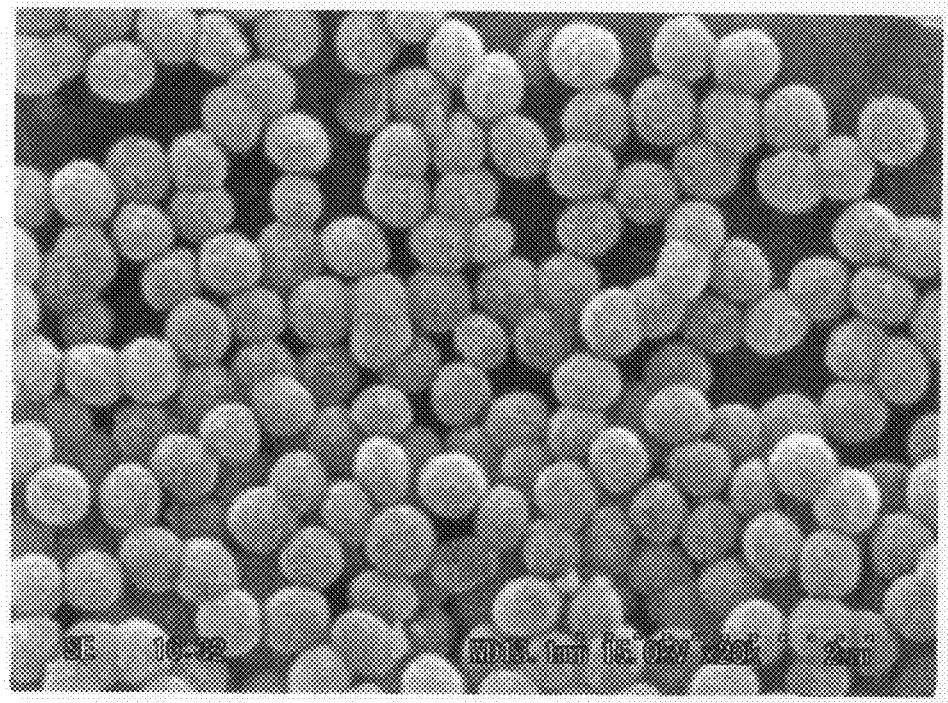
FIG. 2 is a SEM photomicrograph of spherical particles A20 in Example X-I-20.

FIG. 2: spherical particles having small grains on the surface (particles A20)

Figure 3:
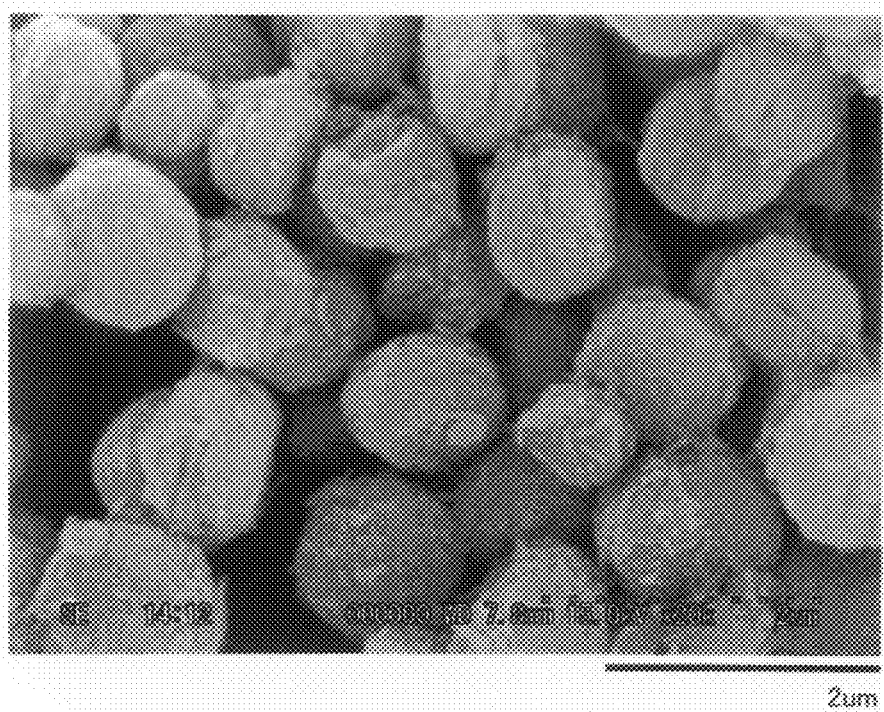
FIG. 3 is a SEM photomicrograph of spherical particles A21 in Example X-I-21.

FIG. 3: spherical particles having a rough surface and wrinkles (scratches and cracks) (particles A21)

Figure 4:
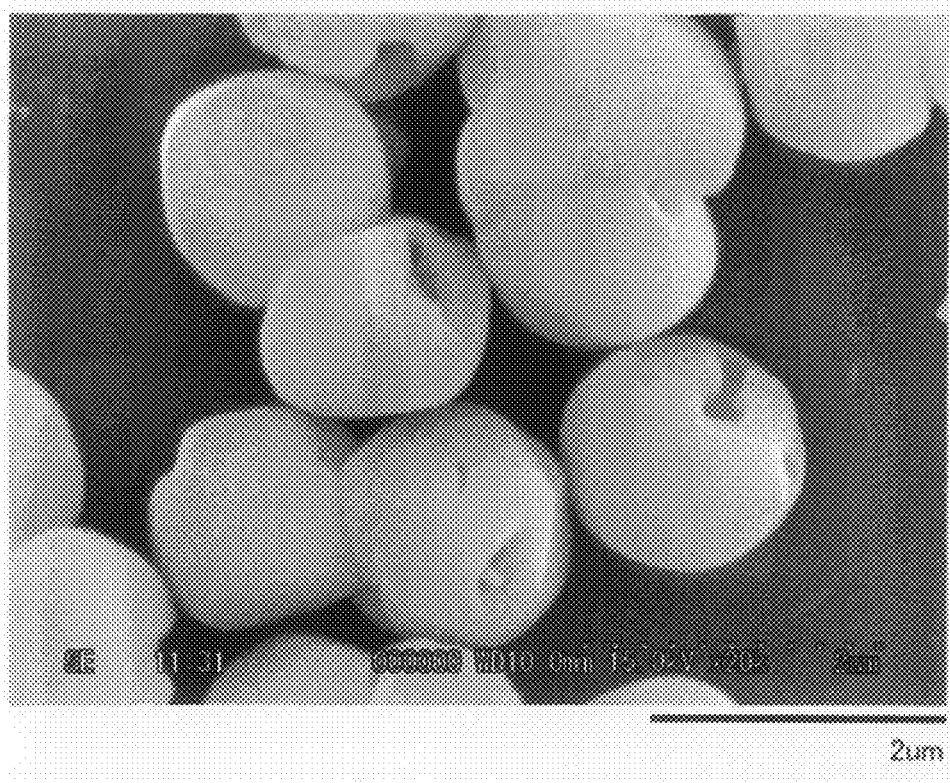
FIG. 4 is a SEM photomicrograph of spherical particles A22 in Example X-I-22.

FIG. 4: spherical particles having holes (unevenness) (particles A22)

Figure 5:
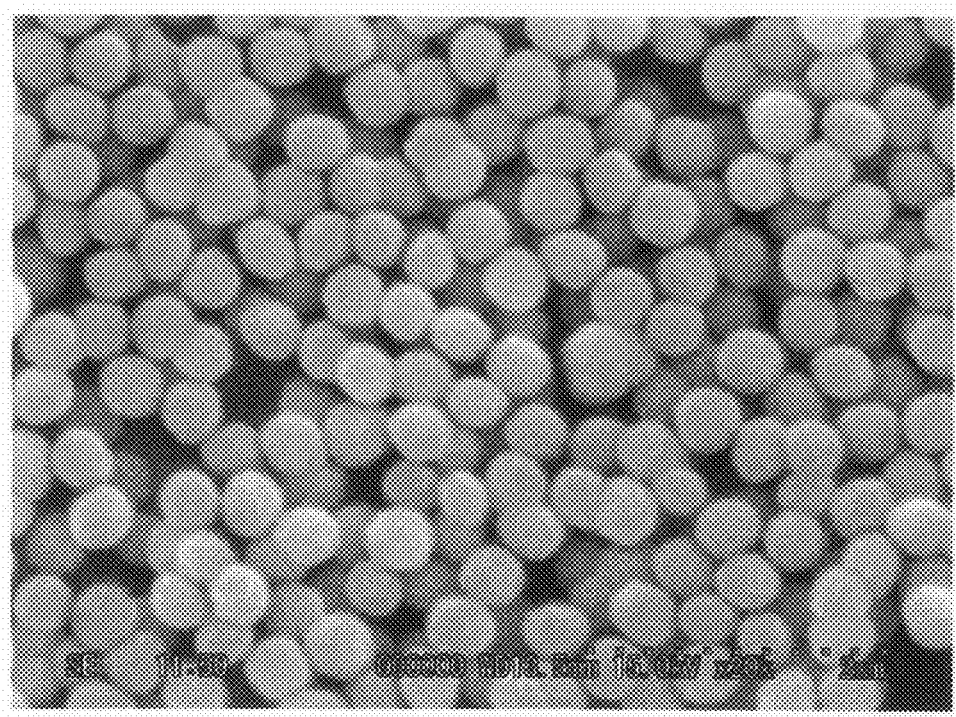
FIG. 5 is a SEM photomicrograph of spherical particles A30 in Example X-I-30.

FIG. 5: spherical particles having a smooth surface and more linear portions than those of FIG. 1 (particles A30)

Figure 6:
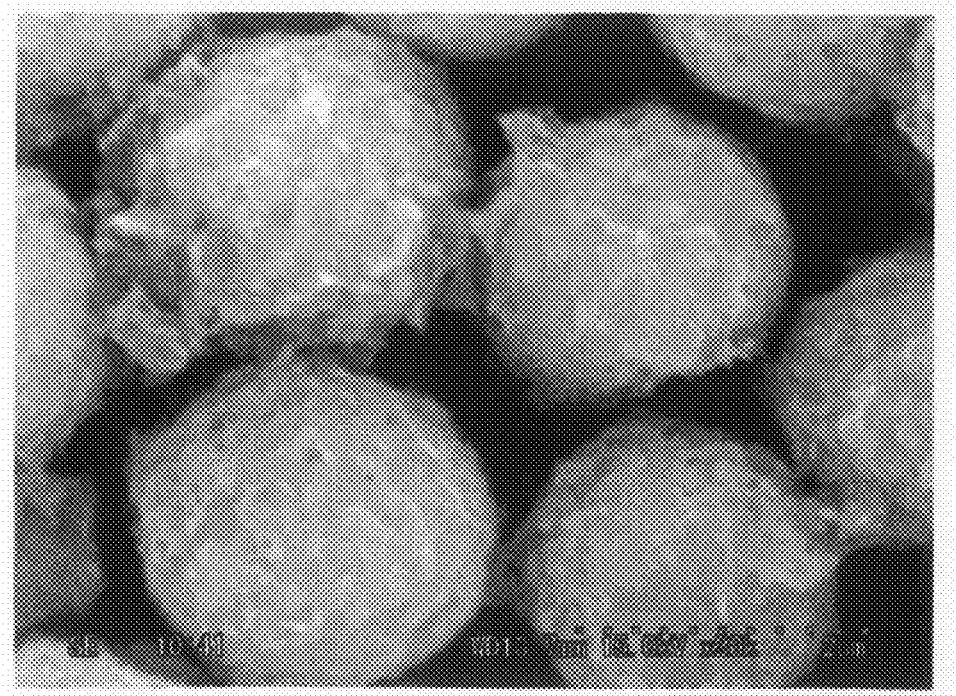
FIG. 6 is a SEM photomicrograph of spherical particles A31 in Example X-I-31.

FIG. 6: spherical particles having a rough surface and wrinkles (particles A31)

FIG. 7: disk-like particles (particles B1-1)

FIG. 8: paired particles (hamburger-like particles) (particles C1)

FIG. 9: rice grain-like particles (particles D1)

FIG. 10: rectangular parallelepiped particles (particles E1)

FIG. 11: hexagonal plate-like particles (particles F1)

FIG. 12: octahedral particles (particles G1)

FIG. 13: columnar (cask-like) particles (particles H1)

FIG. 14: agglomerated particles having a rough surface which look as if they were stretched (particles V1)

Figure 15:
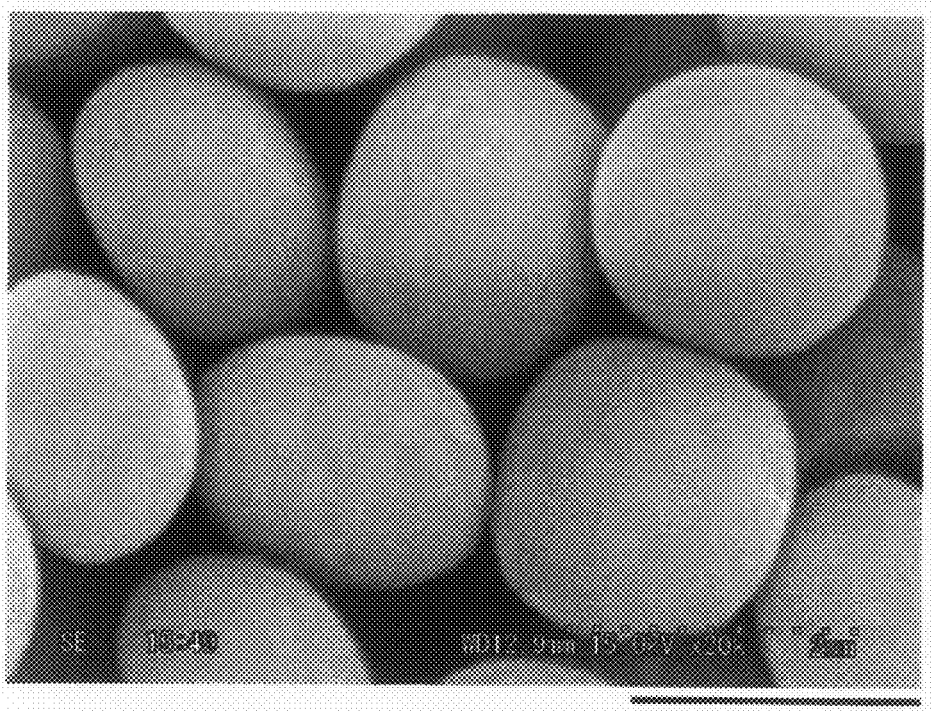
FIG. 15 is a SEM photomicrograph of spherical particles Y-A-1-1 in Example Y-I-1-1.

FIG. 15: spherical particles having a smooth surface (particles Y-A-1)

Figure 16:
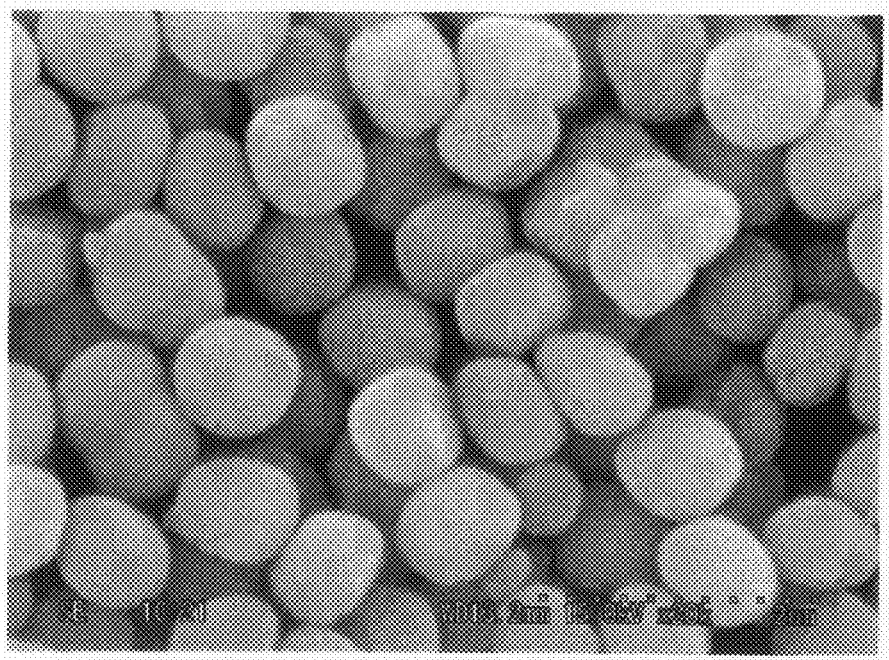
FIG. 16 is a SEM photomicrograph of spherical particles Y-A-4 in Example Y-I-4.

FIG. 16: spherical particles having a cracked surface and a partially broken surface (particles Y-A-4)

Figure 17:
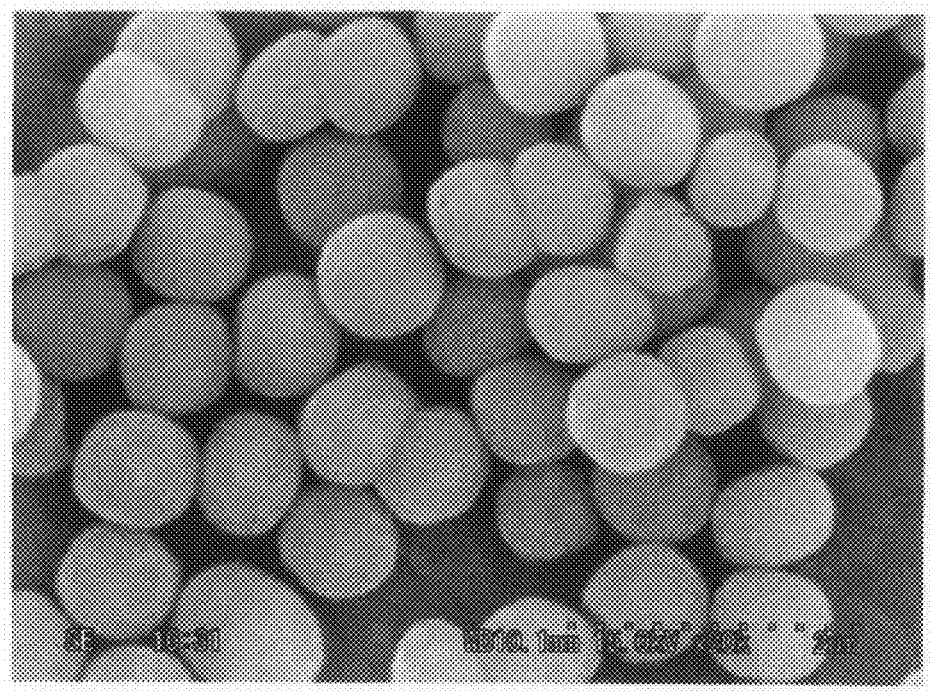
FIG. 17 is a SEM photomicrograph of spherical particles Y-A-5 in Example Y-I-5.

FIG. 17: spherical particles having a cracked surface (Y-A-5)

Figure 18:
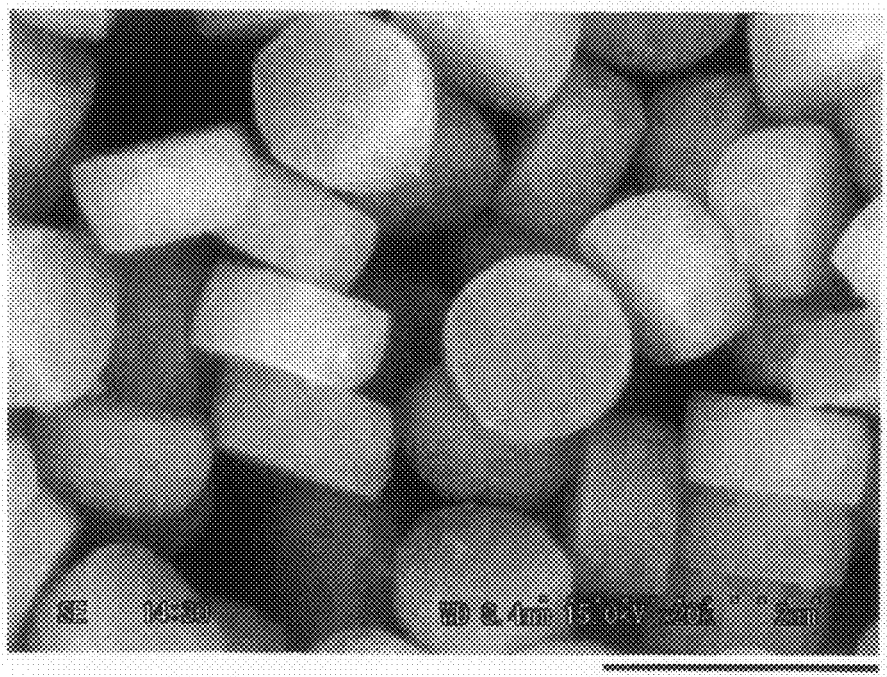
FIG. 18 is a SEM photomicrograph of disk-like particles Y-A-19 in Example Y-I-19.

FIG. 18: disk-like particles (particles Y-A-19)

Figure 19:
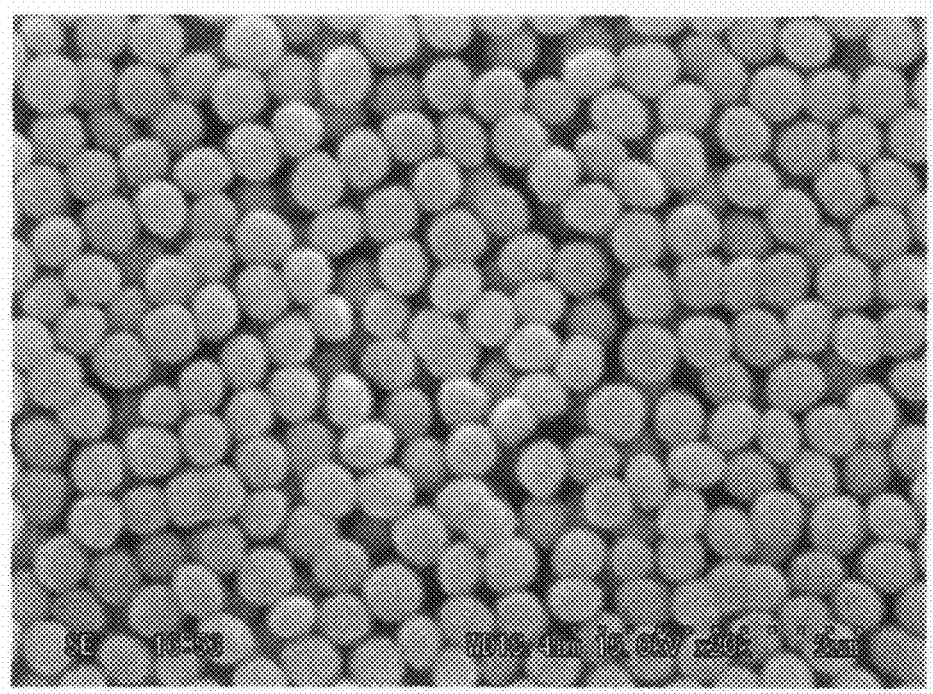
FIG. 19 is a SEM photomicrograph of spherical particles Y-A-18 in Example Y-I-18.

FIG. 19: spherical particles (particles Y-A-18)

FIG. 20 rectangular parallelepiped particles (particles Y-A-30)

Figure 21:
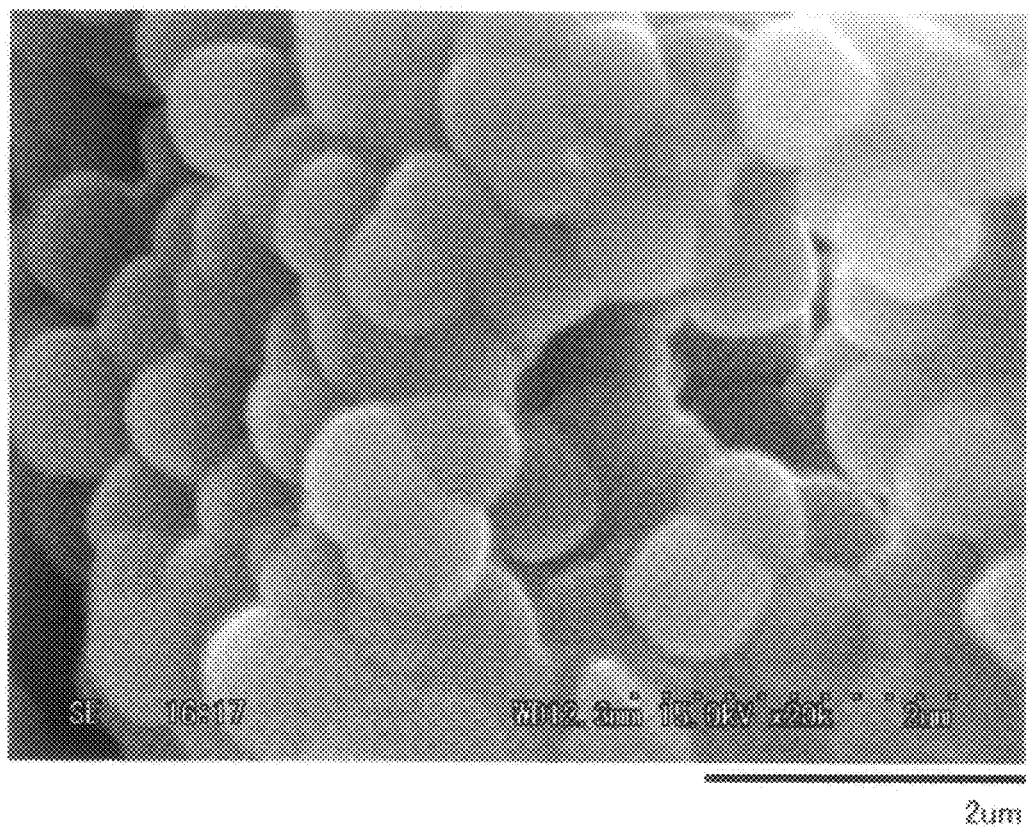
FIG. 21 is a SEM photomicrograph of agglomerated particles Y-V-1 in Comparative Example Y-I-1.

FIG. 21: massive agglomerate of a large number of spherical particles (particles Y-V-1)

(5) formation of ion exchanger; The existence of a diffraction patterns of silver-containing aluminum sulfate hydroxide particles (X-I) and (Y-I) and other diffraction pattern was checked by a powder X-ray diffraction method.

(6) content of organic acid; The silver- and organic acid anion-containing aluminum sulfate hydroxide particles were baked at 1,000° C. to generate $CO_2$ which was collected and measured in accordance with JIS R 9101 to calculate the content of carbon and the content of an organic acid from the above content.

Method of measuring an antibacterial resin composition, resin molded articles and resin products such as films, fibers, coatings and caulking materials:

(7) Antibacterial Property Testing Method

E. coli NBRC 3972 was used and S. aureus NBRC 12732 was used in the following tests (a) to (e). In Tables-7 to −17 showing the results of the antibacterial property test, "cfu" stands for colony forming unit. "Cfu/ml" represents the number of colony forming units per 1 ml and the antibacterial properties are higher as the value of "cfu/ml" becomes smaller.

(a) molded plates; JIS-Z 2801 (year 2000 version) test piece size; 50 mm×50 mm×2 mm
(b) fibers, nonwoven fabrics; JIS-L 1902 (year 2002 version)
(c) coatings; A coating is applied to a test piece composed of an iron plate measuring 50 mm×50 mm×2 mm (made of JIS G 3101 SS400) to a thickness of about 0.1 mm and measured by the above method (a).
(d) films; JIS-Z 2801 (year 2000 version)
(e) caulking materials; A caulking material was caulked on a test piece composed of an iron plate measuring 50 mm×50 mm×2 mm (made of JIS G 3101 SS400) to a thickness of about 1 mm and measured by the above method (a).
(8) transparency; The haze value H of a 2 mm-thick plate or a 50 μm-thick film was measured with the Automatic Haze Meter Optical Unit TC-HIIIDP of Tokyo Densyoku Co., Ltd. and expressed in % based on the following expression.

$$H=\{h_1-(h_2-h_1)\}\times 100/h_1\%$$

wherein $h_1$ is the haze value of a resin molded article or film obtained without adding an antibacterial agent, and $h_2$ is the haze value of a resin molded article or film obtained by adding an antibacterial agent.

As H is closer to 100%, transparency closer to that of an antibacterial agent non-added product is maintained.

(9) whiteness; It was measured visually how much a sample such as a molded article, film, fiber or nonwoven fabric was discolored when it was left in a room on a northern side without the direct rays of the sun for 60 days.

(10) Antibacterial Action Retention Characteristics after Contact with Tap Water The above test material was immersed in 1,000 ml of tap water at 90° C. or 70° C. for 120 hours and fully rinsed with tap water to be measured by the above methods (a) to (e) in the above paragraph (7). A metal net made of stainless steel SUS-304 was used as a weight to immerse a test piece having a specific gravity of 1 or less forcedly. The reason why the tap water was heated at 90° C. or 70° C. is that the antibacterial action retention characteristics of the test piece after its contact with tap water are observed for a short time. This is a promotion test for testing antibacterial action retention characteristics after contact with tap water at normal temperature.

(11) Test of Filter Passability at the Time of Kneading and Extrusion (Measurement of the Pressure of an Extruder)

Filters (screen mesh) were placed in front of the breaker plate of a 30 mm-diameter double-screw kneading extruder (screw diameter of 30 mm) of Plastic Kohgaku Kenkyusho Co., Ltd. when seen from the flow direction of a resin. A 50-mesh filter was placed on the breaker plate side, a 80-mesh filter was placed at the center and a 100-mesh filter was placed on a hopper side. In this state, the machine was operated at a screw revolution of 170 rpm and a delivery rate of 10 kg/hr for 2 hours and then for 24 hours, and its pressure was measured with a pressure meter installed before the filters.

The pressure rises fast when a large number of coarse particles unable to pass through the filter clog up the filter, which means that filter passability is low. In this case, the filter must be exchanged for new one quickly, causing an industrial problem.

In this test, when the pressure is 200 kg/cm$^2$ or more, the machine is almost broken, when the pressure is 150 k/cm$^2$ or more, a too much load is applied to the machine and the machine will malfunction without exchanging the filters, when the pressure becomes 100 kg/cm$^2$, new filters must be prepared to be exchanged for the filters, and when the pressure is 100 kg/cm$^2$ or less, the machine can be operated without a problem.

If the pressure goes up to 150 kg/cm$^2$ 24 hours after the start of the machine, the filters may be exchanged once a day, which is barely of industrial significance somehow.

This measurement was made at an antibacterial agent concentration of 5 wt % based on 100 wt % of the total of 95 wt % of a resin and 5 wt % of the antibacterial agent. This measurement was made separately under a blending condition different from the antibacterial agent concentration on the left side of the vertical double lines shown in Tables-7 to -9. Other conditions at the time of kneading and extrusion were the same as those on the left side of the vertical double lines.

As described above, when an antibacterial agent composed of silver- and organic acid anion-containing aluminum sulfate hydroxide particles of the present invention is used in a resin, it is possible to provide an antibacterial resin composition which is excellent in all of dispersibility, transparency, whiteness, antibacterial properties, especially antibacterial action retention characteristics after contact with tap water and filter passability at the time of kneading and extrusion, antibacterial resin molded articles formed from the resin composition, and antibacterial resin products such as antibacterial films, antibacterial fibers, antibacterial nonwoven fabrics, antibacterial coatings and antibacterial caulking materials.

Out of these, the long-term retention of antibacterial action after contact with tap water cannot be attained by the prior art and it is therefore possible to maintain antibacterial properties for a long time even in places where tap water is always used, such as kitchens, bathrooms and toilets. That is, it is a big outcome of the present invention that it can provide a novel technology for providing an antibacterial agent which retains its antibacterial properties for a long time even under the above condition, a method of manufacturing the antibacterial agent, an antibacterial resin composition and antibacterial resin products formed from the composition.

Another big outcome of the present invention is that it solves a problem with a technology which is generally carried out in a pre-stage for obtaining an antibacterial resin product, that is, a problem that the machine cannot be operated for a long time and the filters must be exchanged in a short period of time due to low filter passability (extruder pressure) at the time of kneading and extruding a resin when a master batch (MB) is manufactured with a resin kneading extruder by kneading together a resin and an antibacterial agent.

Describing this outcome more specifically, filter passability at the time of kneading and extruding a resin is improved by the present invention, the machine can be operated for a longer time, and the frequency of exchanging the filters becomes low, thereby making it possible to cut the amounts of a resin and auxiliary materials such as additives and fillers to be blended with the resin, water, energy, power, labor and time and further to provide an antibacterial resin composition and antibacterial resin products at a lower cost, which is of extremely great industrial value.

EXAMPLES

The method of manufacturing antibacterial agent particles represented by the formula (X-I) of the present invention and the use of the particles will be first described based on Examples.

In the formulas of the following examples, the numbers specified in right bottom part of [ ] in the formula correspond to the total mole of the element, and when the numerical value of "b" in the formula (X-I) is "1", "1" is omitted.

Manufacture of silver- and organic acid anion-containing aluminum sulfate hydroxide particle antibacterial agent; Examples X-I-1 to X-I-47 and Comparative Examples X-I-1 to X-I-9 (manufacture of particles A, B, C, D, E, F, G and H)
Manufacture of Spherical Particles (Particles A); Examples X-I-1 to X-I-31

Example X-I-1

Manufacture of $[Ag_{0.1}(NH_4)_{0.9}]Al_3(C_2O_4)_{0.1}(SO_4)_{1.9}(OH)_6 \cdot 0.5H_2O$ Particles A1 were obtained from the following raw materials by the following synthesizing method.
Raw Materials Used

| | |
|---|---|
| Ammonium sulfate | 264.28 g = 2 mol |
| Oxalic acid $(H_2C_2O_4 \cdot 2H_2O)$ | 38 g = 0.3 mol |
| Aluminum sulfate having a concentration of 1.04 mol/l | 1923 ml = 2.0 mol |
| Ammonia aqueous solution having a concentration of 9.0 mol/l | 894.5 ml = 8.05 mol |

Synthesizing Method 264.28 g of ammonium sulfate $(NH_4)_2SO_4$ was dissolved in 4.0 liters of ion exchange water.

38 g of oxalic acid $(H_2C_2O_4 \cdot 2H_2O)$ was dissolved in 1.0 liter of ion exchange water.

The above aqueous solution of oxalic acid and the above aqueous solution of aluminum sulfate $Al_2(SO_4)_3$ were added to the aqueous solution of ammonium sulfate $(NH_4)_2SO_4$ under agitation to prepare a mixed acid aqueous solution. The mixed acid aqueous solution was heated at 50° C. or lower while it was fully stirred (to dissolve the precipitated crystals), and then 894.5 ml of the above ammonia aqueous solution was added to the mixed acid aqueous solution over 25 minutes to prepare a slurry of an ammonium type organic acid anion-containing aluminum sulfate hydroxide particle precipitate. The slurry was further subjected to a hydrothermal treatment at 100° C. for 1 hour. The treated precipitate was filtered, rinsed, dried and ground to obtain a powder sample. 100 g of the sample was collected, suspended in 600 ml of an aqueous solution of silver sulfate having a concentration of 0.025 mol/l and stirred to carry out ion exchange between ammonium ions and silver ions under shaded light at 30° C. for 8 hours.

The sample after ion exchange was filtered, rinsed, dried (150° C.×6 hours) and ground. Particles A1 were obtained through these steps. The results are shown in Table-1.

Example X-I-2

Manufacture of $[Ag_{0.1}(NH_4)_{0.9}]Al_3(C_2O_4)_{0.1}(SO_4)_{1.9}(OH)_6$

The particles A1 obtained in Example X-I-1 were dried at 150° C. for 2 hours to obtain particles A2.

Example X-I-3

Synthesis of $[Ag_{0.1}(NH_4)_{0.9}]Al_3(C_2O_4)_{0.0001}(SO_4)_{1.9999}(OH)_6$

The procedure of Example X-I-1 was repeated except that the amount of oxalic acid was changed to 0.0005 mol (0.063 g), and the obtained product was further dried at 150° C. for 2 hours to obtain particles A3.

Example X-I-4

Manufacture of $[Ag_{0.1}(NH_4)_{0.9}]Al_3(C_2O_4)_{0.01}(SO_4)_{1.999}(OH)_6$

The procedure of Example X-1-l was repeated except that the amount of oxalic acid was changed to 0.05 mol (6.3 g), and the obtained product was further dried at 150° C. for 2 hours to obtain particles A4.

Example X-I-5

Manufacture of $[Ag_{0.1}(NH_4)_{0.9}]Al_3(C_2O_4)_{0.4}(SO_4)_{1.7}(OH)_{5.8}$

The procedure of Example X-1-l was repeated except that the amount of oxalic acid was changed to 1.5 mol (189.1 g), and the obtained product was further dried at 150° C. for 2 hours to obtain particles A5.

Example X-I-6

Manufacture of $[Ag_{0.1}(NH_4)_{0.9}]Al_{2.7}(C_2O_4)_{0.1}(SO_4)_{1.9}(OH)_{5.1}$ The procedure of Example X-1-l was repeated except that the amount of aluminum sulfate was changed to 1,731 ml (1.8 mol), and the obtained product was further dried at 150° C. for 2 hours to obtain particles A6.

Example X-I-7

Manufacture of $[Ag_{0.1}(NH_4)_{0.9}]Al_{3.3}(C_2O_4)_{0.1}(SO_4)_{1.9}(OH)_{6.9}$ The procedure of Example X-1-l was repeated except that the amount of aluminum sulfate was changed to 2,115 ml (2.2 mol), and the obtained product was further dried at 150° C. for 2 hours to obtain particles A7.

Example X-I-8

Manufacture of $[Ag_{0.1}(NH_4)_{0.9}]Al_3(C_2O_4)_{0.1}(SO_4)_{2.4}(OH)_5$

The procedure of Example X-1-1 was repeated except that the amount of ammonium sulfate $(NH_4)_2SO_4$ was changed to 2.3 mol (303.9 g), and the obtained product was further dried at 150° C. for 2 hours to obtain particles A8.

Example X-I-9

Manufacture of $[Ag_{0.1}(NH_4)_{1.10}]_{1.2}Al_3(C_2O_4)_{0.1}(SO_4)_{1.9}(OH)_{6.02}$ The procedure of Example X-1-1 was repeated except that the agitation time after the addition of the ammonia aqueous solution was changed to 2 hours, the amount of the ammonia aqueous solution added was changed to 1,093 ml (9.84 mol) and the hydrothermal treatment time was changed to 30 minutes, and the obtained product was further dried at 150° C. for 2 hours to obtain particles A9.

Example X-I-10

Manufacture of $[Ag_{0.1}(NH_4)_{0.9}]Al_3(C_2O_4)_{0.1}(SO_4)_{1.9}(OH)_6$

The procedure of Example X-1-1 was repeated except that the hydrothermal treatment time at 100° C. was changed to 45 minutes, and the obtained product was further dried at 150° C. for 2 hours to obtain particles A10.

Example X-I-11

Manufacture of $[Ag_{0.1}(NH_4)_{0.76}]_{0.86}Al_3(C_2O_4)_{0.1}(SO_4)_{1.9}(OH)_{5.68}$ The procedure of Example X-1-1 was repeated except that the addition time of the ammonia aqueous solution was changed to 40 minutes and the amount of the ammonia aqueous solution added was changed to 755 ml (6.8 mol), and the obtained product was further dried at 150° C. for 2 hours to obtain particles A11.

Example X-I-12

Synthesis of $[Ag_{0.3}(NH_4)_{0.7}]Al_3(C_2O_4)_{0.1}(SO_4)_{1.9}(OH)_6$

The procedure of Example X-1-1 was repeated except that the amount of the aqueous solution of silver sulfate for ion exchange was changed to 1,800 ml, and the obtained product was further dried at 150° C. for 2 hours to obtain particles A12.

Example X-I-13

Manufacture of $[Ag_{0.001}(NH_4)_{0.999}]Al_3(C_2O_4)_{0.1}(SO_4)_{1.9}(OH)_6$

The procedure of Example X-1-1 was repeated except that the aqueous solution of silver sulfate for ion exchange was changed to an aqueous solution of silver nitrate, the concentration of the silver nitrate was 0.001 mol/l, the amount of the solution was changed to 300 ml and the treatment temperature was changed to 15° C., and the obtained product was further dried at 150° C. for 2 hours to obtain particles A13.

Example X-I-14

Manufacture of $[Ag_{0.00001}(NH_4)_{0.9999}]Al_3(C_2O_4)_{0.1}(SO_4)_{1.9}(OH)_6$ The concentration of the aqueous solution of silver nitrate for ion exchange was changed to 0.00001 mol/l in Example X-I-13, other procedure was carried out according to Example X-I-1 and the obtained product was further dried at 150° C. for 2 hours to obtain particles A14.

Example X-I-15

Manufacture of $[Ag_{0.1}(NH_4)_{0.9}]Al_3(C_2O_4)_{0.1}(SO_4)_{1.9}(OH)_6 \cdot 0.5H_2O$ 50 g of the sample obtained in Example X-I-1 was suspended in a 80° C. aqueous solution containing 1.5 g of sodium stearate, stirred for 30 minutes to carry out a surface treatment, dehydrated, rinsed, dried (105° C.×6 hours) and ground to obtain particles A15.

Example X-I-16

Manufacture of $[Ag_{0.1}(NH_4)_{0.9}]Al_3(C_2O_4)_{0.1}(SO_4)_{1.9}(OH)_6 \cdot 2H_2O$ The sample obtained in Example X-I-1 was left in a NaCl atmosphere at 30° C. and a relative humidity of 75% to carry out a moisture absorption treatment for 25 hours so as to obtain particles A16.

Example X-I-17

400° C.×1 Hour Baked Product of Example 1

The sample obtained in Example X-I-1 was baked at 400° C. for 1 hour under a nitrogen atmosphere to obtain particles 17.

When the particles 17 were analyzed by the powder X-ray diffraction method, all of them were $[Ag_{0.1}(NH_4)_{0.9}]Al_3(C_2O_4)_{0.1}(SO_4)_{1.9}(OH)_6$. They were spherical. 10.00 g of the particles A17 was added to 100 ml of ion exchange water, stirred at 20° C. for 30 minutes, dehydrated, rinsed and dried at 120° C. for 16 hours. The particles A17 had no weight loss and weighed 10.00 g.

Example X-I-18

500° C.×1 Hour Baked Product of Example 1

The sample obtained in Example X-I-1 was baked at 500° C. for 1 hour under a nitrogen atmosphere to obtain particles A18.

When the particles 18 were analyzed by the powder X-ray diffraction method, all of them were $[Ag_{0.1}(NH_4)_{0.9}]Al_3(C_2O_4)_{011}(SO_4)_{1.9}(OH)_6$. They were spherical. 10.00 g of the particles A18 were added to 100 ml of ion exchange water, stirred at 20° C. for 30 minutes, dehydrated, rinsed and dried at 120° C. for 16 hours. The particles A18 had no weight loss and weighed 10.00 g.

Example X-I-19

Manufacture of $[Ag_{0.001}K_{0.999}]Al_3(C_2O_4)_{0.1}(SO_4)_{1.9}(OH)_6$

Particles A19 were obtained from the following raw materials by the following method.

Raw Materials Used

| | | |
|---|---|---|
| Potassium sulfate | 2 mol | 348 g |
| Oxalic acid ($H_2C_2O_4 \cdot 2H_2O$) | 0.3 mol | 38 g |
| Aqueous solution of aluminum sulfate having a concentration of 1.04 mol/l | 2.0 mol | 1,923 ml |
| KOH aqueous solution having a concentration of 7.5 mol/l | 8.4 mol | 1,123 ml |

Synthesizing Method 348 g of potassium sulfate ($K_2SO_4$) was dissolved in 4.0 liters of ion exchange water. 38 g of oxalic acid ($H_2C_2O_4 \cdot 2H_2O$) was dissolved in 1.0 liter of ion exchange water.

The above aqueous solution of oxalic acid and the above aqueous solution of aluminum sulfate $Al_2(SO_4)_3$ were added to the aqueous solution of potassium sulfate ($K_2SO_4$) under agitation to prepare a mixed acid aqueous solution.

The mixed acid aqueous solution was fully stirred, and 1,120 ml of the above aqueous solution of potassium hydroxide was added to the mixed acid aqueous solution over 25 minutes to prepare a slurry of a potassium type organic acid anion-containing aluminum sulfate hydroxide particle precipitate.

This slurry was stirred for another 1 hour and subjected to a hydrothermal treatment in an autoclave at 140° C. for 2 hours.

The treated precipitate was filtered, rinsed and dried to obtain a powder sample.

100 g of the sample was collected, suspended in 300 ml of an aqueous solution of silver nitrate having a concentration of 0.001 mol/l and stirred to carry out ion exchange between potassium and silver under shaded light at 25° C. for 1 hour.

The sample after ion exchange was filtered, rinsed, dried (105° C.×6 hours) and ground. Further, the sample was dried at 200° C. for 2 hours after these steps to obtain particles A19.

Example X-I-20

Manufacture of $[Ag_{0.0001}K_{1.179}]_{1.18}Al_3(SO_4)_{2.26}(NO_3)_{0.04}(C_2O_4)_{0.07}(OH)_{5.48}$ The procedure of Example X-I-19 was repeated except that potassium sulfate used was changed to potassium nitrate $KNO_3$ to obtain particles A20.

Example X-I-21

Manufacture of $[Ag_{0.001}K_{1.179}]_{1.18}Al_3(SO_4)_{2.26}(NO_3)_{0.04}(C_2O_4)_{0.07}(OH)_{5.48}$ The procedure of Example X-I-19 was repeated except that $K_2SO_4$ was changed to $KNO_3$ and the hydrothermal treatment conditions were changed to 160° C. and 2 hours to obtain particles A21.

Example X-I-22

Manufacture of $[Ag_{0.001}K_{1.999}]Al_3(C_2O_4)_{0.1}(SO_4)_{1.9}(OH)_6$

The procedure of Example X-I-19 was repeated except that the hydrothermal treatment temperature was changed from 140° C. to 170° C. to obtain particles A22.

Example X-I-23

Manufacture of $[Ag_{0.1}Na_{0.9}]Al_3(C_6H_5O_7)_{0.067}(SO_4)_{1.9}(OH)_6$

Particles A23 were obtained from the following raw materials by the following method.

Raw Materials Used

| | | |
|---|---|---|
| sodium sulfate | 2 mol | 284.06 g |
| citric acid ($C_6H_8O_7 \cdot H_2O$) | 0.3 mol | 63 g |
| Aqueous solution of aluminum sulfate having a concentration of 1.04 mol/l | 2.0 mol | 1,923 ml |
| NaOH aqueous solution having a concentration of 3.36 mol/l | 8.2 mol | 2,440.5 ml |

Synthesizing Method 284.06 g of sodium sulfate ($Na_2SO_4$) was dissolved in 4.0 liters of ion exchange water. 63 g of citric acid was dissolved in 1.0 liter of ion exchange water.

The above aqueous solution of citric acid and the above aqueous solution of aluminum sulfate $Al_2(SO_4)_3$ were added to the aqueous solution of sodium sulfate ($Na_2SO_4$) under agitation to prepare a mixed acid aqueous solution.

2,440.5 ml of the above aqueous solution of sodium hydroxide was added to the mixed acid solution over 25 minutes under agitation to prepare a slurry of a sodium type silver- and organic acid anion-containing aluminum sulfate hydroxide particle precipitate.

This slurry was stirred for another 10 hour and subjected to a hydrothermal treatment in an autoclave at 170° C. for 2 hours.

The precipitate after the hydrothermal treatment was filtered, rinsed, dried and ground to obtain a powder sample.

Other steps were carried out in accordance with Example X-I-1, and then the obtained product was dried at 150° C. for 2 hours to obtain particles A23.

Example X-I-24

Manufacture of $[Ag_{0.1}Na_{0.9}]Al_3(C_6H_5O_7)_{0.067}(SO_4)_{1.9}(OH)_6$

The procedure of Example X-I-23 was repeated except that the addition time of sodium hydroxide was changed to 40 minutes and the agitation time after the addition of sodium hydroxide was changed to 1 hour, and the obtained product was further dried at 150° C. for 2 hours to obtain particles A24.

Example X-I-25

Manufacture of $[Ag_{0.1}Na_{0.9}]Al_3(C_4H_4O_6)_{0.1}(SO_4)_{1.9}(OH)_6$

Particles A25 were obtained from the following raw materials by the following method.

Raw Materials Used

| | | |
|---|---|---|
| sodium sulfate | 2 mol | 284.06 g |
| tartaric acid ($C_4H_6O_6$) | 0.3 mol | 45 g |
| Aqueous solution of aluminum sulfate having a concentration of 1.04 mol/l | 2.0 mol | 1,923 ml |
| NaOH aqueous solution having a concentration of 3.36 mol/l | 8.2 mol | 2,440.5 ml |

Synthesizing Method 284.06 g of sodium sulfate ($Na_2SO_4$) was dissolved in 4.0 liters of ion exchange water. 45 g of tartaric acid ($C_4H_6O_6$) was dissolved in 1.0 liter of ion exchange water.

The above aqueous solution of oxalic acid and the above aqueous solution of aluminum sulfate $Al_2(SO_4)_3$ were added to the aqueous solution of potassium sulfate ($K_2SO_4$) under agitation to prepare a mixed acid aqueous solution.

The mixed acid aqueous solution was fully stirred, and 244.05 ml of the above aqueous solution of sodium hydroxide was added to the mixed acid aqueous solution over 25 minutes to prepare a slurry of a sodium type silver- and organic acid anion-containing aluminum sulfate hydroxide particle precipitate.

This slurry was stirred for another 5 hours and subjected to a hydrothermal treatment in an autoclave at 170° C. for 2 hours.

The suspension after the hydrothermal treatment was filtered, rinsed, dried and ground.

Other steps were carried out in accordance with Example X-I-1, and the obtained product was further dried at 150° C. for 2 hours to obtain particles A25.

Example X-I-26

Manufacture of $[Ag_{0.1}Na_{0.9}]Al_3(C_4H_4O_6)_{0.1}(SO_4)_{1.9}(OH)_6$

The procedure of Example X-I-25 was repeated except that the amount of sodium hydroxide was changed to 8 mol (2,381 ml) and the addition time was changed to 40 minutes to obtain particles A26.

Example X-I-27

Manufacture of $[Ag_{0.1}(NH_4)_{0.9}]Al_{2.94}Zn_{0.01}Ti_{0.01}(C_2O_4)_{0.1}(SO_4)_{1.9}(OH)_6 \cdot 0.5H_2O$ The procedure of Example X-I-1 was repeated except that a sulfuric acid solution containing 2.5 g of zinc sulfate and 2.5 g of titanium sulfate $\{Ti_2(SO_4)_3\}$ was added to the mixed acid aqueous solution (the amount of the aqueous solution of aluminum sulfate of the mixed acid aqueous solution was reduced to 1,885 ml) of Example X-I-1, the silver ion exchange treatment temperature was changed to 80° C. and the treatment time was changed to 16 hours to obtain particles A27.

Example X-I-28

Manufacture of $[Ag_{0.1}(NH_4)_{0.9}]Al_{2.25}Zn_{0.5}Ti_{0.25}(C_2O_4)_{0.1}(SO_4)_{1.9}(OH)_6 \cdot 0.5H_2O$ The procedure of Example X-I-1 was repeated except that a sulfuric acid solution containing 125 g of zinc sulfate and 63 g of titanium sulfate $\{Ti_2(SO_4)_3\}$ were added to the mixed acid aqueous solution (the amount of the aqueous solution of aluminum sulfate of the mixed acid aqueous solution was reduced to 1,442 ml) of Example X-I-1, the silver ion exchange treatment temperature was changed to 80° C. and the treatment time was changed to 30 hours to obtain particles A28.

Example X-I-29

Manufacture of $[Ag_{0.1}(NH_4)_{0.9}]Al_3(C_2O_4)_{0.1}(SO_4)_{1.15}(PO_4)_{0.5}(OH)_6$ 371 g of the particles A1 right before ion exchange with silver (after the hydrothermal treatment) was added to an aqueous solution obtained by dissolving 74.5 g of ammonium phosphate in 500 ml of water and stirred at 100° C. for 1 hour to incorporate $PO_4^{3-}$ into the particles. The subsequent steps were carried out in accordance with Example X-I-1, and the obtained product was further dried at 150° C. for 2 hours to obtain silver- and organic acid anion-containing aluminum sulfate phosphate hydroxide particles A29.

In this example, silver- and organic acid anion-containing aluminum inorganic acid salt hydroxide particles having the same particle properties as the particles A29 and containing inorganic acid ions which were $CO_3^2$, $NO_3$, $SiO_4^2$ and $BO_3^{3-}$ were obtained by using sodium carbonate, sodium nitrate, sodium silicate and sodium borate in place of ammonium phosphate.

Example X-I-30

Manufacture of $[Ag_{0.1}Na_{0.9}]Al_3(SO_4)_{1.9}(C_2H_4O_5)_{0.1}(OH)_6$

The procedure of Example X-I-25 was repeated except that the organic acid used was changed from tartaric acid to DL-malic acid to obtain particles A30.

The characteristic properties of the particles are shown in Table 1. The particles were spherical as shown in FIG. 5.

Example X-I-31

Manufacture of $[Ag_{0.1}Na_{0.9}]Al_3(SO_4)_{1.9}[C_6H_2(OH)_3COO]_{0.067}(OH)_6$ The procedure of Example X-I-23 was repeated except that the organic acid used was changed from citric acid to gallic acid $[C_6H_4(OH)_3COOH]$ to obtain particles A31. The characteristic properties of the particles are shown in Table 1. The particles were spherical as shown in FIG. 6.

Comparative Example X-I-1

Manufacture of $[Ag_{0.1}(NH_4)_{0.9}]Al_3(SO_4)_2(OH)_6$

The procedure of Example X-I-1 was repeated except that oxalic acid was not used, and the obtained product was further dried at 150° C. for 2 hours to obtain particles V1.

Comparative Example X-I-2

Manufacture of $NH_4Al_3(C_2O_4)_{0.1}(SO_4)_{1.9}(OH)_6$

The procedure of Example X-I-1 was repeated except that ion exchange with a silver solution was not carried out, and the obtained product was further dried at 150° C. for 2 hours to obtain particles V2.

Comparative Example X-I-3

Manufacture of $KAl_3(C_2O_4)_{0.1}(SO_4)_{1.9}(OH)_6$

The procedure of Example X-I-19 was repeated except that ion exchange with a silver solution was not carried out to obtain particles V3.

TABLE 1

Spherical particles

Antibacterial agent

| Ex. or C. Ex. | Chemical formula<br>Note: ✗ means a product obtained by drying at 150° C. for 2 hours in Tables 1 to 6 below. | Particle name | Particle shape | Average secondary particle diameter μm | Sharpness of particle size distribution Dr = $D_{75}/D_{25}$ | BET specific surface area m²/g | Color | Powder X-ray diffraction pattern (peak other than that of compound of formula (1)) |
|---|---|---|---|---|---|---|---|---|
| Ex. X-I-1 | $[Ag_{0.1}(NH_4)_{0.9}]Al_3(C_2O_4)_{0.1}(SO_4)_{1.9}(OH)_6 \cdot 0.5H_2O$ | A1 | Spherical | 0.5 | 1.1 | 37 | White | None |
| Ex. X-I-2 | $[Ag_{0.1}(NH_4)_{0.9}]Al_3(C_2O_4)_{0.1}(SO_4)_{1.9}(OH)_6$ ✗ | A2 | Spherical | 0.5 | 1.1 | 37 | White | None |
| Ex. X-I-3 | $[Ag_{0.1}(NH_4)_{0.9}]Al_3(C_2O_4)_{0.0001}(SO_4)_{1.9999}(OH)_6$ ✗ | A3 | Spherical | 0.5 | 1.7 | 37 | White | None |
| Ex. X-I-4 | $[Ag_{0.1}(NH_4)_{0.9}]Al_3(C_2O_4)_{0.01}(SO_4)_{1.999}(OH)_6$ ✗ | A4 | Spherical | 0.5 | 1.5 | 37 | White | None |
| Ex. X-I-5 | $[Ag_{0.1}(NH_4)_{0.9}]Al_3(C_2O_4)_{0.4}(SO_4)_{1.7}(OH)_{5.8}$ ✗ | A5 | Spherical | 0.5 | 1.01 | 37 | White | None |
| Ex. X-I-6 | $[Ag_{0.1}(NH_4)_{0.9}]Al_{2.7}(C_2O_4)_{0.1}(SO_4)_{1.9}(OH)_{5.1}$ ✗ | A6 | Spherical | 0.5 | 1.29 | 37 | White | None |
| Ex. X-I-7 | $[Ag_{0.1}(NH_4)_{0.9}]Al_{3.3}(C_2O_4)_{0.1}(SO_4)_{1.9}(OH)_{6.9}$ ✗ | A7 | Spherical | 0.5 | 1.15 | 37 | White | None |
| Ex. X-I-8 | $[Ag_{0.1}(NH_4)_{0.9}]Al_3(C_2O_4)_{0.1}(SO_4)_{2.4}(OH)_5$ ✗ | A8 | Spherical | 0.5 | 1.15 | 37 | White | None |
| Ex. X-I-9 | $[Ag_{0.1}(NH_4)_{1.10}]_{1.2}Al_3(C_2O_4)_{0.1}(SO_4)_{1.9}(OH)_{6.02}$ ✗ | A9 | Spherical | 0.2 | 1.1 | 200 | White | None |
| Ex. X-I-10 | $[Ag_{0.1}(NH_4)_{0.9}]Al_3(C_2O_4)_{0.1}(SO_4)_{1.9}(OH)_6$ ✗ | A10 | Spherical | 0.35 | 1.1 | 75 | White | None |
| Ex. X-I-11 | $[Ag_{0.1}(NH_4)_{0.76}]_{0.86}Al_3(C_2O_4)_{0.1}(SO_4)_{1.9}(OH)_{5.68}$ ✗ | A11 | Spherical | 1 | 1.1 | 9 | White | None |
| Ex. X-I-12 | $[Ag_{0.3}(NH_4)_{0.7}]Al_3(C_2O_4)_{0.1}(SO_4)_{1.9}(OH)_6$ ✗ | A12 | Spherical | 0.5 | 1.1 | 37 | White | None |
| Ex. X-I-13 | $[Ag_{0.001}(NH_4)_{0.999}]Al_3(C_2O_4)_{0.1}(SO_4)_{1.9}(OH)_6$ ✗ | A13 | Spherical | 0.5 | 1.1 | 37 | White | None |
| Ex. X-I-14 | $[Ag_{0.00001}(NH_4)_{0.99999}]Al_3(C_2O_4)_{0.1}(SO_4)_{1.9}(OH)_6$ ✗ | A14 | Spherical | 0.5 | 1.1 | 37 | White | None |
| Ex. X-I-15 | $[Ag_{0.1}(NH_4)_{0.9}]Al_3(C_2O_4)_{0.1}(SO_4)_{1.9}(OH)_6 \cdot 0.5H_2O$<br>Surface treated | A15 | Spherical | 0.5 | 1.1 | 37 | White | None |
| Ex. X-I-16 | $[Ag_{0.1}(NH_4)_{0.9}]Al_3(C_2O_4)_{0.1}(SO_4)_{1.9}(OH)_6 \cdot 2H_2O$ | A16 | Spherical | 0.5 | 1.1 | 37 | White | None |
| Ex. X-I-17 | 400° C. × 1 hour baked product of Example 1 | A17 | Spherical | 0.5 | 1.1 | 37 | White | None |
| Ex. X-I-18 | 500° C. × 1 hour baked product of Example 1 | A18 | Spherical | 0.5 | 1.1 | 37 | White | None |
| Ex. X-I-19 | $[Ag_{0.001}K_{0.999}]Al_3(C_2O_4)_{0.1}(SO_4)_{1.9}(OH)_6$ ✗ | A19 | Spherical | 0.5 | 1.1 | 37 | White | None |
| Ex. X-I-20 | $[Ag_{0.1}K_{1.179}]_{1.18}Al_3(SO_4)_{2.26}(NO_3)_{0.04}(C_2O_4)_{0.07}(OH)_{5.48}$ ✗ | A20 | Spherical | 0.5 | 1.1 | 37 | White | None |
| Ex. X-I-21 | $[Ag_{0.01}K_{1.179}]_{1.18}Al_3(SO_4)_{2.26}(NO_3)_{0.04}(C_2O_4)_{0.07}(OH)_{5.48}$ ✗ | A21 | Spherical | 1.2 | 1.15 | 37 | White | None |
| Ex. X-I-22 | $[Ag_{0.001}K_{0.999}]Al_3(C_2O_4)_{0.1}(SO_4)_{1.9}(OH)_6$ ✗ | A22 | Spherical | 1.6 | 1.2 | 5 | White | None |
| Ex. X-I-23 | $[Ag_{0.1}Na_{0.9}]Al_3(C_6H_5O_7)_{0.067}(SO_4)_{1.9}(OH)_6$ ✗ | A23 | Spherical | 0.2 | 1.1 | 200 | White | None |
| Ex. X-I-24 | $[Ag_{0.1}Na_{0.9}]Al_3(C_6H_5O_7)_{0.067}(SO_4)_{1.9}(OH)_6$ ✗ | A24 | Spherical | 1 | 1.1 | 9 | White | None |
| Ex. X-I-25 | $[Ag_{0.1}Na_{0.9}]Al_3(C_4H_4O_6)_{0.1}(SO_4)_{1.9}(OH)_6$ ✗ | A25 | Spherical | 0.2 | 1.1 | 200 | White | None |
| Ex. X-I-26 | $[Ag_{0.1}Na_{0.9}]Al_3(C_4H_4O_6)_{0.1}(SO_4)_{1.9}(OH)_6$ ✗ | A26 | Spherical | 1 | 1.1 | 9 | White | None |
| Ex. X-I-27 | $[Ag_{0.1}(NH_4)_{0.9}]Al_{2.94}Zn_{0.01}Ti_{0.01}(C_2O_4)_{0.1}(SO_4)_{1.9}(OH)_6 \cdot 0.5H_2O$ | A27 | Spherical | 0.5 | 1.15 | 38 | White | None |
| Ex. X-I-28 | $[Ag_{0.1}(NH_4)_{0.9}]Al_{2.25}Zn_{0.5}Ti_{0.25}(C_2O_4)_{0.1}(SO_4)_{1.9}(OH)_6 \cdot 0.5H_2O$ | A28 | Spherical | 0.5 | 1.15 | 38 | White | None |
| Ex. X-I-29 | $[Ag_{0.1}(NH_4)_{0.9}]Al_3(C_2O_4)_{0.1}(SO_4)_{1.15}(PO_4)_{0.5}(OH)_6$ ✗ | A29 | Spherical | 0.6 | 1.15 | 30 | White | None |
| Ex. X-I-30 | $[Ag_{0.1}Na_{0.9}]Al_3(SO_4)_{1.9}(C_4H_4O_5)_{0.1}(OH)_6$ ✗ | A30 | Spherical | 0.4 | 1.07 | 115 | White | None |
| Ex. X-I-31 | $[Ag_{0.1}Na_{0.9}]Al_3(SO_4)_{1.9}[C_6H_2(OH)_3COO]_{0.067}(OH)_6$ ✗ | A31 | Spherical | 2.5 | 1.14 | 35 | White | None |
| C. Ex. X-I-1 | $Ag_{0.1}(NH_4)_{0.9}Al_3(SO_4)_2(OH)_6$ ✗ | V1 | Agglom- | 5 | 6 | 30 | White | None |
| C. Ex. X-I-2 | $NH_4Al_3(C_2O_4)_{0.1}(SO_4)_{1.9}(OH)_6$ ✗ | V2 | Spherical | 0.5 | 1.1 | 37 | White | None |
| C. Ex. X-I-3 | $KAl_3(C_2O_4)_{0.1}(SO_4)_{1.9}(OH)_6$ ✗ | V3 | Spherical | 0.5 | 1.1 | 37 | White | None |

Ex.: Example
C. Ex.: Comparative Example

Manufacture of Disk-Like Particles ("Go" Stone-Like Particles; Particles B)

Examples X-I-32 to X-I-34

Example X-I-32-1

Manufacture of $[Ag_{0.1}Na_{0.9}]Al_3(C_2O_4)_{0.1}(SO_4)_{1.9}(OH)_6$

Particles B1 were obtained from the following raw materials by the following synthesizing method.

Raw Materials Used

| sodium sulfate | 2 mol | 284.06 g |
|---|---|---|
| Oxalic acid ($H_2C_2O_4 \cdot 2H_2O$) | 0.3 mol | 38 g |
| Aqueous solution of aluminum sulfate having a concentration of 1.04 mol/l | 2.0 mol | 1,923 ml |
| NaOH aqueous solution having a concentration of 3.36 mol/l | 8.2 mol | 2,440.5 ml |

Synthesizing Method 284.06 g of sodium sulfate ($Na_2SO_4$) was dissolved in 4.0 liters of ion exchange water. 38 g of oxalic acid was dissolved in 1.0 liter of ion exchange water.

The above aqueous solution of oxalic acid and the aqueous solution of aluminum sulfate $Al_2(SO_4)_3$ were added to the aqueous solution of sodium sulfate ($Na_2SO_4$) under agitation to prepare a mixed acid aqueous solution.

This mixed acid aqueous solution was fully stirred, and then 2,440.5 ml of the above aqueous solution of sodium hydroxide was added to the mixed acid aqueous solution over 20 minutes to prepare a slurry of a sodium type silver- and organic acid anion-containing aluminum sulfate hydroxide particle precipitate.

This slurry was stirred for another 5 hours and subjected to a hydrothermal treatment at 170° C. for 2 hours. The treated precipitate was filtered, rinsed and dried. 100 g of the obtained sample was collected, suspended in 600 ml of an aqueous solution of silver sulfate having a concentration of 0.025 mol/l and stirred to carry out ion exchange between sodium ions and silver ions at 25° C. for 5 hours. 0.02 g of a polyacrylamide-based polymer coagulant (Sumifloc FN-20 of Sumitomo Chemical Co., Ltd.) was added to the sample after ion exchange and stirred for 10 minutes, and the obtained product was filtered, rinsed, dried (105° C.×6 hours) and ground. It was further dried at 200° C. for 2 hours to obtain particles B1-1.

Example X-I-32-2

2.6 g of zinc sulfate heptahydrate (first-grade reagent of Wako Pure Chemical Industries, Ltd.) and 2.2 g of ammonium sulfate (first-grade reagent of Wako Pure Chemical Industries, Ltd.) were added to 1,000 ml of ion exchange water heated at 80° C. to prepare a mixed solution. 95 g of the particles B1-1 was added to the mixed solution, stirred for 6 hours, dehydrated, rinsed and dried to obtain particles B1-2 treated with zinc and ammonium. The obtained particles had a Zn content of 0.1%, a $NH_4$ content of 0.4% and a BET specific surface area of 60 m²/g, and other properties were the same as those of the particles B1-1.

Thereafter, the same treatment was made on the particles A20, C1, D1, E1, F1, G1 and H1 to obtain the treated particles. All the treated particles had a Zn content of 0.10 and a $NH_4$ content of 0.4%. Although the BET specific surface areas of the treated particles were about 6 times larger than those of the particles before the treatment, the treated particles had almost the same average secondary particle diameters, particle size uniformity, particle shapes and other particle properties as those of the particles before the treatment. The whiteness of a resin composition obtained by adding the treated particles to a resin was further improved as compared with a resin composition obtained by adding the particles before the treatment to a resin.

Example X-I-33

Manufacture of $[Ag_{0.1}Na_{0.9}]Al_3(C_2O_4)_{0.1}(SO_4)_{1.9}(OH)_6$

The procedure of Example X-I-32-1 was repeated except that sodium sulfate used was changed to 4.0 liters of a reaction mother liquid containing 0.5 mol/l of sodium sulfate, the addition time of sodium hydroxide was changed to 40 minutes, and the agitation time after addition was changed to 1 hour to obtain particles B2.

Example X-I-34

Manufacture of $[Ag_{0.001}Na_{0.999}]Al_3(C_2O_4)_{0.1}(SO_4)_{1.9}(OH)_6$

The procedure of Example X-I-32-1 was repeated except that the concentration of the aqueous solution of silver sulfate was changed to 0.00025 mol/l to obtain particles B3.

Comparative Example X-I-4-(1)

Manufacture of $NaAl_3(C_2O_4)_{0.1}(SO_4)_{1.9}(OH)_6$

The procedure of Example X-I-32-1 was repeated except that ion exchange with silver ions was not carried out to obtain particles W1.

Comparative Example X-I-4-(2)

Manufacture of $[Ag_{0.1}Na_{0.9}]Al_3(SO_4)_2(OH)_6$

The procedure of Example X-I-32-1 was repeated except that oxalic acid was not used to obtain particles W2.

TABLE 2

| Ex. or C. Ex. | Chemical formula | Particle name | Particle shape | Average secondary particle diameter μm | Sharpness of particle size distribution Dr = $D_{75}/D_{25}$ | BET specific surface area $m^2/g$ | Color | Powder X-ray diffraction pattern (peak other than that of compound of formula (1)) |
|---|---|---|---|---|---|---|---|---|
| Ex. X-I-32-1 | $[Ag_{0.1}Na_{0.9}]Al_3(C_2O_4)_{0.1}(SO_4)_{1.9}(OH)_6$ | B1-1 | Disk-like | 1.3 | 1.1 | 10 | White | None |
| Ex. X-I-33 | $[Ag_{0.1}Na_{0.9}]Al_3(C_2O_4)_{0.1}(SO_4)_{1.9}(OH)_6 \cdot X$ | B2 | Disk-like | 7.0 | 1.1 | 0.6 | White | None |
| Ex. X-I-34 | $[Ag_{0.001}Na_{0.999}]Al_3(C_2O_4)_{0.1}(SO_4)_{1.9}(OH)_6 \cdot X$ | B3 | Disk-like | 1.3 | 1.1 | 10 | White | None |
| C. Ex. X-I-4-(1) | $NaAl_3(C_2O_4)_{0.1}(SO_4)_{1.9}(OH)_6 \cdot X$ | W1 | Disk-like | 0.2 | 1.1 | 220 | White | None |
| C. Ex. X-I-4-(2) | $[Ag_{0.1}Na_{0.9}]Al_3(SO_4)_2(OH)_6 \cdot X$ | W2 | Agglomerated | 2 | 6.5 | 180 | White | None |

Ex.: Example
C. Ex.: Comparative Example

Manufacture of Paired (Hamburger-Like) Particles (Particles C);

Examples X-I-35 to X-I-37

Example X-I-35

Manufacture of $[Ag_{0.1}Na_{0.9}]Al_3(C_2O_4)_{0.1}(SO_4)_{1.9}(OH)_6$

The procedure of Example X-I-32-1 was repeated except that the treatment temperature in the autoclave was changed to 180° C. and the treatment time was changed to 10 hours to obtain particles C1.

Example X-I-36

Manufacture of $[Ag_{0.1}Na_{0.9}]Al_3(C_2O_4)_{0.1}(SO_4)_{1.9}(OH)_6$

The procedure of Example X-I-32-1 was repeated except that treatment temperature in the autoclave was changed to 180° C., the treatment time was changed to 10 hours, sodium sulfate used was changed to 4.0 liters of a reaction mother liquid containing 0.5 mol/l of sodium sulfate, and the addition time of sodium hydroxide was changed to 40 minutes to obtain particles C2.

Example X-I-37

Manufacture of $[Ag_{0.001}Na_{0.999}]Al_3(C_2O_4)_{0.1}(SO_4)_{1.9}(OH)_6$

The procedure of Example X-I-32-1 was repeated except that the concentration of the aqueous solution of silver sulfate was changed to 0.00025 mol/l, the treatment temperature in the autoclave was changed to 180° C., and the treatment time was changed to 10 hours to obtain particles C3.

Comparative Example X-I-5-(1) $NaAl_3(C_2O_4)_{0.1}(SO_4)_{1.9}(OH)_6$

The procedure of Example X-I-35 was repeated except that ion exchange with silver ions was not carried out to obtain particles X1.

Comparative Example X-I-5-(2) $[Ag_{0.1}Na_{0.9}]Al_3(SO_4)_2(OH)_6$

The procedure of Example X-I-35 was repeated except that oxalic acid was not used to obtain particles X2.

TABLE 3

| Ex. or C. Ex. | Chemical formula | Particle name | Particle shape | Average secondary particle diameter μm | Sharpness of particle size distribution Dr = $D_{75}/D_{25}$ | BET specific surface area $m^2/g$ | Color | Powder X-ray diffraction pattern (peak other than that of compound of formula (1)) |
|---|---|---|---|---|---|---|---|---|
| Ex. X-I-35 | $[Ag_{0.1}Na_{0.9}]Al_3(C_2O_4)_{0.1}(SO_4)_{1.9}(OH)_6 \cdot X$ | C1 | Paired | 0.6 | 1.1 | 7 | White | None |
| Ex. X-I-36 | $[Ag_{0.1}Na_{0.9}]Al_3(C_2O_4)_{0.1}(SO_4)_{1.9}(OH)_6 \cdot X$ | C2 | Paired | 4.0 | 1.1 | 5 | White | None |
| Ex. X-I-37 | $[Ag_{0.001}Na_{0.999}]Al_3(C_2O_4)_{0.1}(SO_4)_{1.9}(OH)_6 \cdot X$ | C3 | Paired | 0.6 | 1.1 | 7 | White | None |
| C. Ex. X-I-5-(1) | $NaAl_3(C_2O_4)_{0.1}(SO_4)_{1.9}(OH)_6 \cdot X$ | X1 | Paired | 0.3 | 1.1 | 10 | White | None |
| C. Ex. X-I-5-(2) | $[Ag_{0.1}Na_{0.9}]Al_3(SO_4)_2(OH)_6 \cdot X$ | X2 | Agglomerated | 3 | 6 | 8 | White | None |

Ex.: Example
C. Ex.: Comparative Example

Manufacture of Rice Grain-Like Particles (Particles D);

Examples X-I-38 to X-I-40

Example X-I-38

Manufacture of $[Ag_{0.1}Na_{0.9}]Al_3(C_2H_4O_6)_{0.1}(SO_4)_{1.9}(OH)_6$

The procedure of Example X-I-23 was repeated except that tartaric acid was used in place of citric acid, and the obtained product was further dried at 150° C. for 2 hours to obtain particles D1.

Example X-I-39

Manufacture of $[Ag_{0.1}Na_{0.9}]Al_3(C_2H_4O_6)_{0.1}(SO_4)_{1.9}(OH)_6$

The procedure of Example X-I-23 was repeated except that tartaric acid was used in place of citric acid and the addition time of the NaOH aqueous solution was changed to 35 minutes, and the obtained product was further dried at 150° C. for 2 hours to obtain particles D2.

Example X-I-40

Manufacture of $[Ag_{0.001}Na_{0.999}]Al_3(C_2O_4)_{0.1}(SO_4)_{1.9}(OH)_6$

The procedure of Example X-I-23 was repeated except that tartaric acid was used in place of citric acid and the concentration of silver ions was changed to 0.00025 mol/l, and the obtained product was further dried at 150° C. for 2 hours to obtain particles D3.

Comparative Example X-I-6-(1) $NaAl_3(C_2H_4O_6)_{0.1}(SO_4)_{1.9}(OH)_6$

The procedure of Example X-I-38 was repeated except that ion exchange with silver ions was not carried out to obtain particles Y1.

Comparative Example X-I-6-(2)

Manufacture of $[Ag_{0.1}Na_{0.9}]Al_3(SO_4)_2(OH)_6$

The synthesizing procedure of Example X-I-38 was repeated except that tartaric acid was not used, and the obtained product was further dried at 200° C. for 2 hours to obtain particles Y2.

TABLE 4

| Ex. or C. Ex. | Chemical formula | Particle name | Particle shape | Average secondary particle diameter μm | Sharpness of particle size distribution $Dr = D_{75}/D_{25}$ | BET specific surface area $m^2/g$ | Color | Powder X-ray diffraction pattern (peak other than that of compound of formula (1)) |
|---|---|---|---|---|---|---|---|---|
| Ex. X-I-38 | $[Ag_{0.1}Na_{0.9}]Al_3(C_4H_4O_6)_{0.1}(SO_4)_{1.9}(OH)_6 \cdot X$ | D1 | Rice grain-like | 1.4 | 1.1 | 70 | White | None |
| Ex. X-I-39 | $[Ag_{0.1}Na_{0.9}]Al_3(C_4H_4O_6)_{0.1}(SO_4)_{1.9}(OH)_6 \cdot X$ | D2 | Rice grain-like | 4 | 1.1 | 49.2 | White | None |
| Ex. X-I-40 | $[Ag_{0.001}Na_{0.999}]Al_3(C_4H_4O_6)_{0.1}(SO_4)_{1.9}(OH)_6 \cdot X$ | D3 | Rice grain-like | 1.4 | 1.1 | 70 | White | None |
| C. Ex. X-I-6-(1) | $NaAl_3(C_4H_4O_6)_{0.1}(SO_4)_{1.9}(OH)_6 \cdot X$ | Y1 | Rice grain-like | 0.6 | 1.1 | 100 | White | None |
| C. Ex. X-I-6-(2) | $[Ag_{0.1}Na_{0.9}]Al_3(SO_4)_2(OH)_6 \cdot X$ | Y2 | Agglomerated | 6 | 7 | 80 | White | None |

Ex.: Example

C. Ex.: Comparative Example

Manufacture of Rectangular Parallelepiped Particles (Particles E);

Examples X-I-41 to X-I-44

Example X-I-41

Manufacture of $[Ag_{0.1}(H_3O)_{0.9}]Al_3(C_2O_4)_{0.1}(SO_4)_{1.9}(OH)_6$

Particles E1 were obtained from the following raw materials by the following synthesizing method.
Raw Materials Used

| | | |
|---|---|---|
| Aluminum sulfate having a concentration of 1.04 mol/l | 2.0 mol | 1923 ml |
| Aluminum hydroxide Al(OH)$_3$ (aluminum hydroxide; dried aluminum hydroxide gel S-100 of Kyowa Chemical Co., Ltd.; amorphous) Oxalic acid (H$_2$C$_2$O$_4$•2H$_2$O) | 2.0 mol 0.25 mol | 156.02 g 31.52 g |

Synthesizing Method

The above oxalic acid was added to the above aqueous solution of aluminum sulfate under agitation and the above aluminum hydroxide Al(OH)$_3$ was further added under agitation to prepare a slurry of a hydrogen type organic acid anion-containing aluminum sulfate hydroxide particle precipitate. Ion exchange water was added to the slurry to dilute it so as to prepare 7.0 liters of a solution, and the solution was further stirred at room temperature for 15 hours and subjected to a hydrothermal treatment in an autoclave at 170° C. for 5 hours.

The solution after the treatment was filtered, rinsed, dried and ground to obtain a sample. Other steps were carried out in accordance with Example X-I-1, and the obtained product was further dried at 150° C. for 2 hours to obtain particles E1.

Example X-I-42

Manufacture of $[Ag_{0.1}(H_3O)_{0.9}]Al_3(C_2O_4)_{0.1}(SO_4)_{1.9}(OH)_6$

The procedure of Example X-I-41 was repeated except that the agitation time before the treatment in the autoclave was changed to 30 minutes, and the treatment temperature in the autoclave was changed to 150° C., and the treatment time was changed to 2 hours to obtain particles E2.

Example X-I-43 $[Ag_{0.001}(H_3O)_{0.999}]Al_3(C_2O_4)_{0.1}(SO_4)_{1.9}(OH)_6$

The procedure of Example X-I-41 was repeated except that the concentration of silver ions to be exchanged was changed to 0.00025 mol/l to obtain particles E3.

Example X-I-44

Manufacture of $[Ag_{0.1}(H_3O)_{0.9}]Al_3(C_2O_4)_{0.1}(SO_4)_{1.9}(OH)_6$

The procedure of Example X-I-41 was repeated except that the agitation time before the treatment in the autoclave was changed to 2 hours to obtain particles E4.

Comparative Example X-I-7-(1)

Manufacture of $(H_3O)Al_3(C_2O_4)_{0.1}(SO_4)_{1.9}(OH)_6$

The procedure of Example X-I-41 was repeated except that ion exchange with silver ions was not carried out to obtain particles Z1.

Comparative Example X-I-7-(2)

Manufacture of $[Ag_{0.1}(H_3O)_{0.9}]Al_3(SO_4)_2(OH)_6$

The procedure of Example X-I-41 was repeated except that oxalic acid was not used to obtain particles Z2.

Comparative Example X-I-9

The particles R1 of Comparative Example X-I-9 were silver supporting zirconium phosphate having an average secondary particle diameter of 1.0 μm, a Dr of 4.5, a BET specific surface area of 4 m$^2$/g and a silver content of 3 W. The properties of the particles R1 are shown in Table-3.

TABLE 5

| | Antibacterial agent | | | | | | | |
|---|---|---|---|---|---|---|---|---|
| Ex. or C. Ex. | Chemical formula | Particle name | Particle shape | Average secondary particle diameter μm | Sharpness of particle size distribution Dr = D$_{75}$/D$_{25}$ | BET specific surface area m$^2$/g | Color | Powder X-ray diffracttion pattern (peak other than that of compound of formula (1)) |
| Ex. X-I-41 | $[Ag_{0.1}(H_3O)_{0.9}]Al_3(C_2O_4)_{0.1}(SO_4)_{1.9}(OH)_6$·X̶ | E1 | Rectangular parallelepiped | 0.8 | 1.1 | 12 | White | None |
| Ex. X-I-42 | $[Ag_{0.1}(H_3O)_{0.9}]Al_3(C_2O_4)_{0.1}(SO_4)_{1.9}(OH)_6$·X̶ | E2 | Rectangular parallelepiped | 3.0 | 1.6 | 0.6 | White | None |
| Ex. X-I-43 | $[Ag_{0.001}(H_3O)_{0.999}]Al_3(C_2O_4)_{0.1}(SO_4)_{1.9}(OH)_6$·X̶ | E3 | Rectangular parallelepiped | 0.8 | 1.1 | 12 | White | None |
| Ex. X-I-44 | $[Ag_{0.1}(H_3O)_{0.9}]Al_3(C_2O_4)_{0.1}(SO_4)_{1.9}(OH)_6$·X̶ | E4 | Rectangular parallelepiped | 1.0 | 1.4 | 4 | White | None |
| C. Ex. X-I-7-(1) | $(H_3O)Al_3(C_2O_4)_{0.1}(SO_4)_{1.9}(OH)_6$·X̶ | Z1 | Rectangular parallelepiped | 0.5 | 1.1 | 20 | White | None |
| C. Ex. X-I-7-(2) | $[Ag_{0.1}(H_3O)_{0.9}]Al_3(SO_4)_2(OH)_6$·X̶ | Z2 | Agglomerated | 5 | 6.4 | 16 | White | None |

TABLE 5-continued

| | | | | | Average secondary particle diameter μm | Sharpness of particle size distribution $Dr = D_{75}/D_{25}$ | BET specific surface area $m^2/g$ | Color | Powder X-ray diffracttion pattern (peak other than that of compound of formula (1)) |
|---|---|---|---|---|---|---|---|---|---|
| Ex. or C. Ex. | Chemical formula | | Particle name | Particle shape | | | | | |
| Ex. X-I-9 | Silver supporting zirconium phosphate (containing 3% of Ag) ※ | | R1 | Rectangular parallelepiped | 1.0 | 1.4 | 4 | White | — |

Ex.: Example
C. Ex.: Comparative Example

Manufacture of Hexagonal Plate-Like Particles (Particles F);

Example X-I-45

Example X-I-45

Manufacture of $[Ag_{0.1}Na_{0.9}]Al_3(SO_4)_{1.9}(C_2O_4)_{0.1}(OH)_6$ 2 mol of aluminum sulfate and 2 mol of sodium sulfate were dissolved in 6,000 ml of pure water, and 31.52 g (0.25 mol) of oxalic acid was added to the resulting solution. 1,800 ml of an aqueous solution containing 8.8 mol (352 g) of sodium hydroxide was added to the mixed solution under agitation, further stirred at room temperature for 30 minutes, subjected to a hydrothermal treatment at 180° C. for 20 hours, cooled to normal temperature, filtered, rinsed and dried at 95° C. for 15 hours to obtain organic acid anion-containing aluminum sulfate hydroxide particles.

Subsequent steps were carried out in accordance with Example X-I-1, and the obtained product was further dried at 150° C. for 2 hours to obtain particles F1.

The characteristic properties of the particles are shown in Table 6. The particles were shaped like a hexagonal plate as shown in FIG. 11.

Manufacture of Octahedral Particles (Particles G);

Example X-I-46

Example X-I-46

Manufacture of $[Ag_{0.1}Na_{0.9}]Al_3(SO_4)_{1.9}[CH_3CH(OH)COO]_{0.067}(OH)_6$ The procedure of Example X-I-23 was repeated except that the organic acid used was changed from citric acid to L-lactic acid [$CH_3CH(OH)COOH$] to obtain particles G1. The characteristic properties of the particles are shown in Table 6. The particles were octahedral as shown in FIG. 12.

Manufacture of Columnar Particles (Cask-Like Particles; Particles H);

Example X-I-47

Manufacture of $[Ag_{0.1}Na_{0.9}]Al_3(SO_4)_{1.9}[HOCH_2CH(OH)COO]_{0.067}(OH)_6$ The procedure of Example X-I-23 was repeated except that the organic acid used was changed from citric acid to DL-glyceric acid [$HOCH_2CH(OH)COOH$] to obtain particles H1. The characteristic properties of the particles are shown in Table 6. The particles were columnar (cask-like) as shown in FIG. 13.

TABLE 6

| Ex. or C. Ex. | Chemical formula | Particle name | Particle shape | Average secondary particle diameter μm | Sharpness of particle size distribution $Dr = D_{75}/D_{25}$ | BET specific surface area $m^2/g$ | Color | Powder X-ray diffracttion pattern (peak other than that of compound of formula (1)) |
|---|---|---|---|---|---|---|---|---|
| Ex. X-I-45 | $[Ag_{0.1}Na_{0.9}]Al_3(SO_4)_{1.9}(C_2O_4)_{0.1}(OH)_6$ ※ | F1 | Hexagonal plate-like | 0.8 | 1.15 | 10.5 | White | None |
| Ex. X-I-46 | $[Ag_{0.1}Na_{0.9}]Al_3(SO_4)_{1.9}[CH_3CH(OH)COO]_{0.067}(OH)_6$ ※ | G1 | Octahedral | 0.6 | 1.06 | 30 | White | None |
| Ex. X-I-47 | $[Ag_{0.1}Na_{0.9}]Al_3(SO_4)_{1.9}[HOCH_2CH(OH)COO]_{0.067}(OH)_6$ ※ | H1 | Columnar (cask-like) | 3.1 | 1.18 | 9 | White | None |

Ex.: Example
C. Ex.: Comparative Example

The particles A1 to A31, B1 to B3, C1 to C3, D1 to D3, E1 to E4, F1, G1 and H1 of the above Examples X-I were synthesized from high-purity raw materials (purified to such an extent that the contents of Pb, Cd, As and Ba were all 0.1 ppm or less, the content of Fe was 10 ppm or less, and the contents of Mn, Cu, Cr and Ni were 1 ppm or less) by using an apparatus made of the above corrosion resistant material.

Therefore, the contents of impurities were different from those of natural alum, that is, the contents of Pb, Cd, As and Ba were all 0.1 ppm or less, the content of Fe was 10 ppm or less, the contents of Mn, Cu, Cr and Ni were 1 ppm or less, and the content of Cl was 100 ppm or less.

The contents of impurities were measured by atomic absorption spectrophotometry, ICP-AES (Inductively Coupled Plasma-Atomic Emission Spectroscopy) or fluorescent X-ray spectroscopy.

A detailed description is subsequently given of an antibacterial resin composition obtained by blending the antibacterial agent of the present invention into a resin and the method of manufacturing an antibacterial resin product based on examples. The amounts of components are based on 100 parts by weight of the resin.

2,5-thiophenediyl(5-tert-butyl-1,3-benzohexazole) which is a fluorescent brightener was added in an amount shown in tables.

Polypropylene Molded Articles;

Examples X-II-1 to X-II-32 and Comparative Examples X-II-1 to X-II-4

In Example X-II-1, 100 parts by weight of polypropylene for transparent injection molding, 0.06 part by weight of the particles A1 shown in Table-1 and 2,5-thiophenediyl(5-tert-butyl-1,3-benzohexazole) (amount shown in Table-7) as a fluorescent brightener were pre-mixed and kneaded together by a double-screw kneading extruder at 230° C. to obtain a mixture pellet which was then injection molded at 230° C. to obtain a 2 mm-thick test piece for various tests and measure its antibacterial properties (antibacterial action retention characteristics right after molding and after contact with tap water), transparency and whiteness in accordance with the above measurement methods (7) to (10) for resin products. The results are shown on the left side of the vertical double lines in Table-7.

A test of filter passability at the time of kneading and extrusion (pressure of extruder) was conducted in accordance with the above method (11). The results are shown on the right side of the vertical double lines in Table-7.

In the tests of Examples X-II-2 to X-II-32, a test piece was prepared in the same manner as in Example X-II-1 except that the type and amount of the antibacterial agent particles used in Example X-II-1 were changed as shown in Table-7 to carry out tests. The results are shown in Table-7.

Comparative Example X-II-1 differs from Example X-II-1 in that silver-containing aluminum sulfate hydroxide particles containing no organic acid which are particles V1, W2, X2, Y2 or Z2 having a large Dr width (particle size distribution width) or silver supporting zirconium phosphate particles R1 were used, Comparative Example X-II-2 differs from Example X-II-1 in that no antibacterial agent was added in the tests, Comparative Example X-II-3 differs from Example X-II-1 in that aluminum sulfate hydroxide particles V3 containing no silver were used, and Comparative Example X-II-4 differs from Example X-II-1 in that aluminum sulfate hydroxide particles V3 containing no silver were used. Test pieces were prepared in the same manner as in Example X-II-1 except that the amount of the antibacterial agent differed in some of Examples as shown in Table-1 and the same measurements were made on the test pieces.

The results are shown in Table-7.

TABLE 7

| | Antibacterial agent | | | Antibacterial properties | | Antibacterial action Retention characteristics after contact with tap water |
|---|---|---|---|---|---|---|
| | | | | Antibacterial properties right after molding | | at 90° C. |
| Ex. or C. Ex. | Name of antibacterial agent particle | Amount of antibacterial agent | Amount of fluorescent brightener pbw | Escherichia coli cfu/ml | Staphylococcus aureus cfu/ml | (Escherichia coli) cfu/ml |
| Ex. X-II-1 | A1 | 0.06 | 0 | 10> | 10> | 10> |
| | | | 0.0001 | 10> | 10> | 10> |
| Ex. X-II-2 | A2 | 0.06 | 0 | 10> | 10> | 10> |
| Ex. X-II-3 | A3 | 0.06 | 0 | 3 × 10 | 3 × 10 | 3 × 10 |
| Ex. X-II-4 | A4 | 0.06 | 0 | 1 × 10 | 1 × 10 | 1 × 10 |
| Ex. X-II-5 | A5 | 0.06 | 0 | 10> | 10> | 10> |
| Ex. X-II-6 | A6 | 0.06 | 0 | 1 × 10 | 1 × 10 | 1 × 10 |
| Ex. X-II-7 | A7 | 0.06 | 0 | 1 × 10 | 1 × 10 | 1 × 10 |
| Ex. X-II-8 | A8 | 0.06 | 0 | 1 × 10 | 1 × 10 | 1 × 10 |
| Ex. X-II-9 | A9 | 0.06 | 0 | 10> | 10> | 10> |
| Ex. X-II-10 | A10 | 0.06 | 0 | 10> | 10> | 10> |
| Ex. X-II-11 | A11 | 0.06 | 0 | 1 × 10 | 1 × 10 | 1 × 10 |
| Ex. X-II-12 | A12 | 0.001 | 0.001 | 8 × 10 | 8 × 10 | 9 × 10 |
| Ex. X-II-13 | A13 | 2 | 0.001 | 1 × 10 | 1 × 10 | 1 × 10 |
| Ex. X-II-14 | A14 | 300 | 0.001 | 1 × 10 | 1 × 10 | 1 × 10 |

TABLE 7-continued

| | | | | | | |
|---|---|---|---|---|---|---|
| Ex. X-II-15 | A15 | 0.06 | 0 | 10> | 10> | 10> |
| Ex. X-II-16 | A16 | 0.06 | 0 | 10> | 10> | 10> |
| Ex. X-II-17 | A17 | 0.06 | 0 | 10> | 10> | 10> |

| | Antibacterial properties | | Pressure of extruder Kg/cm² | |
|---|---|---|---|---|
| Ex. C. Ex. | Transparency % | Color | 2 hours | 24 hours |
| Ex. X-II-1 | 100 | Achromatic (white) | 21 | 25 |
| | 100 | Achromatic (white) | | |
| Ex. X-II-2 | 100 | Achromatic (white) | 21 | 25 |
| Ex. X-II-3 | 100 | Achromatic (white) | 33 | 90 |
| Ex. X-II-4 | 100 | Achromatic (white) | 28 | 70 |
| Ex. X-II-5 | 100 | Achromatic (white) | 21 | 24 |
| Ex. X-II-6 | 100 | Achromatic (white) | 26 | 65 |
| Ex. X-II-7 | 100 | Achromatic (white) | 21 | 25 |
| Ex. X-II-8 | 100 | Achromatic (white) | 22 | 28 |
| Ex. X-II-9 | 100 | Achromatic (white) | 22 | 25 |
| Ex. X-II-10 | 100 | Achromatic (white) | 21 | 25 |
| Ex. X-II-11 | 100 | Achromatic (white) | 21 | 25 |
| Ex. X-II-12 | 100 | Achromatic (white) | 21 | 25 |
| Ex. X-II-13 | 98 | Achromatic (white) | 21 | 25 |
| Ex. X-II-14 | 10 | Achromatic (white) | 21 | 25 |
| Ex. X-II-15 | 100 | Achromatic (white) | 21 | 25 |
| Ex. X-II-16 | 100 | Achromatic (white) | 21 | 25 |
| Ex. X-II-17 | 100 | Achromatic (white) | 21 | 25 |

| | | | | Antibacterial properties | | |
|---|---|---|---|---|---|---|
| | | | Amount of | Antibacterial properties right after molding | | Antibacterial action retention characteristics after contact with tap water |
| Ex. C. Ex. | Name of antibacterial agent particle | Amount of antibacterial agent | fluorescent brightener pbw | *Escherichia coli* cfu/ml | *Staphylococcus aureus* cfu/ml | at 90° C. (*Escherichia coli*) cfu/ml |
| Ex. X-II-18 | A18 | 0.06 | 0 | 10> | 10> | 10> |
| Ex. X-II-19 | A19 | 2 | 0.1 | 1 × 10 | 1 × 10 | 1 × 10 |
| Ex. X-II-20 | A20 | 2 | 0.1 | 1 × 10 | 1 × 10 | 1 × 10 |
| Ex. X-II-21 | A21 | 2 | 0.1 | 1 × 10 | 1 × 10 | 1 × 10 |
| Ex. X-II-22 | A22 | 2 | 0.1 | 1 × 10 | 1 × 10 | 1 × 10 |
| Ex. X-II-23 | A23 | 0.06 | 0 | 10> | 10> | 10> |
| Ex. X-II-24 | A24 | 0.06 | 0.001 | 10> | 10> | 10> |
| Ex. X-II-25 | A25 | 0.06 | 0 | 10> | 10> | 10> |
| Ex. X-II-26 | A26 | 0.06 | 0.001 | 10> | 10> | 10> |
| Ex. X-II-27 | A27 | 0.06 | 0 | 10> | 10> | 10> |
| Ex. X-II-28 | A28 | 0.06 | 0 | 10> | 10> | 10> |
| Ex. X-II-29 | A29 | 0.06 | 0 | 10> | 10> | 10> |
| Ex. X-II-30 | A30 | 0.06 | 0 | 10> | 10> | 10> |
| Ex. X-II-31 | A31 | 0.06 | 0 | 1 × 10 | 1 × 10 | 1 × 10 |

| | Antibacterial properties | | Pressure of extruder Kg/cm² | |
|---|---|---|---|---|
| Ex. C. Ex. | Transparency % | Color | 2 hours | 24 hours |
| Ex. X-II-18 | 100 | Achromatic (white) | 21 | 25 |
| Ex. X-II-19 | 98 | Achromatic (white) | 21 | 25 |
| Ex. X-II-20 | 98 | Achromatic (white) | 21 | 25 |
| Ex. X-II-21 | 97 | Achromatic (white) | 21 | 25 |
| Ex. X-II-22 | 96 | Achromatic (white) | 21 | 27 |
| Ex. X-II-23 | 100 | Achromatic (white) | 21 | 25 |
| Ex. X-II-24 | 100 | Achromatic (white) | 21 | 25 |
| Ex. X-II-25 | 100 | Achromatic (white) | 21 | 25 |
| Ex. X-II-26 | 100 | Achromatic (white) | 21 | 25 |
| Ex. X-II-27 | 100 | Achromatic (white) | 22 | 25 |
| Ex. X-II-28 | 100 | Achromatic (white) | 22 | 25 |
| Ex. X-II-29 | 100 | Achromatic (white) | 22 | 25 |

TABLE 7-continued

| | | | | |
|---|---|---|---|---|
| Ex. X-II-30 | 100 | Achromatic (white) | 21 | 25 |
| Ex. X-II-31 | 100 | Achromatic (white) | 22 | 25 |

| | | | Antibacterial properties | | |
|---|---|---|---|---|---|
| | | | | Antibacterial properties right after molding | | Antibacterial action retention characteristics after contact with tap water |
| Ex. C. Ex. | Name of antibacterial agent particle | Amount of antibacterial agent pbw | Amount of fluorescent brightener pbw | *Escherichia coli* cfu/ml | *Staphylococcus aureus* cfu/ml | at 90° C. (*Escherichia coli*) cfu/ml |
| Ex. X-II-32 | B1-1 | 0.06 | 0 | 10> | 10> | 10> |
| | B1-2 | 0.06 | 0 | 10> | 10> | 10> |
| | B2 | 0.06 | 0 | 5 × 10 | 5 × 10 | 5 × 10 |
| | B3 | 2 | 0.001 | 1 × 10 | 1 × 10 | 1 × 10 |
| | C1 | 0.06 | 0 | 10> | 10> | 10> |
| | C2 | 0.06 | 0 | 3 × 10 | 3 × 10 | 3 × 10 |
| | C3 | 2 | 0.001 | 1 × 10 | 1 × 10 | 1 × 10 |
| | D1 | 0.06 | 0 | 10> | 10> | 10> |
| | D2 | 0.06 | 0 | 3 × 10 | 3 × 10 | 3 × 10 |
| | D3 | 2 | 0.001 | 1 × 10 | 1 × 10 | 1 × 10 |
| | E1 | 0.06 | 0 | 10> | 10> | 10> |
| | E2 | 0.06 | 0 | 3 × 10 | 3 × 10 | 3 × 10 |
| | E3 | 2 | 0.001 | 1 × 10 | 1 × 10 | 1 × 10 |
| | E4 | 0.06 | 0 | 10> | 10> | 10> |
| | F1 | 0.06 | 0 | 10> | 10> | 10> |
| | G1 | 0.06 | 0 | 10> | 10> | 10> |
| | H1 | 0.06 | 0 | 1 × 10 | 1 × 10 | 1 × 10 |

| | Antibacterial properties | | | | |
|---|---|---|---|---|---|
| Ex. C. Ex. | Name of antibacterial agent particle | Transparency % | Color | Pressure of extruder Kg/cm² | |
| | | | | 2 hours | 24 hours |
| Ex. X-II-32 | B1-1 | 100 | Achromatic (white) | 21 | 25 |
| | B1-2 | 100 | Achromatic (white) | 21 | 25 |
| | B2 | 100 | Achromatic (white) | 23 | 30 |
| | B3 | 100 | Achromatic (white) | 21 | 25 |
| | C1 | 100 | Achromatic (white) | 21 | 25 |
| | C2 | 100 | Achromatic (white) | 22 | 26 |
| | C3 | 99 | Achromatic (white) | 21 | 25 |
| | D1 | 100 | Achromatic (white) | 21 | 25 |
| | D2 | 100 | Achromatic (white) | 21 | 26 |
| | D3 | 98 | Achromatic (white) | 21 | 25 |
| | E1 | 100 | Achromatic (white) | 21 | 25 |
| | E2 | 100 | Achromatic (white) | 28 | 70 |
| | E3 | 98 | Achromatic (white) | 21 | 25 |
| | E4 | 100 | Achromatic (white) | 27 | 60 |
| | F1 | 100 | Achromatic (white) | 21 | 25 |
| | G1 | 100 | Achromatic (white) | 21 | 24 |
| | H1 | 100 | Achromatic (white) | 22 | 30 |

| | | | Antibacterial properties | | |
|---|---|---|---|---|---|
| | | | | Antibacterial properties right after molding | | Antibacterial action retention characteristics after contact with tap water |
| Ex. C. Ex. | Name of antibacterial agent particle | Amount of antibacterial agent pbw | Amount of fluorescent brightener pbw | *Escherichia coli* cfu/ml | *Staphylococcus aureus* cfu/ml | at 90° C. (*Escherichia coli*) cfu/ml |
| C. Ex. II-1 | V1 | 0.06 | 0 | 8 × 10² | 8 × 10² | 1 × 10³ |
| | W2 | 0.06 | 0 | 5 × 10² | 6 × 10² | 1 × 10³ |
| | X2 | 0.06 | 0 | 6 × 10² | 7 × 10² | 1 × 10³ |
| | Y2 | 0.06 | 0 | 8 × 10² | 8 × 10² | 1 × 10³ |
| | Z2 | 0.06 | 0 | 8 × 10² | 8 × 10² | 1 × 10³ |
| | R1 | 0.06 | 0 | 10> | 10> | 9 × 10⁶ |
| | | 2 | 0.001 | 10> | 10> | 5 × 10⁵ |

TABLE 7-continued

| Ex. C. Ex. | | | | | | |
|---|---|---|---|---|---|---|
| C. Ex. II-2 | No antibacterial agent | 0 | 0 | $8 \times 10^6$ | $7 \times 10^6$ | $9 \times 10^6$ |
| C. Ex. II-3 | V2 | 0.06 | 0 | $7 \times 10^6$ | $7 \times 10^6$ | $9 \times 10^6$ |
| C. Ex. II-4 | V3 | 300 | 0 | $7 \times 10^6$ | $6 \times 10^6$ | $8 \times 10^6$ |

| | Antibacterial properties | | | | |
|---|---|---|---|---|---|
| Ex. C. Ex. | Name of antibacterial agent particle | Transparency % | Color | Pressure of extruder Kg/cm² 2 hours | 24 hours |
| C. Ex. X-II-1 | V1 | 92 | Achromatic (white) | 200< | 200< |
| | W2 | 92 | Achromatic (white) | 200< | 200< |
| | X2 | 92 | Achromatic (white) | 200< | 200< |
| | Y2 | 92 | Achromatic (white) | 200< | 200< |
| | Z2 | 92 | Achromatic (white) | 200< | 200< |
| | R1 | 90 | Achromatic (white) | 28 | 70 |
| | | 50 | Achromatic (white) | | |
| C. Ex. II-2 | No antibacterial agent | 100 | Achromatic (white) | 20 | 22 |
| C. Ex. II-3 | V2 | 100 | Achromatic (white) | 21 | 25 |
| C. Ex. II-4 | V3 | 1> | Achromatic (white) | 21 | 25 |

Ex.: Example
C. Ex.: Comparative Example
pbw: part by weight

It was confirmed that the molded articles of Examples were excellent in antibacterial properties right after molding, antibacterial action retention characteristics after contact with tap water, transparency, color and filter passability at the time of kneading and extrusion. On the other hand, the molded articles of Comparative Examples had a problem with at least one of these properties.

In the experiments, it was observed that as the average secondary particle diameter of the silver- and organic acid anion-containing aluminum sulfate hydroxide particle antibacterial agent becomes smaller, antibacterial properties and transparency become higher, as the BET specific surface area becomes larger, antibacterial properties become higher, and when the Dr width (particle size distribution width) is small, the particle diameter is uniform and a fixed amount of an organic acid is contained, antibacterial properties tend to be high.

Looking at Comparative Examples, in Comparative Example X-II-1 in which the particles V1, W2, X2, Y2 and Z2 all of which are silver-containing aluminum sulfate hydroxide particles containing no organic acid and having a large Dr width (particle size distribution width) were used, as the organic acid was not contained, antibacterial properties were unsatisfactory, filter passability at the time of kneading and extrusion became worse right after operation to such an extent that the operation of the machine became difficult, and transparency slightly lowered.

It was observed that Comparative Example X-II-1 in which zirconium phosphate-based particles R1 were used was inferior to Examples in antibacterial action retention characteristics after contact with tap water and transparency.

Since no antibacterial agent was added in Comparative Example X-II-2, though there was no problem with transparency and color, no antibacterial effect was observed at all and the object of the present invention was not attained.

Although 300 parts by weight of organic acid anion-containing aluminum sulfate hydroxide particles was used in Comparative Example X-II-4, as they were not organic acid anion-containing aluminum sulfate hydroxide particles containing silver, no antibacterial effect was observed at all.

That is, even when aluminum sulfate hydroxide particles are used, as understood from Comparative Examples X-II-3 and X-II-4, it is found that aluminum sulfate hydroxide particles containing no silver cannot provide antibacterial properties to molded articles.

Polystyrene and Acrylic Resin Transparent Resin Molded Articles

Examples X-II-33 and X-II-34 and Comparative Examples X-II-5, 6 and 7

In Examples X-II-33 and X-II-34, the procedure of X-II-1 was repeated except that the resin to be made antibacterial was changed from polypropylene to transparent resins such as polystyrene and acrylic resin, the amounts of the antibacterial agent and the fluorescent brightener were changed as shown in Table-8, and the kneading and molding temperatures were changed to 210° C. The amounts of the components are shown in Table-8.

The procedure of Example X-II-33 was repeated except that no antibacterial agent was added in Comparative Example X-II-5, the antibacterial agent was changed to the particles V2 in Comparative Example X-II-6 and the antibacterial agent was changed to the particles Y1 in Comparative Example X-II-7. The measurement results of antibacterial properties, transparency and color are shown in Table-8.

As shown in Table-8 below, it was confirmed that the molded articles of Examples were achromatic (white) and excellent in antibacterial properties (antibacterial action retention characteristics right after molding and after contact with tap water) with almost unimpaired transparency.

On the other hand, since silver was not contained in the aluminum sulfate hydroxide particles in Comparative Examples, antibacterial properties were not obtained at all.

TABLE 8

| Ex. C. Ex. | Resin to be made antibacterial | Name of antibacterial agent particle | Amount of antibacterial agent | Amount of fluorescent brightener (pbw) | Antibacterial properties right after molding *Escherichia coli* cfu/ml | Antibacterial properties right after molding *Staphylococcus aureus* cfu/ml | Antibacterial action retention characteristics after contact with tap water at 70° C. (*Escherichia coli*) cfu/ml |
|---|---|---|---|---|---|---|---|
| Ex. X-II-33 | Polystyrene | A2 | 0.1 | 0 | 10> | 10> | 10> |
|  |  | B1-2 | 0.1 | 0 | 10> | 10> | 10> |
|  |  | C1 | 0.1 | 0 | 10> | 10> | 10> |
|  |  | D1 | 0.1 | 0 | 10> | 10> | 10> |
|  |  | E1 | 0.1 | 0 | 10> | 10> | 10> |
|  |  | F1 | 0.1 | 0 | 10> | 10> | 10> |
|  |  | G1 | 0.1 | 0 | 10> | 10> | 10> |
|  |  | H1 | 0.1 | 0 | $1 \times 10$ | $1 \times 10$ | $1 \times 10$ |
| Ex. X-II-34 | Acrylic resin | A2 | 0.1 | 0 | 10> | 10> | 10> |
|  |  | B1-2 | 0.1 | 0 | 10> | 10> | 10> |
|  |  | C1 | 0.1 | 0 | 10> | 10> | 10> |
|  |  | D1 | 0.1 | 0 | 10> | 10> | 10> |
|  |  | E1 | 0.1 | 0 | 10> | 10> | 10> |
|  |  | F1 | 0.1 | 0 | 10> | 10> | 10> |
|  |  | G1 | 0.1 | 0 | 10> | 10> | 10> |
|  |  | H1 | 0.1 | 0 | $1 \times 10$ | $1 \times 10$ | $1 \times 10$ |
| C. Ex. X-II-5 | polystyrene | nil | 0 | 0 | $7 \times 10^6$ | $8 \times 10^6$ | $9 \times 10^6$ |
| C. Ex. X-II-6 | polystyrene | V2 | 2 | 0.01 | $7 \times 10^6$ | $8 \times 10^6$ | $9 \times 10^6$ |
| C. Ex. X-II-7 | polystyrene | Y1 | 2 | 0.01 | $7 \times 10^6$ | $8 \times 10^6$ | $9 \times 10^6$ |

| Ex. C. Ex. | Resin to be made antibacterial | Name of antibacterial agent particle | Antibacterial properties Transparency | Color | Pressure of extruder (Kg/cm²) 2 hours | Pressure of extruder (Kg/cm²) 24 hours |
|---|---|---|---|---|---|---|
| Ex. X-II-33 | Polystyrene | A2 | 100 | Achromatic (white) | 28 | 33 |
|  |  | B1-2 | 100 | Achromatic (white) | 28 | 33 |
|  |  | C1 | 100 | Achromatic (white) | 28 | 33 |
|  |  | D1 | 100 | Achromatic (white) | 28 | 33 |
|  |  | E1 | 100 | Achromatic (white) | 28 | 33 |
|  |  | F1 | 100 | Achromatic (white) | 28 | 33 |
|  |  | G1 | 100 | Achromatic (white) | 28 | 33 |
|  |  | H1 | 100 | Achromatic (white) | 29 | 36 |
| Ex. X-II-34 | Acrylic resin | A2 | 100 | Achromatic (white) | 28 | 33 |
|  |  | B1-2 | 100 | Achromatic (white) | 28 | 33 |
|  |  | C1 | 100 | Achromatic (white) | 28 | 33 |
|  |  | D1 | 100 | Achromatic (white) | 28 | 33 |
|  |  | E1 | 100 | Achromatic (white) | 28 | 33 |
|  |  | F1 | 100 | Achromatic (white) | 28 | 33 |
|  |  | G1 | 100 | Achromatic (white) | 28 | 33 |
|  |  | H1 | 100 | Achromatic (white) | 29 | 36 |
| C. Ex. X-II-5 | polystyrene | nil | 100 | Achromatic (white) | 27 | 30 |
| C. Ex. X-II-6 | polystyrene | V2 | 98 | Achromatic (white) | 28 | 33 |
| C. Ex. X-II-7 | polystyrene | Y1 | 98 | Achromatic (white) | 28 | 33 |

Ex.: Example,
C. Ex.: Comparative Example,
pbw: part by weight

Polycarbonate, Polyethylene Terephthalate, Nylon 6-6 and Polyacetal Resin Molded Articles Examples X-II-35 and X-II-36, and Comparative Examples X-II-8 and X-II-9

In Examples X-II-35 and X-II-36, tests were conducted in accordance with Example X-II-1 except that the resin to be made antibacterial was changed from polypropylene to resins which have transparency and need to have a low content of water at the time of processing, such as polycarbonate, polyethylene terephthalate, nylon 6-6 and polyacetal resins, the type and amount of the antibacterial agent and the amount of the fluorescent brightener were changed as shown in Table-9, and the kneading and molding temperatures were changed to normal resin processing temperatures (290° C. for PC, PET and nylon 6-6 and 190° C. for polyacetal).

0.1 part by weight of the dried particles A2, B1, C1, D1, E1, F1, G1 or H1 or the baked particles A17 or A18 were used as an antibacterial agent in Examples X-II-35 and X-II-36, no antibacterial agent was added in Comparative Example 8, and 0.1 part by weight of 400° C. or 500° C. baked particles V2 was used in Comparative Example 9. The measurement results of antibacterial properties, transparency, color and pressure of an extruder are shown in Table-9.

Molded articles obtained in Examples X-II-35 and X-II-36 had no silver streak.

As shown in Table-9 below, it was confirmed that molded articles of Examples were achromatic (white) and excellent in antibacterial properties (antibacterial action retention characteristics right after molding and after contact with tap water) with almost unimpaired transparency. On the other hand, antibacterial properties were not observed at all in Comparative Examples.

TABLE 9

| | | | | | Antibacterial properties | | |
|---|---|---|---|---|---|---|---|
| | | | | | | | Antibacterial action retention characteristics after contact with tap water at 90° C. (*Escherichia coli*) cfu/ml |
| | | | | | Antibacterial properties right after molding | | |
| Ex. C. Ex. | Resin to be made antibacterial | Name of antibacterial agent particle | Amount of antibacterial agent | Amount of fluorescent brightener (pbw) | *Escherichia coli* cfu/ml | *Staphylococcus aureus* cfu/ml | |
| Ex. X-II-35 | PC resin | A17 | 0.1 | 0.0001 | 10> | 10> | 10> |
| | | A18 | 0.1 | 0.0001 | 10> | 10> | 10> |
| | | A2 | 0.1 | 0.0001 | 10> | 10> | 10> |
| | | B1-2 | 0.1 | 0.0001 | 10> | 10> | 10> |
| | | C1 | 0.1 | 0.0001 | 10> | 10> | 10> |
| | | D1 | 0.1 | 0.0001 | 10> | 10> | 10> |
| | | E1 | 0.1 | 0.0001 | 10> | 10> | 10> |
| | | F1 | 0.1 | 0.0001 | 10> | 10> | 10> |
| | | G1 | 0.1 | 0.0001 | 10> | 10> | 10> |
| | | H1 | 0.1 | 0.0001 | $1 \times 10$ | $1 \times 10$ | $1 \times 10$ |
| Ex. X-II-36 | PET resin | A17 | 0.1 | 0.0001 | 10> | 10> | 10> |
| | Nylon 66 | A17 | 0.1 | 0.0001 | 10> | 10> | 10> |
| | Polyurethane | A17 | 0.1 | 0.0001 | 10> | 10> | 10> |
| | Polyacetal | A17 | 0.1 | 0.0001 | 10> | 10> | 10> |
| C. Ex. X-II-8 | PC resin | nil | 0 | 0.0001 | $2 \times 10^6$ | $2 \times 10^6$ | $2 \times 10^6$ |
| C. Ex. X-II-9 | PC resin | 400° C. baked product of particles V2 | 0.1 | 0.0001 | $2 \times 10^6$ | $2 \times 10^6$ | $2 \times 10^6$ |
| | | 500° C. baked product of particles V2 | 0.1 | 0.0001 | $2 \times 10^6$ | $2 \times 10^6$ | $2 \times 10^6$ |

| | | | Antibacterial properties | | | |
|---|---|---|---|---|---|---|
| | | | | | Pressure of extruder Kg/cm² | |
| Ex. C. Ex. | Resin to be made bacterial | Name of antibacterial agent particle | Transparency % | Color | 2 hours | 24 hours |
| Ex. X-II-35 | PC resin | A17 | 100 | Achromatic (white) | 43 | 47 |
| | | A18 | 100 | Achromatic (white) | 43 | 47 |
| | | A2 | 100 | Achromatic (white) | 43 | 47 |
| | | B1-2 | 100 | Achromatic (white) | 43 | 47 |
| | | C1 | 100 | Achromatic (white) | 43 | 47 |
| | | D1 | 100 | Achromatic (white) | 43 | 47 |
| | | E1 | 100 | Achromatic (white) | 43 | 47 |
| | | F1 | 100 | Achromatic (white) | 43 | 47 |
| | | G1 | 100 | Achromatic (white) | 43 | 47 |
| | | H1 | 100 | Achromatic (white) | 45 | 49 |
| Ex. X-II-36 | PET resin | A17 | 100 | Achromatic (white) | 38 | 41 |
| | Nylon 66 | A17 | 100 | Achromatic (white) | 37 | 40 |
| | Polyurethane | A17 | 100 | Achromatic (white) | 30 | 45 |
| | Polyacetal | A17 | 100 | Achromatic (white) | 33 | 37 |
| C. Ex. X-II-8 | PC resin | nil | 100 | Achromatic (white) | 42 | 45 |
| C. Ex. X-II-9 | PC resin | 400° C. baked product of particles V2 | 100 | Achromatic (white) | 43 | 47 |
| | | 500° C. baked product of particles V2 | 100 | Achromatic (white) | 43 | 47 |

Ex.: Example,

C. Ex.: Comparative Example, pbw: Part by weight

Films

Examples X-II-37 and Comparative Example X-II-10

100 wt % of the total of 90 wt % of LDPE resin and 10 wt % of the particles A2, B1, C1, D1, E1, F1, G1 or H1 as an antibacterial agent were kneaded together by a pressure kneader at 120° C. for 15 minutes, and the kneaded product was hot cut by an extrusion granulator at 120° C. to obtain a master batch pellet having a diameter of about 3 mm.

A 50 μm-thick film was formed from a mixture of the master batch pellet and LDPE resin before the formation of the master batch and having composition shown in Table-10 by a T die method or inflation method.

In Comparative Example X-II-10, a film was obtained out of LDPE resin alone before the formation of the master batch.

The antibacterial properties (antibacterial action retention characteristics right after molding and after contact with tap water), transparency and whiteness of the film were measured by the above methods. The results are shown in Table-10. In Comparative Example X-II-10, a film was prepared without adding an antibacterial agent and measured in the same manner as in Example X-II-37. The results are shown in Table-10.

As shown in Table-10 below, it was confirmed that the film of Example was achromatic (white) and excellent in antibacterial properties (antibacterial action retention characteristics right after molding and after contact with tap water) with unimpaired transparency. On the other hand, antibacterial properties were not observed at all in Comparative Example.

Example X-II-38

100 parts by weight each of polypropylene, LDPE, HDPE, ionomer resin, nylon 6/66 copolymer resin, PET resin or AS resin and 0.1 part by weight of the particles A2 were kneaded together by a double-screw kneading extruder to obtain a mixture pellet.

A 50 μm-thick film was obtained from the pellet by the T die method. The antibacterial properties (antibacterial action retention characteristics right after molding and after contact with tap water), transparency and whiteness of the film were measured by the above methods. The results are shown in Table-10.

It was confirmed that the films obtained in Examples were achromatic (white) and excellent in antibacterial properties (antibacterial action retention characteristics right after molding and after contact with tap water) with unimpaired transparency. On the other hand, antibacterial properties were not observed at all in Comparative Example.

TABLE 10

| | | | | Antibacterial properties | | |
|---|---|---|---|---|---|---|
| | | | | | Antibacterial properties | |
| Ex. C. Ex. | Resin to be made antibacterial | Name of antibacterial agent particle | Amount of antibacterial agent (pbw) | Amount of fluorescent brightener (pbw) | Antibacterial properties right after molding | | Antibacterial action Retention characteristics after contact with tap water at 70° C. (Escherichia coli) cfu/ml |
| | | | | | Escherichia coli cfu/ml | Staphylococcus aureus cfu/ml | |
| Ex. X-II-37 | LDPE | A2 | 0.1 | 0 | 10> | 10> | 10> |
| | | B1-2 | 0.1 | 0 | 10> | 10> | 10> |
| | | C1 | 0.1 | 0 | 10> | 10> | 10> |
| | | D1 | 0.1 | 0 | 10> | 10> | 10> |
| | | E1 | 0.1 | 0 | 10> | 10> | 10> |
| | | F1 | 0.1 | 0 | 10> | 10> | 10> |
| | | G1 | 0.1 | 0 | 10> | 10> | 10> |
| | | H1 | 0.1 | 0 | $1 \times 10$ | $1 \times 10$ | $1 \times 10$ |
| Ex. X-II-38 | Polypropylene, ionomer resin, polyurethane resin, nylon 6/66 copolymer resin, PET resin, AS resin | A2 | 0.1 | 0 | 10> | 10> | 10> |
| C. Ex. X-II-10 | LDPE | nil | 0 | 0 | $2 \times 10^6$ | $2 \times 10^6$ | $2 \times 10^6$ |

| Ex. C. Ex. | The resin to be made antibacterial | Name of antibacterial agent particle | Antibacterial properties Transparency % | Color |
|---|---|---|---|---|
| Ex. X-II-37 | LDPE | A2 | 100 | Achromatic (white) |
| | | B1-2 | 100 | Achromatic (white) |
| | | C1 | 100 | Achromatic (white) |
| | | D1 | 100 | Achromatic (white) |
| | | E1 | 100 | Achromatic (white) |
| | | F1 | 100 | Achromatic (white) |
| | | G1 | 100 | Achromatic (white) |
| | | H1 | 100 | Achromatic (white) |
| Ex. X-II-38 | Polypropylene, ionomer resin, polyurethane resin, nylon 6/66 | A2 | 100 | Achromatic (white) |

TABLE 10-continued

| | | | | |
|---|---|---|---|---|
| C. Ex. X-II-10 | copolymer resin, PET resin, AS resin LDPE | nil | 100 | Achromatic (white) |

Ex.: Example,
C. Ex.: Comparative Example,
pbw: Part by weight

PVC Molded Articles

Example X-II-39 and Comparative Example X-II-11

In Example X-II-39, a composition comprising 100 parts by weight of a polyvinyl chloride resin, 0.1 part by weight of antibacterial agent particles shown in Table-11, 1.2 parts by weight of octyltin mercapto, 0.8 part by weight of glycerin ricinoleate and 0.4 part by weight of montanic acid ester was kneaded by an open roll at 180° C. for 3 minutes, and the kneaded product was molded into a 2 mm-thick plate by a compression molding machine at 180° C.

The antibacterial properties (antibacterial action retention characteristics right after molding and after contact with tap water) of the molded plate were measured by the above method. The results are shown in Table-11.

In Comparative Example X-II-11, a composition comprising no antibacterial agent was molded into a 2 mm-thick plate likewise, and the same measurements were made on the plate. The results are shown in Table-11.

It was confirmed that the molded plate of Example was excellent in antibacterial properties (antibacterial action retention characteristics right after molding and after contact with tap water) and transparency as shown in Table-11 below. On the other hand, antibacterial properties were not observed at all in Comparative Example.

TABLE 11

| | | | | Antibacterial properties | | |
|---|---|---|---|---|---|---|
| | | | | | | Antibacterial action retention characteristics after contact with tap water |
| | Name of | Amount of | Amount of | Antibacterial properties right after molding | | |
| Ex. C. Ex. | antibacterial agent particle | antibacterial agent (%) | fluorescent brightener (pbw) | Escherichia coli cfu/ml | Staphylococcus aureus cfu/ml | at 70° C. (Escherichia coli) cfu/ml |
| Ex. X-II-39 | A2 | 0.1 | 0.0001 | 10> | 10> | 10> |
| | B1-2 | 0.1 | 0.0001 | 10> | 10> | 10> |
| | C1 | 0.1 | 0.0001 | 10> | 10> | 10> |
| | D1 | 0.1 | 0.0001 | 10> | 10> | 10> |
| | E1 | 0.1 | 0.0001 | 10> | 10> | 10> |
| | F1 | 0.1 | 0.0001 | 10> | 10> | 10> |
| | G1 | 0.1 | 0.0001 | 10> | 10> | 10> |
| | H1 | 0.1 | 0.0001 | $1 \times 10$ | $1 \times 10$ | $1 \times 10$ |
| C. Ex. X-II-11 | nil | 0 | 0.0001 | $2 \times 10^6$ | $2 \times 10^6$ | $2 \times 10^6$ |

| | | Antibacterial properties | |
|---|---|---|---|
| Ex. C. Ex. | Name of antibacterial agent particle | Transparency % | Color |
| Ex. X-II-39 | A2 | 100 | Achromatic (white) |
| | B1-2 | 100 | Achromatic (white) |
| | C1 | 100 | Achromatic (white) |
| | D1 | 100 | Achromatic (white) |
| | E1 | 100 | Achromatic (white) |
| | F1 | 100 | Achromatic (white) |
| | G1 | 100 | Achromatic (white) |
| | H1 | 100 | Achromatic (white) |
| C. Ex. X-II-11 | A2 | 100 | Achromatic (white) |

Ex.: Example,
C. Ex.: Comparative Example,
pbw: Part by weight

Thermosetting Resin Molded Articles

Example X-II-40 and Comparative Examples X-II-12 and X-II-13

In Example X-II-40, 100 parts by weight of an unsaturated polyester resin, 1 part by weight of antibacterial agent particles shown in Table-12, 3 parts by weight of a curing agent (HY951 of Ciba Specialty Chemical Co., Ltd.), 1 part by weight of stearic acid, 0.5 part by weight of an antioxidant (Irganox 1010 of Ciba Specialty Co., Ltd.), 0.001 part by weight of a fluorescent brightener and 150 parts by weight of aluminum hydroxide for artificial marble having an average secondary particle diameter of 30 μm and a BET specific surface area of 1 $m^2/g$ were kneaded together by a kneader, and the kneaded product was cured at 90° C. for 15 minutes to obtain a 2 mm-thick plate.

The antibacterial properties (antibacterial action retention characteristics right after molding and after contact with tap water) of the molded plate were measured by the above method. The results are shown in Table-12.

In Comparative Examples X-II-12 and X-II-13, 2 mm-thick molded plates were manufactured in the same manner as in Example X-II-40 except that no antibacterial agent was added and the particles R1 were used, respectively, and the same measurements were made on these plates. The results are shown in Table-12.

It was confirmed that the molded plate of Example was excellent in antibacterial properties (antibacterial action retention characteristics right after molding and after contact with tap water). On the other hand, antibacterial properties were not observed at all in Comparative Example X-II-12.

Although antibacterial properties were observed right after molding in Comparative Example X-II-13, it was verified that it had no antibacterial action retention characteristics after contact with tap water.

Example X-II-41

The procedure of Example X-II-40 was repeated except that the antibacterial agent particles were changed to the particles E2, the amount of the particles was changed to 300 parts by weight, and the amount of the stearic acid was changed to 3 parts by weight to manufacture a molded plate and carry out the same measurements on the plate. The results are shown in Table-12. It was confirmed that the molded plate had excellent antibacterial properties (antibacterial action retention characteristics right after molding and after contact with tap water).

Example X-II-42

The procedure of Example X-II-40 was repeated except that the resin to be made antibacterial was changed from the unsaturated polyester resin to a phenolic resin, melamine resin and epoxy resin and the antibacterial agent was changed to the particles E4 to manufacture a molded plate and carry out the same measurements on the plate. The results are shown in Table-12. The obtained molded plate had excellent antibacterial properties (antibacterial action retention characteristics right after molding and after contact with tap water).

The following can be understood from Examples X-II-40 to X-II-2 and Comparative Examples X-II-12 and X-II-13.

The antibacterial thermosetting resin products of the present invention can be advantageously used in artificial marble for use in toilets and bathrooms without losing their antibacterial properties (antibacterial action retention characteristics right after molding and after contact with tap water) for a long time.

On the other hand, in Comparative Example X-II-13 in which silver supporting zirconium phosphate in the prior art was used, antibacterial properties right after molding were observed but antibacterial action retention characteristics after contact with tap water were not observed at all. That is, this comparative example is of no significance in the above application field.

TABLE 12

| | | | | | Antibacterial properties | | |
|---|---|---|---|---|---|---|---|
| | | | | | | Antibacterial properties | |
| | | | | | | | Antibacterial action retention characteristics after contact with tap water |
| | | Name of | | Amount of | Antibacterial properties right after molding | | |
| Ex. C. Ex. | Resin to be made antibacterial | antibacterial agent particle | Amount of antibacterial agent | fluorescent brightener (pbw) | *Escherichia coli* cfu/ml | *Staphylococcus aureus* cfu/ml | at 90° C. (*Escherichia coli*) cfu/ml |
| Ex. X-II-40 | Unsaturated polyester resin | A2 | 1 | 0.001 | 10> | 10> | 10> |
| | | B1-2 | 1 | 0.001 | 10> | 10> | 10> |
| | | C1 | 1 | 0.001 | 10> | 10> | 10> |
| | | D1 | 1 | 0.001 | 10> | 10> | 10> |
| | | E1 | 1 | 0.001 | 10> | 10> | 10> |
| | | F1 | 1 | 0.001 | 10> | 10> | 10> |
| | | G1 | 1 | 0.001 | 10> | 10> | 10> |
| | | H1 | 1 | 0.001 | 10> | 10> | 10> |
| Ex. X-II-41 | Unsaturated polyester resin | E2 | 300 | 0.001 | $1 \times 10$ | $1 \times 10$ | $1 \times 10^2$ |
| Ex. X-II-42 | Phenolic resin, melamine resin, epoxy resin | E4 | 1 | 0.001 | 10> | 10> | 10> |
| C. Ex. X-II-12 | Unsaturated polyester resin | nil | 0 | 0.001 | $2 \times 10^6$ | $2 \times 10^6$ | $2 \times 10^6$ |

TABLE 12-continued

| C. Ex. X-II-13 | Unsaturated polyester resin | R1 | 1 | 0.001 | 10> | 10> | 1 × 10$^6$ |

| Ex. C. Ex. | Resin to be made antibacterial | Antibacterial properties | | |
|---|---|---|---|---|
| | | Name of antibacterial agent particle | Color | |
| Ex. X-II-40 | Unsaturated polyester resin | A2 | Achromatic (white) | |
| | | B1-2 | Achromatic (white) | |
| | | C1 | Achromatic (white) | |
| | | D1 | Achromatic (white) | |
| | | E1 | Achromatic (white) | |
| | | F1 | Achromatic (white) | |
| | | G1 | Achromatic (white) | |
| | | H1 | Achromatic (white) | |
| Ex. X-II-41 | Unsaturated polyester resin | E2 | Achromatic (white) | |
| Ex. X-II-42 | Phenolic resin, melamine resin, epoxy resin | E4 | Achromatic (white) | |
| C. Ex. X-II-12 | Unsaturated polyester resin | nil | Achromatic (white) | |
| C. Ex. X-II-13 | Unsaturated polyester resin | R1 | Achromatic (white) | |

Ex.: Example,
C. Ex.: Comparative Example,
pbw: Part by weight

Although the immersion time was extended to 720 hours in the test of antibacterial action retention characteristics after use of 90° C. tap water in Example X-II-40, the antibacterial properties (*Escherichia coli*) were still 10>cfu/ml, which means that high antibacterial properties were maintained. On the other hand, the antibacterial properties in Comparative Example X-II-14 were 2×10$^7$ cfu/ml in the same test, which means that antibacterial properties were not observed at all.

Rubber Molded Articles

Example X-II-43 and Comparative Example X-II-14

A composition comprising 100 parts by weight of EPDM (ethylene/propylene ratio=50/50), 0.5 part by weight of antibacterial agent particles shown in Table-13, 3 parts by weight of dicumyl peroxide, 0.5 part by weight of poly(2,2,4-trimethyl-1,2-dihydroquinone), 1 part by weight of a silane coupling agent (A-172 of Nippon Unicar Co., Ltd.), 0.5 part by weight of stearic acid, 1 part by weight of phosphor, 0.001 part by weight of a fluorescent brightener and 5 parts by weight of rutile titanium dioxide was kneaded by an open roll at 50° C., and the obtained kneaded product was cured at 160° C. for 30 minutes after one day to obtain a 2 mm-thick molded plate.

The antibacterial properties (antibacterial action retention characteristics right after molding and after contact with tap water) of the molded plate were measured by the above method. The results are shown in Table-13.

In Comparative Example X-II-14, a 2 mm-thick plate was obtained in the same manner as in Example X-II-43 except that no antibacterial agent was added, and the same measurements were made on the plate. The results are shown in Table-13.

It was confirmed that the molded plate of Example had excellent antibacterial properties (antibacterial action retention characteristics right after molding and after contact with tap water). On the other hand, antibacterial properties were not observed at all in Comparative Example X-II-14.

Example X-II-44

A molded plate was manufactured in the same manner as in Example X-II-43 except that the antibacterial agent particles were changed to the particles A14, the amount of the particles was changed to 200 parts by weight and the amount of stearic acid was changed to 2 parts by weight, and the same measurements were made on the plate. The results are shown in Table-13.

It was confirmed that the molded plate had excellent antibacterial properties (antibacterial action retention characteristics right after molding and after contact with tap water).

TABLE 13

| Ex. C. Ex. | Rubber to be antibacterial | Name of antibacterial agent particle | Amount of antibacterial agent (pbw) | Amount of fluorescent brightener (pbw) | Amount of titanium dioxide (pbw) | Antibacterial properties right after molding — *Escherichia coli* cfu/ml | Antibacterial properties right after molding — *Staphylococcus aureus* cfu/ml | Antibacterial action retention characteristics after contact with tap water at 70° C. (*Escherichia coli*) cfu/ml | Color |
|---|---|---|---|---|---|---|---|---|---|
| Ex. X-II-43 | EPDM | A2 | 0.5 | 0.001 | 5 | 10> | 10> | 10> | Achromatic (white) |
| | | B1-2 | 0.5 | 0.001 | 5 | 10> | 10> | 10> | Achromatic (white) |
| | | C1 | 0.5 | 0.001 | 5 | 10> | 10> | 10> | Achromatic (white) |
| | | D1 | 0.5 | 0.001 | 5 | 10> | 10> | 10> | Achromatic (white) |
| | | E1 | 0.5 | 0.001 | 5 | 10> | 10> | 10> | Achromatic (white) |
| | | F1 | 0.5 | 0.001 | 5 | 10> | 10> | 10> | Achromatic (white) |
| | | G1 | 0.5 | 0.001 | 5 | 10> | 10> | 10> | Achromatic (white) |
| | | H1 | 0.5 | 0.001 | 5 | 10> | 10> | 10> | Achromatic (white) |
| Ex. X-II-44 | EPDM | A14 | 300 | 0.001 | 5 | $1 \times 10$ | $1 \times 10$ | $1 \times 10$ | Achromatic (white) |
| C. Ex. X-II-14 | EPDM | nil | 0 | 0.001 | 5 | $2 \times 10^6$ | $2 \times 10^6$ | $2 \times 10^6$ | Achromatic (white) |

Ex.: Example
C. Ex.: Comparative Example
pbw: Part by weight

Fibers

Example X-II-45 and Comparative Example X-II-15

100 parts by weight of polypropylene for fibers and 2 parts by weight of the antibacterial agent particles A2 were pre-kneaded together by a double-screw kneading extruder, and the kneaded product was spun by a melting method using an extruder having a 300-mesh screen to obtain a 100-denier fiber. The antibacterial properties (antibacterial action retention characteristics right after molding and after contact with tap water) of the fiber were measured by the above method.

The results are shown in Table-14.

In Comparative Example X-II-15, a 100-denier fiber was manufactured in the same manner as in Example X-II-45 except that no antibacterial agent was added, and the same measurements were made on the fiber. The results are shown in Table-14.

It was confirmed that the fiber of Example had excellent antibacterial properties (antibacterial action retention characteristics right after spinning and after contact with tap water).

This means that the antibacterial properties are not lost or hardly lost even when fiber products such as globes and socks are washed several ten times or several hundred times.

In the above extrusion melting method, the spinning work was not impeded by the screen clogged up with coarse particles in Example.

TABLE 14

| Ex. C. Ex. | Fiber to be made antibacterial | Name of antibacterial agent particle | Amount of antibacterial agent | Amount of fluorescent brightener (pbw) | Antibacterial properties right after molding — *Escherichia coli* cfu/ml | Antibacterial properties right after molding — *staphylococcus aureus* cfu/ml | Antibacterial action retention characteristics after contact with tap water at 90° C. (*Escherichia coli*) cfu/ml | Color |
|---|---|---|---|---|---|---|---|---|
| Ex. X-II-45 | polypropylene fiber | A2 | 2 | 0.001 | 10> | 10> | 10> | Achromatic (white) |

TABLE 14-continued

<table>
<tr><th colspan="8">Antibacterial properties</th></tr>
<tr><th rowspan="3">Ex.<br>C. Ex.</th><th rowspan="3">Fiber to be made<br>antibacterial</th><th rowspan="3">Name of<br>antibacterial<br>agent<br>particle</th><th rowspan="3">Amount of<br>antibacterial<br>agent</th><th rowspan="3">Amount of<br>fluorescent<br>brightener<br>(pbw)</th><th colspan="3">Antibacterial properties</th><th rowspan="3">Color</th></tr>
<tr><th colspan="2">Antibacterial properties<br>right after molding</th><th>Antibacterial action<br>retention characteristics<br>after contact<br>with tap water at</th></tr>
<tr><th>Escherichia<br>coli<br>cfu/ml</th><th>staphylococcus<br>aureus<br>cfu/ml</th><th>90° C.<br>(Escherichia coli)<br>cfu/ml</th></tr>
<tr><td>C. Ex. X-II-15</td><td>polypropylene<br>fiber</td><td>nil</td><td>0</td><td>0.001</td><td>2 × 10⁶</td><td>2 × 10⁶</td><td>3 × 10⁶</td><td>Achromatic<br>(white)</td></tr>
</table>

Ex.: Example
C. Ex.: Comparative Example
pbw: Part by weight

Although the immersion time was extended to 720 hours in the test of antibacterial action retention characteristics after use of 90° C. tap water (*Escherichia coli*) in Example X-II-45, the antibacterial properties were still 10>cfu/ml, which means that high antibacterial properties were maintained.

Nonwoven Fabrics

Example X-II-46 and Comparative Example X-II-16

The polypropylene fibers obtained in Example X-II-45 and Comparative Example X-II-15 were formed into nonwoven fabrics having a density of 0.06 g/cm³ by a papermaking web method and random web method, and the above antibacterial property test was made on these fabrics. An excellent antibacterial effect (antibacterial action retention characteristics right after molding and after contact with tap water) was obtained in Example. On the other hand, antibacterial properties were not observed at all in Comparative Example. The results are shown in Table-15.

TABLE 15

<table>
<tr><th colspan="9">Antibacterial properties</th></tr>
<tr><th rowspan="3">Ex.<br>C. Ex.</th><th rowspan="3">Nonwoven fabrics<br>to be made<br>antibacterial</th><th rowspan="3">Name of<br>antibacterial<br>agent particle</th><th rowspan="3">Amount of<br>antibacterial<br>agent</th><th rowspan="3">Amount of<br>fluorescent<br>brightener<br>(pbw)</th><th colspan="3">Antibacterial properties</th><th rowspan="3">Color</th></tr>
<tr><th colspan="2">Antibacterial properties<br>right after molding</th><th>Antibacterial<br>action<br>retention<br>characteristics<br>after contact<br>with tap water at<br>70° C.</th></tr>
<tr><th>Escherichia<br>coli<br>cfu/ml</th><th>Staphylococcus<br>aureus<br>cfu/ml</th><th>(Escherichia<br>coli)<br>cfu/ml</th></tr>
<tr><td>Ex. X-II-46</td><td>polypropylene<br>nonwoven fabric</td><td>A2</td><td>2</td><td>0.001</td><td>10></td><td>10></td><td>10></td><td>Achromatic<br>(white)</td></tr>
<tr><td>C. Ex. X-II-16</td><td>polypropylene<br>nonwoven fabric</td><td>nil</td><td>0</td><td>0.001</td><td>2 × 10⁶</td><td>2 × 10⁶</td><td>2 × 10⁶</td><td>Achromatic<br>(white)</td></tr>
</table>

Ex.: Example
C. Ex.: Comparative Example
pbw: Part by weight

Coatings

Example X-II-47 and Comparative Example X-II-17

60 parts by weight of methyl methacrylate, 40 parts by weight of 2-ethylhexyl acrylate, 3 parts by weight of triethylene glycol dimethacrylate, 10 parts by weight of dialkyl phthalate, 0.003 part by weight of hydroquinone, 0.5 part by weight of paraffin wax having a melting point of 46° C., 0.5 part by weight of paraffin wax having a melting point of 54° C. and 0.7 part by weight of N,N-di-8-hydroxypropyl-9-P toluidine based on 100 parts by weight of methyl methacrylate and 2-ethylhexyl acrylate were injected into an apparatus equipped with a cooling unit, and 25 parts by weight of a copolymer of methyl methacrylate and n-butyl methacrylate (Tg=66° C., Mw=40,000) was injected into the apparatus little by little under agitation, stirred at 60° C. for 2 hours and cooled to 30° C.

A coating comprising 1 part by weight of the particles A2 of Example X-I-2, 7 parts by weight of the Toner P-400 of Mitsubishi Rayon Co., Ltd. as a colorant, 300 parts by weight of the KM17 of Mitsubishi Rayon Co., Ltd. as an aggregate and 2 parts by weight of diacyl peroxide as a polymerization initiator was left at 20° C. for 1 hour to form a coating film, and an antibacterial property test was made on the film by the method (c) in the above paragraph (7). The results are shown in Table-16.

In Comparative Example X-II-17, a coating comprising no antibacterial agent was applied in the same manner as in Example X-II-47 to carry out the same measurements. The results are shown in Table-16.

It was confirmed that the coating of Example had excellent antibacterial properties (antibacterial action retention characteristics right after molding and after contact with tap water). On the other hand, antibacterial properties were not observed at all in Comparative Example.

TABLE 16

| | | | | | Antibacterial properties | | | |
|---|---|---|---|---|---|---|---|---|
| | | | | | | | Antibacterial properties | |
| | | | | | | | Antibacterial action retention characteristics after contact with tap water at 70° C. | |
| | | | | | Antibacterial properties right after molding | | | |
| | | Name of | | Amount of | | | | |
| Ex. C. Ex. | Coating to be made antibacterial | antibacterial agent particle | Amount of antibacterial agent | fluorescent brightener (pbw) | *Escherichia coli* cfu/ml | *Staphylococcus aureus* cfu/ml | (*Escherichia coli*) cfu/ml | Color |
| Ex. X-II-47 | Synthetic resin coating (urethane) | A2 | 1 | 0.001 | 10> | 10> | 10> | Achromatic (white) |
| C. Ex. X-II-17 | Synthetic resin coating (urethane) | nil | 0 | 0.001 | 2 × 10$^6$ | 2 × 10$^6$ | 2 × 10$^6$ | Achromatic (white) |

Ex.: Example

C. Ex.: Comparative Example pbw: Part by weight

Caulking Materials

Example X-II-48 and Comparative Example X-II-18

100 parts by weight of polydimethylsiloxane having a viscosity at 25° C. of 50,000 centipoise and a silanol group at a terminal and 1 part by weight of γ-aminopropyl bis(methylethylketoxyamino)methoxysilane were mixed together under vacuum for 10 minutes, 5 parts by weight of methyl tris (methylethylketoxyamino) silane was added to and mixed with the resulting mixture under vacuum for 15 minutes, and 5 parts by weight of fumed silica having a BET specific surface area of 200 m$^2$/g, 0.1 part by weight of dibutyltin laurate and 1 part by weight of the antibacterial agent particles A2 were added to the mixture under vacuum for 10 minutes.

This mixed composition was dropped on a polyethylene sheet to obtain a 2 mm-thick test piece for an antibacterial property test. An antibacterial property test was made on this test piece by the above method (e) in the paragraph (7). The results are shown in Table-17. In Comparative Example, a caulking material was prepared from a composition comprising no antibacterial agent, and the same measurements were made on the caulking material. The results are shown in Table-17.

It was confirmed that the caulking material of Example had excellent antibacterial properties (antibacterial action retention characteristics right after molding and after contact with tap water). On the other hand, antibacterial properties were not observed at all in Comparative Example.

Therefore, it is found that the antibacterial resin composition of the present invention and products formed from the composition have high safety and excellent thermal deterioration resistance.

Antifungal Agents

Example X-II-49 and Comparative Examples X-II-19 and X-II-20

As for the minimum growth prevention concentration in the standard method of the Japanese Society of Chemotherapy (2003 revised version) whose culture medium was changed from a sensitive MHB culture medium to a potato dextrose agar medium manufactured by Nissui Pharmaceutical Co., Ltd., the antifungal performances of the antifungal agent particles of the present invention and the particles of Comparative Example were measured and expressed in ppm as the minimum growth prevention concentrations. As this numerical value becomes smaller, the antifungal performance becomes higher.

The measurement results are shown in Table-18 below. The fungi used are *1: Caldosporium Caldosporides NBRC 6348 (black leather mold), *2: Colletotricum coccodes NBRC 5256 (black dot root rot) and *3: Ustilaginoidia virens NBRC 9175 (false smut).

TABLE 17

| | | | | Antibacterial properties | | | |
|---|---|---|---|---|---|---|---|
| | | | | | Antibacterial properties | | |
| | | | | Antibacterial properties right after molding | | Antibacterial action Retention characteristics after contact with tap water at 70° C. | |
| Ex. C. Ex. | Name of Resin to be made antibacterial | Name of antibacterial agent particle | Amount of antibacterial agent | Amount of fluorescent brightener (pbw) | *Escherichia coli* cfu/ml | *Staphylococcus aureus* cfu/ml | (*Escherichia coli*) cfu/ml | Color |
| Ex. X-II-48 | Polydimethylsiloxane | A2 | 1 | 0.001 | 10> | 10> | 10> | Achromatic (white) |
| C. Ex. X-II-18 | Polydimethylsiloxane | nil | 0 | 0.001 | 2 × 10$^6$ | 2 × 10$^6$ | 2 × 10$^6$ | Achromatic (white) |

Ex.: Example
C. Ex.: Comparative Example
pbw: Part by weight

When ashes obtained by burning the above molded articles, films, etc. of Examples X-II-1 to X-II-48 at 900° C. were dissolved in sulfuric acid and nitric acid to prepare a solution so as to measure heavy metals contained in the molded articles, films, etc. of Examples by atomic absorption spectrophotometry, ICP-AES (Inductively Coupled Plasma-Atomic Emission Spectroscopy) or fluorescent X-ray spectroscopy, the contents of Pb, Cd, As and Ba in the resin molded articles, films and fibers of Examples X-II-1 to X-II-48 were all 0.1 ppm or less, the content of Fe was 5 ppm or less, and the contents of Mn, Cu, Cr and Ni were each 1 ppm or less.

TABLE 18

| | | Fungi minimum growth prevention concentration (ppm) | | |
|---|---|---|---|---|
| | Antifungal agent | *1 | *2 | *3 |
| Ex. | Particle A1 | 300 or less | 30 or less | 15 or less |
| | Particle B1-1 | 300 or less | 30 or less | 15 or less |
| | Particle C1 | 300 or less | 30 or less | 15 or less |
| | Particle D1 | 300 or less | 30 or less | 15 or less |
| | Particle E1 | 300 or less | 30 or less | 15 or less |
| | Particle F1 | 300 or less | 30 or less | 15 or less |
| | Particle G1 | 300 or less | 30 or less | 15 or less |

TABLE 18-continued

| Antifungal agent | Fungi minimum growth prevention concentration (ppm) | | |
|---|---|---|---|
| | ※1 | ※2 | ※3 |
| Particle H1 | 300 or less | 30 or less | 15 or less |
| Particle B1-2 | 300 or less | 30 or less | 15 or less |
| Comparative Example X-II-19 Particles R1 (silver supporting zirconium phosphate) Average secondary particle diameter; 1 µm BET specific surface area; 4 m²/g Content of Ag; 3% ※The particles R1 were also used in the following experiments. | 6400 | 3000 | 20 |
| Comparative Example X-II-20 Bordeaux scatter powders (commercially available Bordeaux scatter powder containing 11.1% of copper sulfate and 6.0% of copper) | 6400< | 6400< | 800 |

Ex.: Example

It was found that the antifungal agent of the present invention shows much higher antifungal performance than the antifungal agents of Comparative Examples.

Cosmetics

Example X-II-50 and Comparative Example X-II-21

Water-in-oil type creamy emulsion cosmetics comprising the components of Example and Comparative Example shown in Table-19 below were prepared. A mixture of oily materials denoted by 1 to 5, surfactants denoted by 6 and 7 and an antibacterial agent denoted by 10 was designated as A, a mixture of purified water denoted by 8 and a humectant denoted by 9 was designated as B, the mixtures A and B were heated at 70° C., the mixture B was poured into the mixture A under agitation, and the resulting product was emulsified and then cooled. An antibacterial property test was carried out 30 days after emulsification by using *E. coli* NBRC 3972 in accordance with the method (c) in the above paragraph (7). Further, 1 g of each of the creams of Example and Comparative Example was applied to the armpit of a person always giving off a bad smell from under his/her arms, and 10 people were asked to check whether the person was still giving off a bad smell or not after 8 hours. The measurement results are shown in Table-19 below.

TABLE 19

| No. | Substance | role | | Examples II-50 | | | | | | | | C. Ex. II-21 | |
|---|---|---|---|---|---|---|---|---|---|---|---|---|---|
| 1 | Dodecyl isostearate | oil | | 25 | | | | | | | | 25 | |
| 2 | Squalane | oil | | 15 | | | | | | | | 15 | |
| 3 | Bees wax | oil | | 8 | | | | | | | | 8 | |
| 4 | Cholesteryl hydroxystearate | oil | | 0.2 | | | | | | | | 0.2 | |
| 5 | Shea butter | oil | | 5 | | | | | | | | 5 | |
| 6 | decaglyceryl pentaoleate | surfactant | | 3 | | | | | | | | 3 | |
| 7 | decaglyceryl diisostearate | surfactant | | 1 | | | | | | | | 1 | |
| 8 | purified water | matrix | | balance | | | | | | | | balance | |
| 9 | glycerin | humectant | | 3 | | | | | | | | 3 | |
| 10 | Examples Particle A1 | antibacterial agent | 0.5 | 0 | 0 | 0 | 0 | 0 | 0 | 0 | 0 | 0 | 0 |
| | Particle B1-1 | antibacterial agent | 0 | 0.5 | 0 | 0 | 0 | 0 | 0 | 0 | 0 | 0 | 0 |
| | Particle C1 | antibacterial agent | 0 | 0 | 0.5 | 0 | 0 | 0 | 0 | 0 | 0 | 0 | 0 |
| | Particle D1 | antibacterial agent | 0 | 0 | 0 | 0.5 | 0 | 0 | 0 | 0 | 0 | 0 | 0 |
| | Particle E1 | antibacterial agent | 0 | 0 | 0 | 0 | 0.5 | 0 | 0 | 0 | 0 | 0 | 0 |
| | Particle F1 | antibacterial agent | 0 | 0 | 0 | 0 | 0 | 0.5 | 0 | 0 | 0 | 0 | 0 |
| | Particle G1 | antibacterial agent | 0 | 0 | 0 | 0 | 0 | 0 | 0.1 | 0 | 0 | 0 | 0 |
| | Particle H1 | antibacterial agent | 0 | 0 | 0 | 0 | 0 | 0 | 0 | 1 | 0 | 0 | 0 |
| | Particle B1-2 | antibacterial agent | 0 | 0 | 0 | 0 | 0 | 0 | 0 | 1 | 0 | 0 | 0 |
| | Particle R1 | antibacterial agent | 0 | 0 | 0 | 0 | 0 | 0 | 0 | 0 | 0.5 | 0 | |
| *Escherichia coli* NBRC3972 cfu/ml | | | 10> | 10> | 10> | 10> | 10> | 10> | 10> | 10> | $1 \times 10^6$ | $2 \times 10^6$ | |
| number of people who smell a bad smell | | | 0/10 | 0/10 | 0/10 | 0/10 | 0/10 | 0/10 | 0/10 | 0/10 | 10/10 | 10/10 | |

C. Ex.: Comparative Example

As a result of experiments, it was found that the cosmetic of Example had excellent antibacterial properties and a large effect of suppressing a bad smell. When the cosmetic was applied to the face in the present invention, it did not feel rough. Particularly when a cosmetic comprising disk-like particles (particles A1) was applied to the face, it spread very smoothly. On the other hand, although Comparative Example differs from Example only in that the antibacterial agent was changed to the particles R1 or that no antibacterial agent was added at all, it was found that the cosmetic of Comparative Example had no antibacterial properties and no effect of preventing a bad smell.

Antibacterial Deodorizing Sprays

Example X-II-51 and Comparative Examples X-II-21 and X-II-22

2.3 parts by weight of dipropylene glycol was injected into a container heated at 70° C., and further 2.5 parts by weight of lauric acid, 1 part by weight of myristic acid and 3.2 parts by weight of triethanolamine were added to the container to prepare a solution.

This solution was added to 90 parts by weight of ion exchange water heated at 70° C. little by little to be emulsified so as to prepare a foam matrix solution which was then cooled to 25° C.

1 part by weight of the antibacterial agent particles of the present invention was added to and mixed with the foam matrix solution under agitation to prepare an antibacterial deodorizing foam aerosol composition.

180 g of this composition and 20 g of an injection agent (LPG 0.34 MPa) were charged into a spray tin can to prepare an antibacterial deodorizing foam aerosol spray.

After a person always giving off a bad smell from under his/her arms took plenty of exercise, his/her sweat were collected with a cotton handkerchief measuring 15 cm×15 cm so as to be increasing by weighing 0.5 g and 5 g respectively. After 1 g of the antibacterial deodorizing foam aerosol spray was applied to the front and rear sides of the handkerchief which was then left in a thermostat tank at 30° C. for 10 days, 10 people were asked to smell the handkerchief. The measurement results are shown in Table-20 below.

TABLE 20

| An increase in weight of handkerchief, antibacterial agent | | odor test people who smell a bad smell | |
|---|---|---|---|
| An increase in weight of handkerchief | | 0.5 g | 5 g |
| Example X-II-51 | Particle A1 1 pbw | 0/10 | 0/10 |
| | Particle B1-1 1 pbw | 0/10 | 0/10 |
| | Particle C1 1 pbw | 0/10 | 0/10 |
| | Particle D1 1 pbw | 0/10 | 0/10 |
| | Particle E1 1 pbw | 0/10 | 0/10 |
| | Particle F1 1 pbw | 0/10 | 0/10 |
| | Particle G1 1 pbw | 0/10 | 0/10 |
| | Particle H1 1 pbw | 0/10 | 0/10 |
| | Particle BI-2 1 pbw | 0/10 | 0/10 |
| Comparative Example X-II-21 particles R1 (silver supporting zirconium phosphate) 1 pbw | | 5/10 | 10/10 |
| Comparative Example X-II-22 (without an antibacterial agent) | | 10/10 | 10/10 |

It was found that the antibacterial agent of the present invention showed much higher bad smell prevention performance than the antibacterial agent of Comparative Example.

Antibacterial Paper

Example X-II-52 and Comparative Examples X-II-23 and X-II-24

1% of the antibacterial agent of the present invention, 5% of starch (dry paper reinforcing agent), 5% of urea-formaldehyde resin (wet paper reinforcing agent), 2% of titanium dioxide (inorganic filler) and 5% of a polyamide resin-based ink (adhesive binder) were mixed into 82% of bleached chemical pump to make 0.1 mm-thick paper by a paper machine. A 5 cm×5 cm piece was cut out from this paper to carry out an antibacterial property test on the piece in accordance with the above method (a) in the paragraph (7). The results are shown in Table-21 below.

TABLE 21

| Antibacterial agent | | Antibacterial test Escherichia coli E. coli NBRC3972 number of colony cfu/ml |
|---|---|---|
| Example X-II-52 | Particle A1 5% | 10> |
| | Particle B1-1 5% | 10> |
| | Particle C1 5% | 10> |
| | Particle D1 5% | 10> |
| | Particle E1 5% | 10> |
| | Particle F1 5% | 10> |
| | Particle G1 5% | 10> |
| | Particle H1 5% | 10> |
| | Particle BI-2 5% | 10> |
| Comparative Example X-II-23 particles R1 (silver supporting zirconium phosphate) 5% | | $1 \times 10^5$ |
| Comparative Example X-II-24 (without an antibacterial agent) 0% | | $2 \times 10^6$ |

It was found that the antibacterial agent of the present invention showed much higher antibacterial properties than the antibacterial agents of Comparative Examples.

Agricultural Chemicals (Antifungal Agents)

Example X-II-53 and Comparative Examples X-II-25 and X-II-26

In Example, 10 parts by weight of the particles of the present invention, 30 parts by weight of surface modifying precipitated calcium carbonate as a silane coupling agent (inorganic powder), 5 parts by weight of polyoxyethylene alkyl allyl ether (surfactant), 10 parts by weight of ethylene glycol (surfactant), 0.2 part by weight of xanthane rubber (emulsification stabilizer) and 44.8 parts by weight of water were uniformly mixed together by a homomixer, and the resulting mixture was uniformly wet ground by a ball mill to obtain an aqueous suspended agricultural chemical composition. This was diluted with water to 1/100 and injected into a commercially available plastic spray.

In Comparative Examples, the procedure of Example was repeated except that the following particles or Bordeaux scatter powder was used in place of the particles of Example.

Meanwhile, an eggplant and a rice plant grown as large as about 20 cm were prepared.

1 g of a suspension of Colletotricum coccodes NBRC 5256 (bacterium of black dot root rot) having $1 \times 10^6$ cfu/ml was sprayed over the leaf, stem and base of the eggplant, 1 g of the above aqueous suspended agricultural chemical composition diluted to 1/100 was sprayed after one day, and an outbreak of black dot root rot in the eggplant was checked after 30 days. The test on the eggplant was carried out by putting soil into a pot having a diameter of 33 cm and a depth of 30 cm to a height of 27 cm.

1 g of a suspension of Ustilaginoidia virens NBRC 9175 (bacterium of false smut) having $1 \times 10^6$ cfu/ml was sprayed over the leaf, stem and base of the rice plant, 1 g of the aqueous suspended agricultural chemical composition diluted to 1/100 was sprayed after 1 day, and an outbreak of false smut in the rice plant was checked after 30 days. The test on the rice plant was carried out by putting soil into a pot having a diameter of 33 cm and a depth of 30 cm to a height of 27 cm under the condition that water barely covered the surface of the soil but a sufficient amount of water was existent in the soil. The measurement results are shown in Table-22 below.

TABLE 22

| Antifungal agents | | Plant | |
|---|---|---|---|
| | | eggplant black dot root rot | rice plant false smut |
| Example Antifungal agents used in present invention | Particle A1 | Not observed Grown well | Not observed Grown well |
| | Particle B1-1 | Not observed Grown well | Not observed Grown well |
| | Particle C1 | Not observed Grown well | Not observed Grown well |
| | Particle D1 | Not observed Grown well | Not observed Grown well |
| | Particle E1 | Not observed Grown well | Not observed Grown well |
| | Particle F1 | Not observed Grown well | Not observed Grown well |
| | Particle G1 | Not observed Grown well | Not observed Grown well |
| | Particle H1 | Not observed Grown well | Not observed Grown well |
| | Particle B1-2 | Not observed Grown well | Not observed Grown well |
| Comparative Example particles R1 (silver supporting zirconium phosphate) | | Observed in the whole root and withered | Observed in the whole root and withered |
| Comparative Example (Bordeaux scatter powder) (commercially available Bordeaux scatter powder containing 11.1% of copper sulfate and 6.0% of copper) | | Observed in the whole root and withered | Observed in the whole root and withered |

It was found that the agricultural chemical composition of the present invention showed much higher agricultural chemical performance than the agriculture chemical compositions of Comparative Examples.

The method of manufacturing antibacterial agent particles represented by the formula (Y-I) and use thereof will be described in detail based on the following examples.

Manufacture of Spherical Particle Antibacterial Agent

Example Y-I-1-1

Manufacture of Particles Y-A-1-1[$Ag_{0.1}Na_{0.86}$]$_{0.96}Al_3(SO_4)_{1.92}(OH)_{6.12}$ 508 ml of aluminum sulfate having a concentration of 1.025 mol/l and 73.84 g (0.52 mol) of sodium sulfate were dissolved in deionized water to prepare 2,000 ml of a solution, and 615 ml of 3.382 N sodium hydroxide was added to the solution under agitation over about 4 minutes at room temperature (alkali equivalent ratio: 0.999, (sulfate having a monovalent cation)/(aluminum sulfate)=1.0). After 20 minutes of agitation, the resulting solution was transferred to an autoclave to be subjected to a hydrothermal treatment at 170° C. for 2 hours, cooled to 25° C., filtered, rinsed with 500 ml of water and dried at 105° C. for 22 hours to obtain spherical aluminum sulfate hydroxide particles.

100 g of the sample was collected and suspended in 600 ml of a silver sulfate aqueous solution having a concentration of 0.025 mol/l and stirred under shaded light at 25° C. for 1 hour to carry out ion exchange between some of sodium ions and silver ions.

The sample after ion exchange was filtered, rinsed, dried (105° C.×6 hours+200° C.×1 hour) and ground.

Spherical silver-containing aluminum sulfate hydroxide particles Y-A-1-1 were obtained through these steps.

The properties of the particles Y-A-1-1 are shown in Table-23 and an SEM photomicrograph of the particles is shown in FIG. 15.

Example Y-I-1-2

2.6 g of zinc sulfate heptahydrate (first-grade reagent of Wako Pure Chemical Industries, Ltd.) and 2.2 g of ammonium sulfate (first-grade reagent of Wako Pure Chemical Industries, Ltd.) were added to 1,000 ml of ion exchange water heated at 80° C. to prepare a mixed solution.

95 g of the particles Y-A-1-1 was added to the mixed solution, stirred for 6 hours, dehydrated, rinsed and dried to obtain particles Y-A-1-2 treated with zinc and ammonium.

Although each of the particles had a Zn content of 0.1%, a $NH_3$ content of 0.4% and a BET specific surface area of 60 $mm^2/g$, other properties were the same as those of the particles Y-A-1-1.

Thereafter, the same treatment was made on the particles Y-A-3, Y-A-5, Y-A-8, Y-A-10, Y-A-11 and Y-A-31 to obtain the treated particles. All the treated particles had a Zn content of 0.1% and a $NH_4$ content of 0.4%. Although the BET specific surface areas of the treated particles were about 6 times larger than those of the particles before the treatment, the treated particles had almost the same average secondary particle diameters, particle size uniformity, particle shapes and other particle properties as those of the particles before the treatment. The whiteness of a resin composition obtained by adding the treated particles to a resin was further improved as compared with a resin composition obtained by adding the particles before the treatment to a resin.

Example Y-I-2

Manufacture of Particles Y-A-2[$Ag_{0.1}Na_{1.02}$]$_{1.12}Al_3(SO_4)_{2.17}(OH)_{5.78}$ The procedure of Example Y-I-1 was repeated except that the alkali equivalent ratio was changed to 0.95 to obtain particles Y-A-2.

Example Y-I-3

Manufacture of Particles Y-A-3[$Ag_{0.1}Na_{1.04}$]$_{1.14}Al_3(SO_4)_{2.30}(OH)_{5.54}$ The procedure of Example Y-I-1 was repeated except that the alkali equivalent ratio was changed to 0.90 to obtain particles Y-A-3.

Example Y-I-4

Manufacture of Particles Y-A-4[$Ag_{0.1}Na_{1.01}$]$_{1.11}Al_3(SO_4)_{2.33}(OH)_{5.45}$ The procedure of Example Y-I-1 was repeated except that the alkali equivalent ratio was changed to 0.835 to obtain particles Y-A-4. A SEM photomicrograph of the synthesized spherical particles Y-A-4 is shown in FIG. 16.

Example Y-I-5

Manufacture of Particles Y-A-5[$Ag_{0.1}Na_{0.96}$]$_{1.06}Al_3(SO_4)_{2.35}(OH)_{5.36}$ 445 ml of aluminum sulfate having a concentration of 1.025 mol/l and 64.61 g (0.455 mol) of sodium sulfate were dissolved in deionized water to prepare 2,000 ml of a solution, and 486 ml of 3.382 N sodium hydroxide was added to the solution under agitation at room temperature over about 4 minutes (alkali equivalent ratio: 0.9). After 20 minutes of agitation, the resulting solution was transferred to an autoclave to be subjected to a hydrothermal reaction at 100° C. for 29 hours, cooled to 25° C., filtered, rinsed with 500 ml of water and dried at 105° C. for 22 hours to obtain spherical aluminum sulfate hydroxide particles.

The subsequent steps were carried out in accordance with Example Y-I-1 except that 0.02 g of a polyacrylamide-based polymer coagulant (Sumifloc FN-20 of Sumitomo Chemical Co., Ltd.) was added after ion exchange and stirred for 10 minutes to obtain particles Y-A-5. A SEM photomicrograph of the synthesized spherical silver-containing aluminum sulfate hydroxide particles is shown in FIG. 17.

Example Y-I-6

Manufacture of Particles Y-A-6[$Ag_{0.3}Na_{0.94}$]$_{1.04}Al_3$ $(SO_4)_{2.34}(OH)_{5.36} \cdot 0.64H_2O$ The procedure of Example Y-I-5 was repeated except that the alkali equivalent ratio was changed to 0.835 and the drying conditions after ion exchange with silver ions were changed to 105° C. and 6 hours to obtain particles Y-A-6.

Example Y-I-7

Manufacture of Particles Y-A-7[$Ag_{0.1}Na_{0.97}$]$_{1.07}Al_3$ $(SO_4)_{2.32}(OH)_{5.43}$ The procedure of Example Y-I-5 was repeated except that (sulfate having a monovalent cation)/(aluminum sulfate)= 0.33, the reaction temperature was changed to 200° C. and the reaction time was changed to 1.5 hours to obtain particles Y-A-7.

Example Y-I-8

Manufacture of Particles Y-A-8[$Ag_{0.1}Na_{0.99}$]$_{1.09}Al_3$ $(SO_4)_{2.30}(OH)_{5.49}$ The procedure of Example Y-I-5 was repeated except that (sulfate having a monovalent cation)/(aluminum sulfate)= 2.0, the reaction temperature was changed to 250° C. and the reaction time was changed to 1 hour to obtain particles Y-A-8.

Example Y-I-9

Manufacture of particle Y-A-9[$Ag_{0.1}K_{1.10}$]$_{1.20}Al_3$ $(SO_4)_{2.20}(OH)_{5.80}$ 378 ml of aluminum sulfate having a concentration of 1.025 mol/l and 67.95 g (0.39 mol) of potassium sulfate were dissolved in deionized water to prepare 1,500 ml of a solution, and 596 ml of 2.34 N potassium hydroxide was added to the solution under agitation over about 4 minutes at room temperature (alkali equivalent ratio: 0.9). After 20 minutes of agitation, the resulting solution was transferred to an autoclave to be subjected to a hydrothermal reaction at 170° C. for 2 hours. The reaction product was cooled to 25° C., filtered, rinsed with 500 ml of water and dried at 105° C. for 22 hours to obtain spherical aluminum sulfate hydroxide particles. The subsequent steps were carried out in accordance with Example Y-I-1 to obtain particles Y-A-9.

Example Y-I-10

Manufacture of Particles Y-A-10[$Ag_{0.1}Na_{0.45}K_{0.45}$]$_1$ $Al_3(SO_4)_{1.99}(OH)_{6.02}$ 257 ml of aluminum sulfate having a concentration of 1.025 mol/l, 17.18 g (0.13 mol) of sodium sulfate and 22.65 g (0.13 mol) of potassium sulfate were dissolved in deionized water to prepare 500 ml of a solution, and 140 ml of 3.382 N sodium hydroxide and 140 ml of 3.382 N potassium hydroxide were added to the solution under agitation over about 1 minute at room temperature (alkali equivalent ratio: 0.9). After 20 minutes of agitation, the resulting solution was transferred to an autoclave to be subjected to a hydrothermal reaction at 170° C. for 2 hours. The reaction product was cooled to 25° C., filtered, rinsed with 500 ml of water and dried at 105° C. for 22 hours to obtain spherical aluminum sulfate hydroxide particles.

The subsequent steps were carried out in accordance with Example Y-I-1 to obtain particles Y-A-10.

Example Y-I-11

Manufacture of Particles Y-A-11[$Ag_{0.1}Na_{0.9}$]$_1$ $Ti_{0.01}Al_{2.94}(SO_4)_2(OH)_{5.86}$ The procedure of Example Y-1-1 was repeated except that 6.53 g of titanium sulfate {$Ti_2(SO_4)_3$} was further added to the aluminum sulfate aqueous solution of Example Y-I-1 and the ion exchange treatment temperature was changed to 60° C. to obtain particles Y-A-11.

Example Y-I-12

Manufacture of Particles Y-A-12[$Ag_{0.1}Na_{0.9}$]$_1Al_3$ $(SO_4)_{2.2}(PO_4)_{0.1}(OH)_{5.4}$ 378 ml of aluminum sulfate having a concentration of 1.03 mol/l and 36.93 g of sodium sulfate were dissolved in deionized water to prepare 1,400 ml of a solution, 413 ml of an aqueous solution of 3.4 N sodium hydroxide was added to the solution under agitation over about 4 minutes at room temperature. After 30 minutes of agitation, an aqueous solution obtained by dissolving 9.9 g of sodium phosphate dodecahydrate ($Na_3PO_4 \cdot 12H_2O$) in 300 ml of deionized water was added to the resulting solution. After 30 minutes of agitation, the resulting solution was transferred to an autoclave to be subjected to a hydrothermal reaction at 170° C. for 2 hours. The obtained reaction product was cooled, filtered, rinsed and dried at 105° C. for 22 hours.

Subsequently, ion exchange with silver ions was carried out in accordance with Example Y-I-1 to obtain silver-containing aluminum sulfate phosphate hydroxide particles Y-A-12.

When sodium carbonate, sodium nitrate, sodium silicate and sodium borate were used in place of sodium phosphate, silver-containing aluminum inorganic acid salt hydroxide particles having the same properties as the particles Y-A-12 and containing $CO_3^{2-}$, $NO_3^-$, $SiO_4^{2-}$ and $BO_3^{3-}$ inorganic acid ions were obtained, respectively.

Example Y-I-13

Manufacture of Particles Y-A-13 [$Ag_{0.3}$ $Na_{0.66}$]$_{0.96}Al_3(SO_4)_{1.92}(OH)_{6.12}$ The procedure of Example Y-1-1 was repeated except that the amount of the aqueous solution of silver sulfate was changed to 1,800 ml in the step of ion exchange between silver and sodium ions to obtain particles Y-A-13.

Example Y-I-14

Manufacture of Particles Y-A-14 [Ag$_{0.001}$Na$_{0.959}$]$_{0.96}$Al$_3$(SO$_4$)$_{1.92}$(OH)$_{6.12}$ The procedure of Example Y-I-1 was repeated except that silver sulfate was changed to silver nitrate and 300 ml of silver nitrate having a concentration of 0.001 mol/l was used in the step of ion exchange between silver and sodium ions to obtain particles Y-A-14.

Example Y-I-15

Manufacture of Particles Y-A-15 [Ag$_{0.00001}$Na$_{0.95999}$]$_{0.96}$Al$_3$(SO$_4$)$_{1.92}$(OH)$_{6.12}$ The procedure of Example Y-I-1 was repeated except that silver sulfate was changed to silver nitrate and 300 ml of silver nitrate having a concentration of 0.00001 mol/l was used in the step of ion exchange between silver and sodium ions to obtain particles Y-A-15.

Example Y-A-16

Manufacture of Particles Y-A-16 [Ag$_{0.1}$Na$_{0.86}$]$_{0.96}$Al$_3$(SO$_4$)$_{1.92}$(OH)$_{6.12}$ The particles Y-A-1 were baked at 400° C. for 1 hour in a nitrogen atmosphere to obtain particles Y-A-16. According to the powder X-ray diffraction method, no peak of [Ag$_{0.1}$Na$_{0.86}$]$_{0.96}$Al$_3$(SO$_4$)$_{1.92}$ (water-soluble compound) was observed and all the peaks were derived from [Ag$_{0.1}$Na$_{0.86}$]$_{0.96}$Al$_3$(SO$_4$)$_{1.92}$(OH)$_{6.12}$. The particles were spherical. After 10.00 g of the particles Y-A-16 was added to 100 ml of ion exchange water, stirred at 20° C. for 30 minutes, dehydrated, rinsed and dried at 120° C. for 16 hours, they had no weight loss and weighed 10.00 g.

Example Y-I-17

1 kg of the particles Y-A-1 was injected into a Henschel mixer. An aqueous solution obtained by diluting 20 g of γ-aminopropyltriethoxysilane with 50 g of water was sprayed over the particles to surface treat the particles at 120° C. and an agitation element revolution of 1,500 rpm for 30 minutes. The surface treated particles were dried at 200° C. for 1 hour to obtain particles Y-A-17.

Example Y-I-18

Manufacture of Particles Y-A-18 [Ag$_{0.1}$(NH$_4$)$_{0.86}$]$_{0.96}$Al$_3$(SO$_4$)$_{1.92}$(OH)$_{6.12}$ 508 ml of aluminum sulfate having a concentration of 1.025 mol/l and 68.72 g (0.52 mol) of ammonium sulfate were dissolved in deionized water to prepare 2,000 ml of a solution, and 616 ml of 3.382 N ammonia water was added to the solution under agitation over about 4 minutes at room temperature (alkali equivalent ratio: 0.999). After 20 minutes of agitation, the resulting solution was transferred to an autoclave to be subjected to a hydrothermal reaction at 100° C. for 1 hour, cooled to 25° C., filtered, rinsed with 500 ml of water and dried at 105° C. for 22 hours to obtain spherical ammonium type aluminum sulfate hydroxide particles. The subsequent steps were carried out in accordance with Example Y-I-1 to obtain particles Y-A-18. A SEM photomicrograph of the particles is shown in FIG. 19.

Manufacture of Disk-Like Particle Antibacterial Agent

Example Y-I-19

Manufacture of Particles Y-A-19 [Ag$_{0.1}$Na$_{0.91}$]$_{1.01}$[Al$_{2.66}$Zn$_{0.34}$]$_3$(SO$_4$)$_{1.95}$(OH)$_{5.77}$ 352 ml of aluminum sulfate having a concentration of 1.025 mol/l, 22.12 g of ZnO and 51.12 g (0.36 mol) of sodium sulfate were dissolved in deionized water to prepare 2,000 ml of a solution, and 284 ml of 3.382 N sodium hydroxide was added to the solution under agitation over about 4 minutes at room temperature. After 20 minutes of agitation, the resulting solution was transferred to an autoclave to be subjected to a hydrothermal reaction at 170° C. for 2 hours. The obtained reaction product was cooled to 25° C., filtered, rinsed with 500 ml of water and dried at 105° C. for 22 hours to obtain disk-like aluminum sulfate hydroxide particles. The subsequent steps were carried out in accordance with Example Y-I-1 except the ion exchange temperature with silver was changed to 80° C. and the treatment time was changed to 30 hours to obtain particles Y-A-19. A SEM photomicrograph of the particles Y-A-19 is shown in FIG. 18.

Example Y-I-20

Manufacture of Particles Y-A-20 [Ag$_{0.1}$K$_{0.9}$]$_1$[Al$_{2.7}$Zn$_{0.3}$]$_3$(SO$_4$)$_2$(OH)$_{5.70}$ 352 ml of aluminum sulfate having a concentration of 1.025 mol/l, 22.12 g of ZnO and 62.72 g (0.36 mol) of potassium sulfate were dissolved in deionized water to prepare 2,000 ml of a solution, and 268 ml of 3.4 N potassium hydroxide was added to the solution under agitation over about 4 minutes at room temperature (alkali equivalent ratio: 0.758, (sulfate having a monovalent cation)/(aluminum sulfate)=1.0). After 20 minutes of agitation, the resulting solution was transferred to an autoclave to be subjected to a hydrothermal reaction at 170° C. for 2 hours. The obtained hydrothermal reaction product was cooled to room temperature, filtered, rinsed band dried at 105° C. for 24 hours to obtain disk-like aluminum sulfate hydroxide. The subsequent steps were carried out in accordance with Example Y-I-19 to obtain particles Y-A-20.

Example Y-I-21

Manufacture of Particles Y-A-21 [Ag$_{0.1}$Na$_{0.8}$]$_{0.9}$[Al$_{2.61}$Zn$_{0.39}$]$_3$(SO$_4$)$_{1.60}$(OH)$_{6.34}$ 352 ml of aluminum sulfate having a concentration of 1.025 mol/l, 22.12 g of ZnO and 51.12 g (0.36 mol) of sodium sulfate were dissolved in deionized water to prepare 2,000 ml of a solution, and 332 ml of 3.382 N sodium hydroxide was added to the solution under agitation over about 4 minutes at room temperature (alkali equivalent ratio: 0.868, (sulfate having a monovalent cation)/(aluminum sulfate)=1.0). After 20 minutes of agitation, the resulting solution was transferred to an autoclave to be subjected to a hydrothermal reaction at 170° C. for 2 hours. The obtained hydrothermal reaction product was cooled to room temperature, filtered, rinsed and dried at 105° C. for 24 hours to obtain disk-like aluminum sulfate hydroxide. The subsequent steps were carried out in accordance with Example Y-I-19 to obtain particles Y-A-21.

Example Y-I-22

Manufacture of Particles Y-A-22 $[Ag_{0.3}Na_{0.71}]_{1.01}$ $[Al_{2.66}Zn_{0.34}]_3(SO_4)_{1.95}(OH)_{5.77}$ The procedure of Example Y-I-21 was repeated except that silver nitrate was used in place of silver sulfate, the concentration of silver nitrate was changed to 0.3 mol/l, and the amount of silver nitrate was changed to 300 ml in the step of ion exchange between silver and sodium ions to obtain particles Y-A-22.

Example Y-I-23

Manufacture of Particles Y-A-23 $[Ag_{0.001}Na_{1.009}]_{1.01}$ $[Al_{2.66}Zn_{0.34}]_3(SO_4)_{1.95}(OH)_{5.77}$ The procedure of Example Y-I-21 was repeated except that the concentration of silver nitrate was changed to 0.001 mol/l in the step of ion exchange between silver and sodium ions to obtain particles Y-A-23.

Example Y-I-24

Manufacture of Particles Y-A-24 $[Ag_{0.00001}Na_{1.00999}]_{1.01}[Al_{2.66}Zn_{0.34}]_3(SO_4)_{1.95}(OH)_{5.77}$ The procedure of Example Y-I-21 was repeated except that the concentration of silver nitrate was changed to 0.00001 mol/l in the step of ion exchange between silver and sodium ions to obtain particles Y-A-24.

Example Y-I-25

Manufacture of Particles Y-A-25 $[Ag_{0.1}Na_{0.91}]_{1.01}$ $[Al_{2.68}Zn_{0.32}]_3(SO_4)_{2.06}(OH)_{5.57}$ 350 ml of aluminum sulfate having a concentration of 1.03 mol/l was dissolved in deionized water to prepare 2,000 ml of a solution. 22.12 g of ZnO powders (first-grade reagent) was added to the solution under agitation at room temperature and stirred for 10 minutes. 284 ml of 3.385 N sodium hydroxide was then added to the solution over about 2 minutes. After 30 minutes of agitation, the resulting solution was transferred to an autoclave to be subjected to a hydrothermal reaction at 170° C. for 2 hours. The obtained hydrothermal reaction product was cooled to room temperature, filtered, rinsed and dried at 105° C. for 22 hours to obtain disk-like aluminum sulfate hydroxide. The subsequent steps were carried out in accordance with Example Y-I-19 to obtain particles Y-A-25.

Example Y-I-26

Manufacture of Particles Y-A-26 $[Ag_{0.1}Na_{0.92}]_{1.02}$ $[Al_{2.80}Zn_{0.20}]_3(SO_4)_{2.27}(OH)_{5.28}$ 350 ml of aluminum sulfate having a concentration of 1.03 mol/l and 51.12 g (0.36 mol) of sodium sulfate were dissolved in deionized water to prepare 2,000 ml of a solution, and 22.12 g of ZnO powders (first-grade reagent) was added under agitation at room temperature and stirred for 10 minutes. 188 ml of 3.385 N sodium hydroxide was added to the solution over about 1 minute. After 30 minutes of agitation, the resulting solution was transferred to an autoclave to be subjected to a hydrothermal reaction at 170° C. for 2 hours. The obtained hydrothermal reaction product was cooled to room temperature, filtered, rinsed and dried at 105° C. for 20 hours to obtain disk-like aluminum sulfate hydroxide. The subsequent steps were carried out in accordance with Example Y-I-19 to obtain particles Y-A-26.

Example Y-I-2-7

Manufacture of Particles Y-A-27 $[Ag_{0.1}Na_{0.95}]_{1.05}$ $[Al_{2.81}Zn_{0.19}]_3(SO_4)_{2.3}(OH)_{5.26}$ The procedure of Example Y-I-19 was repeated to obtain particles Y-A-27 except that the alkali equivalent ratio was changed to 0.90 in the manufacture of disk-like particles.

Example Y-I-28

Manufacture of Particles Y-A-28 $[Ag_{0.1}Na_{0.98}]_{1.08}$ $[Al_{2.69}Zn_{0.31}]_3(SO_4)_{2.09}(OH)_{5.59}$ The procedure of Example Y-I-19 was repeated to obtain particles Y-A-28 except that the (sulfate having a monovalent cation)/(aluminum sulfate) molar ratio was changed to 3.0 in the manufacture of disk-like particles.

Example Y-I-29

Manufacture of Particles Y-A-29 $[Ag_{0.1}Na_{0.9}]_1$ $[Al_{2.68}Zn_{0.32}]_3(SO_4)_{2.04}(OH)_{5.60}$ The procedure of Example Y-I-19 was repeated to obtain particles Y-A-29 except that the (sulfate having a monovalent cation)/(aluminum sulfate) molar ratio was changed to 0.20 in the manufacture of disk-like particles.

Manufacture of Rectangular Parallelepiped Particle Antibacterial Agents

Example Y-I-30

Manufacture of Particles Y-A-30 $[Ag_{0.1}(H_3O)_{0.86}]_{0.96}Al_3(SO_4)_{1.92}(OH)_{6.12}$ Particles Y-A-30 were obtained from the following raw materials by the following synthesizing method.

Raw Materials Used

| | | |
|---|---|---|
| Aluminum sulfate having a concentration of 1.04 mol/l | 2.0 mol | 1,923 ml |
| Aluminum hydroxide Al(OH)₃ (aluminum hydroxide; dried aluminum hydroxide gel S-100 of Kyowa Chemical Co., Ltd.; amorphous) | 2.0 mol | 156.02 g |

Synthesizing Method

The above aluminum hydroxide $Al(OH)_3$ was added to the above aqueous solution of aluminum sulfate under agitation to prepare a slurry of a hydrogen type aluminum sulfate hydroxide particle precipitate (reaction product). Ion exchange water was added to the slurry to dilute it so as to prepare 7.0 liters of a solution which was then stirred at room temperature for 5 hours and subjected to a hydrothermal treatment in an autoclave at 170° C. for 5 hours. The solution after the treatment was filtered, rinsed, dried and ground to obtain rectangular parallelepiped hydrogen type (hydronium type) aluminum sulfate hydroxide particles. The subsequent steps were carried out in accordance with Example X-I-1 to obtain rectangular parallelepiped particles Y-A-30. A SEM photomicrograph of the particles is shown in FIG. 20.

Example Y-I-31

Manufacture of Particles Y-A-31 [$Ag_{0.1}(H_3O)_{0.86}]_{0.96}Al_3(SO_4)_{1.92}(OH)_{6.12}$ The procedure of Example Y-I-30 was repeated except that the agitation time at room temperature before the reaction product was transferred to the autoclave was changed to 168 hours to obtain rectangular parallelepiped particles Y-A-31.

Comparative Examples

Comparative Example Y-I-1

Manufacture of Particles Y-V-1 [$Ag_{0.1}Na_{0.9}]_1Al_3(SO_4)_{2.36}(OH)_{5.28}$ 381 ml of aluminum sulfate having a concentration of 1.025 mol/l and 48.5 g (0.34 mol) of sodium sulfate were dissolved in deionized water to prepare 1,900 ml of a solution, and 357 ml of 3.382 N sodium hydroxide was added to the solution under agitation over about 3 minutes at room temperature (alkali equivalent ratio: 0.775, (molar ratio of (sulfate having a monovalent cation)/(aluminum sulfate)=0.28). After 20 minutes of agitation, the resulting solution was transferred to an autoclave to be subjected to a hydrothermal reaction at 100° C. for 2 hours. The obtained hydrothermal reaction product was cooled to 25° C., filtered, rinsed with 500 ml of water and dried at 105° C. for 22 hours to obtain aluminum sulfate hydroxide agglomerated particles.

The subsequent steps were carried out in accordance with Example Y-I-1 to obtain particles Y-V-1. The properties of the particles Y-V-1 are shown in Table-23. The particles were inferior in particle size uniformity and agglomerated as shown in FIG. 21 which shows a SEM photomicrograph thereof.

The reason that the particles obtained by this experiment were agglomerated and inferior in particle size uniformity is considered to be that the alkali equivalent ratio and the (sulfate having a monovalent cation)/(aluminum sulfate) molar ratio which are very important factors to be controlled for the manufacture of spherical particles in the present invention were not controlled to ranges specified by the present invention.

Comparative Example Y-I-2

Manufacture of Particles Y-V-2 [$Ag_{0.1}Na_{0.97}]_{1.07}Al_3(SO_4)_{2.42}(OH)_{5.23}$ The procedure of Comparative Example Y-I-1 was repeated except that the alkali equivalent ratio was raised to 0.8 to obtain particles Y-V-2.

In this experiment, although the alkali equivalent ratio was raised to the range of the present invention unlike Comparative Example Y-I-1, the (sulfate having a monovalent cation)/(aluminum sulfate) molar ratio was 0.28 which is the same as that of Comparative Example Y-I-1 and outside the range of the present invention. Therefore, the particle size uniformity of the obtained product was slightly improved as compared with that of the particles of Comparative Example Y-I-1 but still low, and the particles were agglomerated.

Comparative Example Y-I-3

Manufacture of Particles Y-V-3 [$Ag_{0.1}Na_{1.08}]_{1.18}Al_3(SO_4)_{2.11}(OH)_{5.96}$ The procedure of Comparative Example Y-I-1 was repeated except that the alkali equivalent ratio was raised to 1.0 which is higher than that of Comparative Example Y-I-2 to obtain particles Y-V-3. The particles Y-V-3 were inferior in particle size uniformity and agglomerated.

This experiment also shows that spherical aluminum sulfate hydroxide particles having excellent particle size uniformity of the present invention cannot be obtained if the (sulfate having a monovalent cation)/(aluminum sulfate) molar ratio does not fall within the range specified by the present invention even when the alkali equivalent ratio is within the range specified by the present invention like Comparative Example Y-1-2.

That is, it can be understood from Comparative Example Y-I-2 and Comparative Example Y-I-3 that even when the alkali equivalent ratio which should be controlled by the reaction of the present invention is in the preferred range of 0.8 or 1.0, if the (sulfate having a monovalent cation)/(aluminum sulfate) molar ratio is not controlled to the range specified by the present invention, the antibacterial agent particles having excellent particle uniformity of the present invention cannot be obtained.

Comparative Example Y-I-4

Manufacture of Particles Y-V-4 $Na_{0.96}Al_3(SO_4)_{1.92}(OH)_{6.12}$

The procedure of Example Y-I-1 was repeated except that ion exchange with silver was not carried out to obtain particles Y-V-4.

Comparative Example Y-I-5

Manufacture of a Mixture Showing an XRD Pattern of Particles Y-V-5 [$Ag_{0.1}Na_{0.9}]_1Al_3(SO_4)_2(OH)_6$ and Boehmite Gel The procedure of Example Y-I-3 was repeated except that the alkali equivalent ratio in the manufacture of spherical particles was changed to 1.3 which is outside the range specified by the present invention to obtain particles Y-V-5.

The particles were agglomerated and had a low particle size uniformity $D_{75}/D_{25}$ of 8.52. In the X-ray diffraction pattern of the particles, a peak derived from the boehmite gel which is a type of aluminum hydroxide crystal as a compound other than the compound of the formula (1) was observed.

Comparative Example Y-I-6

Manufacture of Particles Y-V-6 [$Ag_{0.1}Na_{1.07}]_{1.17}Al_3(SO_4)_{2.34}(OH)_{5.49}.0.51H_2O$ The procedure of Example Y-I-3 was repeated except that the (sulfate having a monovalent cation)/(aluminum sulfate) molar ratio was changed to 3.0 which is outside the range specified by the present invention to obtain particles Y-V-6.

The particles were agglomerated and had a large average secondary particle diameter of 16.72 μm.

Comparative Example Y-I-7

The procedure of Example Y-I-3 was repeated except that the hydrothermal treatment temperature was changed to 80° C. which is outside the range specified by the present invention to obtain particles Y-V-7.

The particles were agglomerated and had an average secondary particle diameter of 25.8 μm and a particle size uniformity $D_{75}/D_{25}$ of 4.02. It was found by XRD that they were amorphous.

The particles Y-A-1 to Y-A-31 of the above Examples Y-I were synthesized from high-purity raw materials (purified to such an extent that the contents of Pb, Cd, As and Ba were all 0.1 ppm or less, the content of Fe was 10 ppm or less, and the contents of Mn, Cu, Cr and Ni were 1 ppm or less) by using an apparatus made of the above corrosion resistant material.

Therefore, the contents of impurities were different from those of natural alum, that is, the contents of Pb, Cd, As and Ba were all 0.1 ppm or less, the content of Fe was 10 ppm or less, the contents of Mn, Cu, Cr and Ni were 1 ppm or less and the content of Cl was 100 ppm or less. The contents of impurities were measured by atomic absorption spectrophotometry, ICP-AES (Inductively Coupled Plasma-Atomic Emission Spectroscopy) or fluorescent X-ray spectroscopy.

TABLE 23

Antibacterial properties

| Ex. C. Ex. | Chemical formula | Particle shape | Particle name | Average secondary particle diameter μm | Sharpness of particle size distribution $Dr = D_{75}/D_{25}$ | BET specific surface area $m^2/g$ | Color | Powder X-ray diffraction pattern (peak other than that of compound of formula (1)) |
|---|---|---|---|---|---|---|---|---|
| Ex. Y-I-1 | $[Ag_{0.1}Na_{0.86}]_{0.96}Al_3(SO_4)_{1.92}(OH)_{6.12}$ | Spherical | Y-A-1-1 | 2.32 | 1.19 | 9.9 | White | None |
| Ex. Y-I-2 | $[Ag_{0.1}Na_{1.02}]_{1.12}Al_3(SO_4)_{2.17}(OH)_{5.78}$ | Spherical | Y-A-2 | 1.13 | 1.16 | 4.4 | White | None |
| Ex. Y-I-3 | $[Ag_{0.1}Na_{1.04}]_{1.14}Al_3(SO_4)_{2.30}(OH)_{5.54}$ | Spherical | Y-A-3 | 0.75 | 1.15 | 5.4 | White | None |
| Ex. Y-I-4 | $[Ag_{0.1}Na_{1.01}]_{1.11}Al_3(SO_4)_{2.33}(OH)_{5.45}$ | Spherical | Y-A-4 | 0.80 | 1.19 | 6.9 | White | None |
| Ex. Y-I-5 | $[Ag_{0.1}Na_{0.96}]_{1.06}Al_3(SO_4)_{2.35}(OH)_{5.36}$ | Spherical | Y-A-5 | 0.81 | 1.10 | 121.1 | White | None |
| Ex. Y-I-6 | $[Ag_{0.1}Na_{0.94}]_{1.04}Al_3(SO_4)_{2.34}(OH)_{5.36}2.6H_2O$ | Spherical | Y-A-6 | 0.69 | 1.29 | 97.1 | White | None |
| Ex. Y-I-7 | $[Ag_{0.1}Na_{0.97}]_{1.07}Al_3(SO_4)_{2.32}(OH)_{5.43}$ | Spherical | Y-A-7 | 4.55 | 1.18 | 50.2 | White | None |
| Ex. Y-I-8 | $[Ag_{0.1}Na_{0.99}]_{1.09}Al_3(SO_4)_{2.30}(OH)_{5.49}$ | Spherical | Y-A-8 | 0.88 | 1.15 | 45.7 | White | None |
| Ex. Y-I-9 | $[Ag_{0.1}K_{1.1}]_{1.2}Al_3(SO_4)_{2.2}(OH)_{5.8}$ | Spherical | Y-A-9 | 0.80 | 1.10 | 11.3 | White | None |
| Ex. Y-I-10 | $[Ag_{0.1}K_{0.45}Na_{0.45}]_1Al_3(SO_4)_{1.99}(OH)_{6.02}$ | Spherical | Y-A-10 | 1.15 | 1.19 | 10.6 | White | None |
| Ex. Y-I-11 | $[Ag_{0.1}Na_{0.9}]_1Ti_{0.01}Al_{2.94}(SO_4)_2(OH)_{5.86}$ | Spherical | Y-A-11 | 0.64 | 1.15 | 12.5 | White | None |
| Ex. Y-I-12 | $[Ag_{0.1}Na_{0.9}]_1Al_3(SO_4)_{2.2}(PO_4)_{0.1}(OH)_{5.4}$ | Spherical | Y-A-12 | 1.17 | 1.16 | 4.6 | White | None |
| Ex. Y-I-13 | $[Ag_{0.3}Na_{0.66}]_{0.96}Al_3(SO_4)_{1.92}(OH)_{6.12}$ | Spherical | Y-A-13 | 1.64 | 1.15 | 9.9 | White | None |
| Ex. Y-I-14 | $[Ag_{0.001}Na_{0.959}]_{0.96}Al_3(SO_4)_{1.92}(OH)_{6.12}$ | Spherical | Y-A-14 | 1.64 | 1.15 | 9.9 | White | None |
| Ex. Y-I-15 | $[Ag_{0.00001}Na_{0.95999}]_{0.96}Al_3(SO_4)_{1.92}(OH)_{6.12}$ | Spherical | Y-A-15 | 1.64 | 1.15 | 9.9 | White | None |
| Ex. Y-I-16 | 400° C. × 1 hour baked product of Example 1 | Spherical | Y-A-16 | 2.08 | 1.18 | 9.5 | White | None |
| Ex. Y-I-17 | surface treated product of Example 1 | Spherical | Y-A-17 | 1.68 | 1.15 | 9.5 | White | None |
| Ex. Y-I-18 | $[Ag_{0.1}(NH_4)_{0.86}]_{0.96}Al_3(SO_4)_{1.92}(OH)_{6.12}$ | Spherical | Y-A-18 | 0.31 | 1.1 | 38 | White | None |
| Ex. Y-I-19 | $[Ag_{0.1}Na_{0.91}]_{1.01}[Al_{2.66}Zn_{0.34}]_3(SO_4)_{1.95}(OH)_{5.77}$ | Disk-like | Y-A-19 | 1.35 | 1.15 | 7.7 | White | None |
| Ex. Y-I-20 | $[Ag_{0.1}K_{0.9}]_1[Al_{2.7}Zn_{0.3}]_3(SO_4)_2(OH)_{5.70}$ | Disk-like | Y-A-20 | 1.21 | 1.13 | 3.1 | White | None |
| Ex. Y-I-21 | $[Ag_{0.1}Na_{0.8}]_{0.9}[Al_{2.61}Zn_{0.39}]_3(SO_4)_{1.60}(OH)_{6.34}$ | Disk-like | Y-A-21 | 2.86 | 1.76 | 42 | White | None |
| Ex. Y-I-22 | $[Ag_{0.3}Na_{0.71}]_{1.01}[Al_{2.66}Zn_{0.34}]_3(SO_4)_{1.95}(OH)_{5.77}$ | Disk-like | Y-A-22 | 1.35 | 1.15 | 7.7 | White | None |
| Ex. Y-I-23 | $[Ag_{0.001}Na_{1.009}]_{1.01}[Al_{2.66}Zn_{0.34}]_3(SO_4)_{1.95}(OH)_{5.77}$ | Disk-like | Y-A-23 | 1.35 | 1.15 | 7.7 | White | None |
| Ex. Y-I-24 | $[Ag_{0.00001}Na_{1.00999}]_{1.01}[Al_{2.66}Zn_{0.34}]_3(SO_4)_{1.95}(OH)_{5.77}$ | Disk-like | Y-A-24 | 1.35 | 1.15 | 7.7 | White | None |
| Ex. Y-I-25 | $[Ag_{0.1}Na_{0.91}]_{1.01}[Al_{2.68}Zn_{0.32}]_3(SO_4)_{2.06}(OH)_{5.57}$ | Disk-like | Y-A-25 | 1.65 | 1.13 | 8.8 | White | None |
| Ex. Y-I-26 | $[Ag_{0.1}Na_{0.92}]_{1.02}[Al_{2.80}Zn_{0.20}]_3(SO_4)_{2.27}(OH)_{5.28}$ | Disk-like | Y-A-26 | 1.18 | 1.15 | 4.9 | White | None |
| Ex. Y-I-27 | $[Ag_{0.1}Na_{0.95}]_{1.05}[Al_{2.81}Zn_{0.19}]_3(SO_4)_{2.3}(OH)_{5.26}$ | Disk-like | Y-A-27 | 3.77 | 1.22 | 21 | White | None |
| Ex. Y-I-28 | $[Ag_{0.1}Na_{0.98}]_{1.08}[Al_{2.69}Zn_{0.31}]_3(SO_4)_{2.09}(OH)_{5.59}$ | Disk-like | Y-A-28 | 0.61 | 1.08 | 11.1 | White | None |
| Ex. Y-I-29 | $[Ag_{0.1}Na_{0.9}]_1[Al_{2.68}Zn_{0.32}]_3(SO_4)_{2.04}(OH)_{5.60}$ | Disk-like | Y-A-29 | 0.64 | 1.09 | 10 | White | None |
| Ex. Y-I-30 | $[Ag_{0.1}(H_3O)_{0.86}]_{0.96}Al_3(SO_4)_{1.92}(OH)_{6.12}$ | Parallelepiped | Y-A-30 | 1.8 | 1.7 | 2 | White | None |
| Ex. Y-I-31 | $[Ag_{0.1}(H_3O)_{0.86}]_{0.96}Al_3(SO_4)_{1.92}(OH)_{6.12}$ | Parallelepiped | Y-A-31 | 1.0 | 1.19 | 3 | White | None |
| C. Ex. Y-I-1 | $[Ag_{0.1}Na_{0.93}]_{1.0}Al_3(SO_4)_{2.36}(OH)_{5.28}$ | Agglomerated | Y-V-1 | 7.46 | 11.61 | 7.8 | White | None |
| C. Ex. Y-I-2 | $[Ag_{0.1}Na_{0.97}]_{1.07}Al_3(SO_4)_{2.42}(OH)_{5.23}$ | Agglomerated | Y-V-2 | 1.94 | 3.17 | 60.4 | White | None |
| C. Ex. Y-I-3 | $[Ag_{0.1}Na_{1.08}]_{1.18}Al_3(SO_4)_{2.11}(OH)_{5.96}$ | Agglomerated | Y-V-3 | 46.5 | 5.45 | 0.8 | White | None |
| C. Ex. Y-I-4 | $Na_{0.96}Al_3(SO_4)_{1.92}(OH)_{6.12}$ Without silver | Spherical | Y-V-4 | 2.32 | 1.19 | 9.9 | White | None |
| C. Ex. Y-I-5 | Showing XRD pattern of a mixture of $[Ag_{0.1}Na_{0.9}]_1Al_3(SO_4)_2(OH)_6$ and boehmite gel | Agglomerated | Y-V-5 | 18.93 | 8.52 | 39 | White | None |

TABLE 23-continued

| | | | | | | | |
|---|---|---|---|---|---|---|---|
| C. Ex. Y-I-6 | [Ag$_{0.1}$Na$_{1.07}$]$_{1.17}$Al$_3$(SO$_4$)$_{2.34}$(OH)$_{5.49}$ | Agglomerated | Y-V-6 | 16.72 | 1.38 | 10.3 | White | None |
| C. Ex. Y-I-7 | XRD pattern shows amorphous state | Agglomerated | Y-V-7 | 25.78 | 4.02 | 82 | White | None | production conditions and products

Antibacterial properties

| | Production conditions | | | | | | products | | |
|---|---|---|---|---|---|---|---|---|---|
| Ex. C. Ex. | Aluminum sulfate, zinc oxide, titanium sulfate | alkali or Al(OH)$_3$ | alkali equivalent ratio | sulfate having a monovalent cation | (sulfate having a monovalent cation)/ (Al$_2$(SO$_4$)$_3$ molar ratio | hydrothermal treatment Temperature ° C. | time | particle name | shape | D$_{75}$/D$_{25}$ |
| Ex. Y-I-1 | Al$_2$(SO$_4$)$_3$ | NaOH | 0.999 | Na$_2$SO$_4$ | 1.0 | 170 | 2 | Y-A-1-1 | Spherical | 1.19 |
| Ex. Y-I-2 | Al$_2$(SO$_4$)$_3$ | NaOH | 0.95 | Na$_2$SO$_4$ | 1.0 | 170 | 2 | Y-A-2 | Spherical | 1.16 |
| Ex. Y-I-3 | Al$_2$(SO$_4$)$_3$ | NaOH | 0.90 | Na$_2$SO$_4$ | 1.0 | 170 | 2 | Y-A-3 | Spherical | 1.05 |
| Ex. Y-I-4 | Al$_2$(SO$_4$)$_3$ | NaOH | 0.835 | Na$_2$SO$_4$ | 1.0 | 170 | 2 | Y-A-4 | Spherical | 1.19 |
| Ex. Y-I-5 | Al$_2$(SO$_4$)$_3$ | NaOH | 0.90 | Na$_2$SO$_4$ | 1.0 | 100 | 29 | Y-A-5 | Spherical | 1.10 |
| Ex. Y-I-6 | Al$_2$(SO$_4$)$_3$ | NaOH | 0.835 | Na$_2$SO$_4$ | 1.0 | 100 | 29 | Y-A-6 | Spherical | 1.29 |
| Ex. Y-I-7 | Al$_2$(SO$_4$)$_3$ | NaOH | 0.90 | Na$_2$SO$_4$ | 0.33 | 200 | 1.5 | Y-A-7 | Spherical | 1.18 |
| Ex. Y-I-8 | Al$_2$(SO$_4$)$_3$ | NaOH | 0.90 | Na$_2$SO$_4$ | 2.0 | 250 | 1 | Y-A-8 | Spherical | 1.15 |
| Ex. Y-I-9 | Al$_2$(SO$_4$)$_3$ | KOH | 0.90 | K$_2$SO$_4$ | 1.0 | 170 | 2 | Y-A-9 | Spherical | 1.10 |
| Ex. Y-I-10 | Al$_2$(SO$_4$)$_3$ | NaOH, KOH | 0.90 | K$_2$SO$_4$, Na$_2$SO$_4$ | 1.0 | 170 | 2 | Y-A-10 | Spherical | 1.19 |
| Ex. Y-I-11 | Al$_2$(SO$_4$)$_3$ Ti$_2$(SO$_4$)$_3$ | NaOH | 0.999 | Na$_2$SO$_4$ | 1.0 | 170 | 2 | Y-A-12 | Spherical | 1.15 |
| Ex. Y-I-12 | Al$_2$(SO$_4$)$_3$ | NaOH | 0.999 | Na$_2$SO$_4$, Na$_3$PO$_4$ | 0.67 | 170 | 2 | Y-A-13 | Spherical | 1.16 |
| Ex. Y-I-13 | Al$_2$(SO$_4$)$_3$ | NaOH | 0.999 | Na$_2$SO$_4$ | 1.0 | 170 | 2 | Y-A-14 | Spherical | 1.15 |
| Ex. Y-I-14 | Al$_2$(SO$_4$)$_3$ | NaOH | 0.999 | Na$_2$SO$_4$ | 1.0 | 170 | 2 | Y-A-15 | Spherical | 1.15 |
| Ex. Y-I-15 | Al$_2$(SO$_4$)$_3$ | NaOH | 0.999 | Na$_2$SO$_4$ | 1.0 | 170 | 2 | Y-A-16 | Spherical | 1.15 |
| Ex. Y-I-16 | Al$_2$(SO$_4$)$_3$ | NaOH | 0.999 | Na$_2$SO$_4$ | 1.0 | 170 | 22 | Y-A-17 | Spherical | 1.18 |
| Ex. Y-I-17 | Al$_2$(SO$_4$)$_3$ | NaOH | 0.999 | Na$_2$SO$_4$ | 1.0 | 170 | 1 | Y-A-18 | Spherical | 1.15 |
| Ex. Y-I-18 | Al$_2$(SO$_4$)$_3$ | Na$_4$OH | 0.999 | (NH$_4$)$_2$SO$_4$ | 1.0 | 100 | 5 | Y-A-19 | Spherical | 1.10 |
| Ex. Y-I-19 | Al$_2$(SO$_4$)$_3$, ZnO | NaOH | 0.783 | Na$_2$SO$_4$ | 1.0 | 170 | 2 | Y-A-19 | Disk-like | 1.15 |
| Ex. Y-I-20 | Al$_2$(SO$_4$)$_3$, ZnO | KOH | 0.758 | K$_2$SO$_4$ | 1.0 | 170 | 2 | Y-A-20 | Disk-like | 1.13 |
| Ex. Y-I-21 | Al$_2$(SO$_4$)$_3$, ZnO | NaOH | 0.868 | Na$_2$SO$_4$ | 1.0 | 170 | 2 | Y-A-21 | Disk-like | 1.76 |
| Ex. Y-I-22 | Al$_2$(SO$_4$)$_3$, ZnO | NaOH | 0.783 | Na$_2$SO$_4$ | 1.0 | 170 | 2 | Y-A-22 | Disk-like | 1.15 |
| Ex. Y-I-23 | Al$_2$(SO$_4$)$_3$, ZnO | NaOH | 0.783 | Na$_2$SO$_4$ | 1.0 | 170 | 2 | Y-A-23 | Disk-like | 1.15 |
| Ex. Y-I-24 | Al$_2$(SO$_4$)$_3$, ZnO | NaOH | 0.783 | Na$_2$SO$_4$ | 1.0 | 170 | 2 | Y-A-24 | Disk-like | 1.15 |
| Ex. Y-I-25 | Al$_2$(SO$_4$)$_3$, ZnO | NaOH | 0.783 | no antibacterial agent was molded | 0 | 170 | 2 | Y-A-25 | Disk-like | 1.13 |
| Ex. Y-I-26 | Al$_2$(SO$_4$)$_3$, ZnO | NaOH | 0.613 | Na$_2$SO$_4$ | 1.0 | 170 | 2 | Y-A-26 | Disk-like | 1.15 |
| Ex. Y-I-27 | Al$_2$(SO$_4$)$_3$, ZnO | NaOH | 0.90 | Na$_2$SO$_4$ | 1.0 | 170 | 2 | Y-A-27 | Disk-like | 1.22 |
| Ex. Y-I-28 | Al$_2$(SO$_4$)$_3$, ZnO | NaOH | 0.868 | Na$_2$SO$_4$ | 3.0 | 170 | 2 | Y-A-28 | Disk-like | 1.08 |
| Ex. Y-I-29 | Al$_2$(SO$_4$)$_3$, ZnO | NaOH | 0.868 | Na$_2$SO$_4$ | 0.20 | 170 | 2 | Y-A-29 | Disk-like | 1.09 |
| Ex. Y-I-30 | Al$_2$(SO$_4$)$_3$ | Al(OH)$_3$ | — | — | — | 170 | 2 | Y-A-30 | Parallelepiped | 1.7 |
| Ex. Y-I-31 | Al$_2$(SO$_4$)$_3$ | Al(OH)$_3$ | — | — | — | 170 | 2 | Y-A-31 | Parallelepiped | 1.19 |
| C. Ex. Y-I-1 | Al$_2$(SO$_4$)$_3$ | NaOH | 0.775 | Na$_2$SO$_4$ | 0.28 | 100 | 2 | Y-V-1 | Agglomerated | 11.6 |
| C. Ex. Y-I-2 | Al$_2$(SO$_4$)$_3$ | NaOH | 0.80 | Na$_2$SO$_4$ | 0.28 | 100 | 2 | Y-V-2 | Agglomerated | 3.17 |
| C. Ex. Y-I-3 | Al$_2$(SO$_4$)$_3$ | NaOH | 1.0 | Na$_2$SO$_4$ | 0.28 | 100 | 2 | Y-V-3 | Agglomerated | 5.45 |
| C. Ex. Y-I-4 | Al$_2$(SO$_4$)$_3$ | NaOH | 0.999 | Na$_2$SO$_4$ | 1.0 | 170 | 2 | Y-V-4 | Spherical | 1.19 |
| C. Ex. Y-I-5 | Al$_2$(SO$_4$)$_3$ | NaOH | 1.3 | Na$_2$SO$_4$ | 1.0 | 170 | 2 | Y-V-5 | Agglomerated | 8.52 |
| C. Ex. Y-I-6 | Al$_2$(SO$_4$)$_3$ | NaOH | 0.9 | Na$_2$SO$_4$ | 3.0 | 170 | 2 | Y-V-6 | Agglomerated | 1.38 |
| C. Ex. Y-I-7 | Al$_2$(SO$_4$)$_3$ | NaOH | 0.9 | Na$_2$SO$_4$ | 1.0 | 80 | 2 | Y-V-7 | Agglomerated | 4.02 |

Ex. Example
C. Ex. Comparative Example

A detailed description is subsequently given of the manufacture of antibacterial resin products comprising an antibacterial agent represented by the formula (Y-I).

2,5-thiophenediyl(5-tert-butyl-1,3-benzohexazole) was added in an amount shown in tables as a fluorescent brightener (there is a case where it was not added).

Manufacture of Polypropylene Molded Articles

Examples Y-II-1 to Y-II-31 and Comparative Examples Y-II-1 to Y-II-81

In Example Y-II-1, 100 parts by weight of polypropylene for transparent injection molding and 0.06 part by weight of the particles Y-A-1 shown in Table-23 were pre-mixed together, and the resulting mixture was kneaded by a double-screw kneading extruder at 230° C. to obtain a mixture pellet which was then injection molded at 230° C. to prepare a 2 mm-thick test piece and measure its antibacterial properties, transparency and whiteness by the above methods (6) to (8) for measuring resin products. The results are shown on the left side of the vertical double lines in Table-24.

A test of filter passability at the time of kneading and extrusion (pressure of extruder) was carried out by the method (9).

The results are shown on the right side of the vertical double lines in Table-24.

In the tests of Examples Y-II-2 to Y-II-31 and Comparative Examples Y-II-1 to Y-II-9, a test piece was prepared in the same manner as in Example Y-II-1 except that the type and amount of the antibacterial agent particles were changed as shown in Table-24 in some of them to carry out the test. The results are shown in Table-24.

Comparative Examples Y-II-1 to Y-II-3 and Comparative Examples Y-II-5 differ from Example Y-II-1 in that the particles Y-V-1 to Y-V-3 and Y-V-5 were agglomerated and had a large Dr width (particle size distribution width), Comparative Example Y-II-6 differs from Example Y-II-1 in that the particles Y-V-6 had a small Dr width (particle size distribution width) and a large average secondary particle diameter of 16.72 μm and were agglomerated, Comparative Example Y-II-4 differs from Example Y-II-1 in that the particles Y-V-4 were aluminum sulfate hydroxide particles containing no silver, and Comparative Example Y-II-8 differs from Example Y-II-1 in that no antibacterial agent was added in the test. Test pieces were prepared in the same manner as in Example Y-II-1 except for what are described above, and the same measurements were made on the test pieces. The results are shown in Table-24.

It was confirmed that Examples were excellent in filter passability at the time of kneading and extrusion, antibacterial properties, transparency and color whereas Comparative Examples had a problem with at least one of these properties.

In Comparative Examples Y-II-1 to Y-II-3 and Comparative Example Y-II-5, since the particles Y-V-1 to Y-V-3 and Y-V-5 which were agglomerated and had a large Dr width (particle size distribution width) were used, the obtained molded articles were inferior in antibacterial properties and transparency and had a problem with filter passability at the time of kneading and extrusion.

In Comparative Example Y-II-6, since the particles Y-V-6 which had a small Dr width (particle size distribution width) but a large average secondary particle diameter of 16.72 μm and were agglomerated were used, the obtained molded article was inferior in antibacterial properties and transparency and had a problem with filter passability at the time of kneading and extrusion.

In Comparative Example Y-II-4, although aluminum sulfate hydroxide particles were used, as they were not aluminum sulfate hydroxide particles containing silver, no antibacterial effect was observed at all.

In Comparative Example Y-II-8, since an antibacterial agent was not used, no antibacterial effect was observed at all though the obtained molded article had no problem with transparency and color.

TABLE 24

| | | Antibacterial properties | | | |
|---|---|---|---|---|---|
| Ex. C. Ex. | Name of antibacterial agent particle | Amount of antibacterial agent (pbw) | Amount of fluorescent brightener (pbw) | Antibacterial properties | |
| | | | | Escherichia coli cfu/ml | Staphylococcus aureus cfu/ml |
| Ex. Y-II-1 | Y-A-1-1 | 0.06 | 0.0001 | $1 \times 10$ | $1 \times 10$ |
| Ex. Y-II-2 | Y-A-2 | 0.06 | — | 10> | 10> |
| Ex. Y-II-3 | Y-A-3 | 0.06 | 0.0001 | 10> | 10> |
| Ex. Y-II-4 | Y-A-4 | 0.06 | 0.0001 | $1 \times 10$ | $1 \times 10$ |
| Ex. Y-II-5 | Y-A-5 | 0.06 | 0.0001 | 10> | 10> |
| Ex. Y-II-6 | Y-A-6 | 0.06 | 0.0001 | 10> | 10> |
| Ex. Y-II-7 | Y-A-7 | 0.06 | 0.0001 | $5 \times 10$ | $5 \times 10$ |
| Ex. Y-II-8 | Y-A-8 | 0.06 | 0.0001 | 10> | 10> |
| Ex. Y-II-9 | Y-A-9 | 0.06 | 0.01 | 10> | 10> |
| Ex. Y-II-10 | Y-A-10 | 0.06 | 0.001 | 10> | 10> |
| Ex. Y-II-11 | Y-A-11 | 0.06 | 0.0001 | 10> | 10> |
| Ex. Y-II-12 | Y-A-12 | 0.06 | 0.0001 | 10> | 10> |
| Ex. Y-II-13 | Y-A-13 | 0.001 | 0.0001 | $8 \times 10$ | $8 \times 10$ |
| Ex. Y-II-14 | Y-A-14 | 2 | 0.0001 | $5 \times 10$ | $5 \times 10$ |
| Ex. Y-II-15 | Y-A-15 | 300 | 0.0001 | $5 \times 10$ | $5 \times 10$ |
| Ex. Y-II-16 | Y-A-16 | 0.06 | 0.0001 | 10> | 10> |

TABLE 24-continued

| | | | | | |
|---|---|---|---|---|---|
| Ex. Y-II-17 | Y-A-17 | 0.06 | 0.0001 | 10> | 10> |
| Ex. Y-II-18 | Y-A-18 | 0.06 | 0.0001 | 10> | 10> |

| | | Antibacterial properties | | | |
|---|---|---|---|---|---|
| Ex. C. Ex. | Name of antibacterial agent particle | Transparency % | Color | Pressure of extruder kg/cm$^2$ | |
| | | | | 2 hours | 24 hours |
| Ex. Y-II-1 | Y-A-1-1 | 100 | Achromatic (white) | 26 | 40 |
|  | Y-A-2 | 100 | Achromatic (white) | 22 | 27 |
| Ex. Y-II-2 | Y-A-3 | 100 | Achromatic (white) | 21 | 23 |
| Ex. Y-II-3 | Y-A-4 | 100 | Achromatic (white) | 26 | 35 |
| Ex. Y-II-4 | Y-A-5 | 100 | Achromatic (white) | 21 | 25 |
| Ex. Y-II-5 | Y-A-6 | 100 | Achromatic (white) | 28 | 50 |
| Ex. Y-II-6 | Y-A-7 | 100 | Achromatic (white) | 26 | 40 |
| Ex. Y-II-7 | Y-A-8 | 100 | Achromatic (white) | 22 | 30 |
| Ex. Y-II-8 | Y-A-9 | 100 | Achromatic (white) | 21 | 25 |
| Ex. Y-II-9 | Y-A-10 | 100 | Achromatic (white) | 26 | 35 |
| Ex. Y-II-11 | Y-A-11 | 99 | Achromatic (white) | 22 | 30 |
| Ex. Y-II-12 | Y-A-12 | 100 | Achromatic (white) | 22 | 30 |
| Ex. Y-II-13 | Y-A-13 | 100 | Achromatic (white) | 22 | 30 |
| Ex. Y-II-14 | Y-A-14 | 98 | Achromatic (white) | 22 | 30 |
| Ex. Y-II-15 | Y-A-15 | 10 | Achromatic (white) | 22 | 30 |
| Ex. Y-II-16 | Y-A-16 | 100 | Achromatic (white) | 23 | 40 |
| Ex. Y-II-17 | Y-A-17 | 100 | Achromatic (white) | 22 | 30 |
| Ex. Y-II-18 | Y-A-18 | 100 | Achromatic (white) | 22 | 30 |

| | | | | Antibacterial properties | |
|---|---|---|---|---|---|
| Ex. C. Ex. | Name of antibacterial agent particle | Amount of antibacterial agent (pbw) | Amount of fluorescent brightener (pbw) | Antibacterial properties | |
| | | | | *Escherichia col* cfu/ml | *Staphylococcus aureu* cfu/ml |
| Ex. Y-II-19 | Y-A-19 | 0.06 | 0.0001 | 10> | 10> |
| Ex. Y-II-20 | Y-A-20 | 0.06 | 0.01 | 10> | 10> |
| Ex. Y-II-21 | Y-A-21 | 0.06 | 0.0001 | 5 × 10 | 5 × 10 |
| Ex. Y-II-22 | Y-A-22 | 0.001 | 0.0001 | 10> | 10> |
| Ex. Y-II-23 | Y-A-23 | 2 | 0.0001 | 5 × 10 | 5 × 10 |
| Ex. Y-II-24 | Y-A-24 | 300 | 0.0001 | 5 × 10 | 5 × 10 |
| Ex. Y-II-25 | Y-A-25 | 0.06 | 0.0001 | 1 × 10 | 1 × 10 |
| Ex. Y-II-26 | Y-A-26 | 0.06 | 0.0001 | 10> | 10> |
| Ex. Y-II-27 | Y-A-27 | 0.06 | 0.0001 | 5 × 10 | 5 × 10 |
| Ex. Y-II-28 | Y-A-28 | 0.06 | 0.0001 | 10> | 10> |
| Ex. Y-II-29 | Y-A-29 | 0.06 | 0.0001 | 10> | 10> |
| Ex. Y-II-30 | Y-A-30 | 0.06 | 0.0001 | 5 × 10 | 5 × 10 |
| Ex. Y-II-31 | Y-A-31 | 0.06 | 0.0001 | 10> | 10> |
| C. Ex. Y-II-1 | Y-V-1 | 0.06 | 0.0001 | 5 × 10$^3$ | 5 × 10$^3$ |
| C. Ex. Y-II-2 | Y-V-2 | 0.06 | 0.0001 | 5 × 10$^2$ | 5 × 10$^2$ |
| C. Ex. Y-II-3 | Y-V-3 | 0.06 | 0.0001 | 5 × 10$^3$ | 5 × 10$^3$ |
|  |  | 300 | 0.0001 | 10> | 10> |
| C. Ex. Y-II-4 | Y-V-4 | 0.06 | 0.0001 | 1 × 10$^6$ | 1 × 10$^6$ |
| C. Ex. Y-II-5 | Y-V-5 | 0.06 | 0.0001 | 5 × 10$^3$ | 5 × 10$^3$ |
| C. Ex. Y-II-6 | Y-V-6 | 0.06 | 0.0001 | 5 × 10$^2$ | 5 × 10$^2$ |
| C. Ex. Y-II-7 | Y-V-7 | 0.06 | 0.0001 | 5 × 10$^3$ | 5 × 10$^3$ |
| C. Ex. Y-II-8 | nil | — | 0.0001 | 1 × 10$^6$ | 1 × 10$^6$ |

| | | Antibacterial properties | | | |
|---|---|---|---|---|---|
| Ex. C. Ex. | Name of antibacterial agent particle | Transparency % | Color | Pressure of extruder Kg/cm$^2$ | |
| | | | | 2 hours | 24 hours |
| Ex. Y-II-19 | Y-A-19 | 99 | Achromatic (white) | 22 | 30 |
| Ex. Y-II-20 | Y-A-20 | 100 | Achromatic (white) | 22 | 30 |
| Ex. Y-II-21 | Y-A-21 | 100 | Achromatic (white) | 35 | 100 |
| Ex. Y-II-22 | Y-A-22 | 100 | Achromatic (white) | 22 | 30 |
| Ex. Y-II-23 | Y-A-23 | 98 | Achromatic (white) | 22 | 30 |
| Ex. Y-II-24 | Y-A-24 | 10 | Achromatic (white) | 22 | 30 |

TABLE 24-continued

| Ex. Y-II-25 | Y-A-25 | 100 | Achromatic (white) | 25 | 40 |
|---|---|---|---|---|---|
| Ex. Y-II-26 | Y-A-26 | 100 | Achromatic (white) | 22 | 30 |
| Ex. Y-II-27 | Y-A-27 | 100 | Achromatic (white) | 25 | 30 |
| Ex. Y-II-28 | Y-A-28 | 100 | Achromatic (white) | 22 | 30 |
| Ex. Y-II-29 | Y-A-29 | 100 | Achromatic (white) | 22 | 30 |
| Ex. Y-II-30 | Y-A-30 | 100 | Achromatic (white) | 35 | 100 |
| Ex. Y-II-31 | Y-A-31 | 99 | Achromatic (white) | 23 | 30 |
| C. Ex. Y-II-1 | Y-V-1 | 95 | Achromatic (white) | 200< | 200< |
| C. Ex. Y-II-2 | Y-V-2 | 97 | Achromatic (white) | 200< | 200< |
| C. Ex. Y-II-3 | Y-V-3 | 92 | Achromatic (white) | 200< | 200< |
|  |  | 1 | Achromatic (white) |  |  |
| C. Ex. Y-II-4 | Y-V-4 | 100 | Achromatic (white) | 22 | 30 |
| C. Ex. Y-II-5 | Y-V-5 | 95 | Achromatic (white) | 200< | 200< |
| C. Ex. Y-II-6 | Y-V-6 | 97 | Achromatic (white) | 200< | 200< |
| C. Ex. Y-II-7 | Y-V-7 | 95 | Achromatic (white) | 200< | 200< |
| C. Ex. Y-II-8 | nil | 100 | Achromatic (white) | 20 | 22 |

Ex.: Example
C. Ex.: Comparative Example
pbw.: part by weight

Manufacture of Polystyrene, EVA and Acryl Transparent Resin Molded Articles

Examples Y-II-32 to Y-II-34

The procedure of Example Y-II-1 was repeated except that the resin to be made antibacterial was changed from polypropylene to polystyrene, EVA resin and acrylic resin, the antibacterial agent was changed to the particles Y-A-3, Y-A-19 and Y-A-31, the amount of the antibacterial agent was changed as shown in Table-25, and the kneading and molding temperatures were changed to 210° C. in Examples Y-II-32 to Y-II-34. The results are shown in Table-25.

The molded articles of Examples were achromatic (white) and had excellent antibacterial properties with unimpaired transparency.

TABLE 25

| | | | | Antibacterial properties | | | |
|---|---|---|---|---|---|---|---|
| Ex. C. Ex. | Resin to be made antibacterial | Name of antibacterial agent particle | Amount of antibacterial agent | Amount of fluorescent brightener (pbw) | | Antibacterial properties | |
| | | | | | | *Escherichia coli* cfu/ml | *Staphylococcus aureus* cfu/ml |
| Ex. Y-II-32 | Polystyrene | Y-A-3 | 0.1 | 0.00001 | | 10> | 10> |
| | | Y-A-19 | 0.1 | 0.00001 | | 10> | 10> |
| | | Y-A-31 | 0.1 | 0.00001 | | 10> | 10> |
| Ex. Y-II-33 | EVA resin | Y-A-3 | 0.1 | 0.00001 | | 10> | 10> |
| | | Y-A-19 | 0.1 | 0.00001 | | 10> | 10> |
| | | Y-A-31 | 0.1 | 0.00001 | | 10> | 10> |
| Ex. Y-II-34 | Acrylic resin | Y-A-3 | 0.1 | 0.00001 | | 10> | 10> |
| | | Y-A-19 | 0.1 | 0.00001 | | 10> | 10> |
| | | Y-A-31 | 0.1 | 0.00001 | | 10> | 10> |

| | | | Antibacterial properties | | | |
|---|---|---|---|---|---|---|
| Ex. C. Ex. | Resin to be made antibacterial | Name of antibacterial agent particle | Transparency % | Color | Pressure of extruder Kg/cm² | |
| | | | | | 2 hours | 24 hours |
| Ex. Y-II-32 | Polystyrene | Y-A-3 | 100 | Achromatic (white) | 30 | 35 |
| | | Y-A-19 | 100 | Achromatic (white) | 30 | 34 |
| | | Y-A-31 | 100 | Achromatic (white) | 30 | 36 |
| Ex. Y-II-33 | EVA resin | Y-A-3 | 100 | Achromatic (white) | 40 | 45 |
| | | Y-A-19 | 100 | Achromatic (white) | 40 | 44 |
| | | Y-A-31 | 100 | Achromatic (white) | 40 | 47 |
| Ex. Y-II-34 | Acrylic resin | Y-A-3 | 100 | Achromatic (white) | 35 | 40 |
| | | Y-A-19 | 100 | Achromatic (white) | 35 | 40 |
| | | Y-A-31 | 100 | Achromatic (white) | 36 | 41 |

Ex.: Example
pbw: part by weight

Manufacture of Polycarbonate, Nylon, Polyethylene Terephthalate and Polyurethane Molded Articles

Examples Y-II-25 to Y-II-38

The test was conducted in accordance with Example Y-II-1 except that the resin to be made antibacterial was changed from polypropylene to resins which have transparency and need to have a low water content at the time of processing, such as polycarbonate, polyethylene terephthalate, nylon 6-6 and polyacetal resins, the particles Y-A-3, Y-A-19 and Y-A-31 were used as an antibacterial agent in amounts shown in Table-26, and the kneading and molding temperatures were changed to normal resin processing temperatures (290° C. for PC, PET and nylon 6-6 and 190° C. for polyacetal). The results are shown in Table-26.

Although the particles Y-A-3, Y-A-19 and Y-A-31 were used in Examples Y-II-35 to Y-II-38, no silver streak was produced on the obtained molded articles. It was confirmed that the molded articles of Examples were achromatic (white) and had excellent antibacterial properties with almost unimpaired transparency.

TABLE 26

| | | | Antibacterial properties | | | |
|---|---|---|---|---|---|---|
| | | | | | Antibacterial properties | |
| | | | Amount of | Amount of | | |
| Ex. | Resin to be made | Name of antibacterial | antibacterial agent | fluorescent brightener | *Escherichia coli* | *Staphylococcus aureus* |
| C. Ex. | antibacterial | agent particle | (pbw) | (pbw) | cfu/ml | cfu/ml |
| Ex. Y-II-35 | Polycarbonate | Y-A-3 | 0.1 | 0.0001 | 10> | 10> |
| | | Y-A-19 | 0.1 | 0.0001 | 10> | 10> |
| | | Y-A-31 | 0.1 | 0.0001 | 10> | 10> |
| EX. Y-II-36 | Polyethylene | Y-A-3 | 0.1 | 0.0001 | 10> | 10> |
| | terephthalate | Y-A-19 | 0.1 | 0.0001 | 10> | 10> |
| | | Y-A-31 | 0.1 | 0.0001 | 10> | 10> |
| Ex. Y-II-37 | Nylon 66 | Y-A-3 | 0.1 | 0.0001 | 10> | 10> |
| | | Y-A-19 | 0.1 | 0.0001 | 10> | 10> |
| | | Y-A-31 | 0.1 | 0.0001 | 10> | 10> |
| Ex. Y-II-38 | Polyacetal | Y-A-3 | 0.1 | 0.0001 | 10> | 10> |
| | | Y-A-19 | 0.1 | 0.0001 | 10> | 10> |
| | | Y-A-31 | 0.1 | 0.0001 | 10> | 10> |

| | | | Antibacterial properties | | | |
|---|---|---|---|---|---|---|
| Ex. | Resin to be made | Name of antibacterial agent | | | Pressure of extruder Kg/cm$^2$ | |
| C. Ex. | antibacterial | particle | Transparency % | Color | 2 hours | 24 hours |
| Ex. Y-II-35 | Poly- | Y-A-3 | 100 | Achromatic (white) | 50 | 55 |
| | carbonate | Y-A-19 | 100 | Achromatic (white) | 50 | 55 |
| | | Y-A-31 | 100 | Achromatic (white) | 51 | 57 |
| Ex. Y-II-36 | Polyethylene | Y-A-3 | 100 | Achromatic (white) | 40 | 45 |
| | terephthalate | Y-A-19 | 100 | Achromatic (white) | 40 | 45 |
| | | Y-A-31 | 100 | Achromatic (white) | 41 | 46 |
| Ex. Y-II-37 | Nylon 66 | Y-A-3 | 100 | Achromatic (white) | 40 | 45 |
| | | Y-A-19 | 100 | Achromatic (white) | 40 | 45 |
| | | Y-A-31 | 100 | Achromatic (white) | 40 | 46 |
| Ex. Y-II-38 | Polyacetal | Y-A-3 | 100 | Achromatic (white) | 40 | 45 |
| | | Y-A-19 | 100 | Achromatic (white) | 40 | 46 |
| | | Y-A-31 | 100 | Achromatic (white) | 40 | 46 |

Ex.: Example pbw: Part by weight

Manufacture of Films

Example Y-II-39

80 wt % of LDPE resin and 20 wt % of the antibacterial agent particles Y-A-3 were kneaded together by a pressure kneader at 120° C. for 15 minutes, and the kneaded product was granulated at 120° C. by an extrusion granulator in accordance with a hot cut method to obtain a master batch pellet having a diameter of about 3 mm.

The master batch pellet and a blend of 100 parts by weight of LDPE resin and 0.1 part by weight of the antibacterial agent particles Y-A-3 were formed into films having a thickness of 50 μm by a T die method and an inflation method.

The films were measured for antibacterial properties, transparency and whiteness by the above methods. The results are shown in Table-27.

It was confirmed that the films of Examples were achromatic (white) and had excellent antibacterial properties with unimpaired transparency. 50 μm-thick films were obtained from the particles Y-A-19 and Y-A-31 likewise.

Example Y-II-40

As to each of polypropylene, LDPE, HDPE, ionomer resin, Nylon 6/66 copolymer resin, PET resin and AS resin, a mixture pellet comprising 100 parts by weight of the resin and 0.1 part by weight of Y-A-3 particles was obtained by a double-screw kneading extruder. Mixture pellets were obtained from the particles Y-A-19 and Y-A-31 likewise.

These pellets were formed into 50 μm-thick films by the T die method.

The antibacterial properties, transparency and whiteness of each of the films were measured by the above methods. The results are shown in Table-27.

It was confirmed that the obtained films were achromatic (white) and had excellent antibacterial properties with substantially unimpaired transparency.

TABLE 27

| | | | | | Antibacterial properties | |
|---|---|---|---|---|---|---|
| Ex. C. Ex. | Resin to be made antibacterial | Name of antibacterial agent particle | Amount of antibacterial agent (pbw) | Amount of fluorescent brightener (pbw) | *Escherichia coli* cfu/ml | *Staphylococcus aureus* cfu/ml |
| Ex. Y-II-39 | LDPE | Y-A-3 | 0.1 | 0.0001 | 10> | 10> |
| | | Y-A-19 | 0.1 | 0.0001 | 10> | 10> |
| | | Y-A-31 | 0.1 | 0.0001 | 10> | 10> |
| Ex. Y-II-40 | polypropylene, LLDPE, HDPE, ionomer resin, polyurethane, nylon 6/66 copolymer resin, PET resin, AS resin | Y-A-3 | 0.1 | 0.0001 | 10> | 10> |
| | | Y-A-19 | 0.1 | 0.0001 | 10> | 10> |
| | | Y-A-31 | 0.1 | 0.0001 | 10> | 10> |

| | | | Antibacterial properties | |
|---|---|---|---|---|
| Ex. C. Ex. | Resin to be made antibacterial | Name of antibacterial agent particle | Transparency % | Color |
| Ex. Y-II-39 | LDPE | Y-A-3 | 100 | Achromatic (white) |
| | | Y-A-19 | 100 | Achromatic (white) |
| | | Y-A-31 | 100 | Achromatic (white) |
| Ex. Y-II-40 | polypropylene, LLDPE, HDPE, ionomer resin, polyurethane, nylon 6/66 copolymer resin, PET resin, AS resin | Y-A-3 | 100 | Achromatic (white) |
| | | Y-A-19 | 100 | Achromatic (white) |
| | | Y-A-31 | 100 | Achromatic (white) |

Ex.: Example
pbw: part by weight

Manufacture of Polyvinyl Chloride Molded Articles

Example Y-II-41

In Example Y-II-41, a composition comprising 100 parts by weight of polyvinyl chloride resin, 0.1 part by weight of the antibacterial agent particles Y-A-3, 1.2 parts by weight of octyltin mercapto, 0.8 part by weight of glycerin ricinoleate and 0.4 part by weight of montanic acid ester was kneaded by an open roll at 180° C. for 3 minutes and molded into a 2 mm-thick plate by a compression molding machine at 180° C. 2 mm-thick molded plates were obtained from the particles Y-A-19 and Y-A-31.

The antibacterial properties, transparency and whiteness of each of the molded plates were measured by the above methods. The results are shown in Table-28.

It was confirmed that the obtained molded plates were achromatic (white) and had excellent antibacterial properties with substantially unimpaired transparency.

TABLE 28 polyvinyl chloride

| | | | | | Antibacterial properties | | | |
|---|---|---|---|---|---|---|---|---|
| | | Name of | Amount of | Amount of | Antibacterial properties | | | |
| Ex. C. Ex. | Resin to be made antibacterial | antibacterial agent particle | antibacterial agent (pbw) | fluorescent brightener (pbw) | *Escherichia coli* cfu/ml | *Staphylococcus aureus* cfu/ml | Transparency % | Color |
| Ex. Y-II-41 | polyvinyl chloride | Y-A-3 | 0.1 | 0.0001 | 10> | 10> | 100 | Achromatic (white) |
| | | Y-A-19 | 0.1 | 0.0001 | 10> | 10> | 100 | Achromatic (white) |
| | | Y-A-31 | 0.1 | 0.0001 | 10> | 10> | 100 | Achromatic (white) |

Ex.: Example,
pbw: part by weight

Manufacture of Thermosetting Resin Molded Articles

Example Y-II-42

In Example Y-II-42, 100 parts by weight of an unsaturated polyester resin, 1 part by weight of the antibacterial agent particles Y-A-3, 3 parts by weight of a curing agent (HY951 of Ciba Specialty Chemical Co., Ltd.), 1 part by weight of stearic acid, 0.5 part by weight of an antioxidant (Irganox 1010 of Ciba Specialty Chemical Co., Ltd.) and 150 parts by weight of aluminum hydroxide for artificial marble having an average secondary particle diameter of 30 μm and a BET specific surface area of 1 m²/g were kneaded together by a kneader, and the resulting kneaded product was cured at 90° C. for 15 minutes to obtain a 2 mm-thick plate.

2 mm-thick plates were obtained from the particles Y-A-19 and Y-A-31. The antibacterial properties of the molded plates were measured by the above method. The results are shown in Table-29. It was confirmed that the obtained molded plates were achromatic (white) and had excellent antibacterial properties with substantially unimpaired transparency.

Manufacture of Fibers

Example Y-II-43

100 parts by weight of polypropylene for fibers and 2 parts by weight of the antibacterial agent particles Y-A-3 were pre-kneaded together by a double-screw kneading extruder, and the kneaded product was extruded into a 100-denier fiber from an extruder having a 300-mesh screen by a melting method. The antibacterial properties of the fiber were measured by the above method. The results are shown in Table-29.

100-denier fibers were obtained from the particles Y-A-19 and Y-A-31 likewise.

It was confirmed that the obtained fibers were achromatic (white) and had excellent antibacterial properties with substantially unimpaired transparency.

In Example Y-II-43, the spinning work was not impeded by the screen clogged up with coarse particles in the above extrusion melting method.

Manufacture of Nonwoven Fabrics

Example Y-II-44

A nonwoven fabric having a density of 0.06 g/cm³ was manufactured from the polypropylene fiber obtained in Example Y-II-43 by the papermaking web method and random web method to make the above antibacterial property test.

Nonwoven fabrics were obtained from the particles Y-A-19 and Y-A-31 likewise. The results are shown in Table-29.

It was confirmed that the obtained nonwoven fabrics were achromatic (white) and had excellent antibacterial properties with substantially unimpaired transparency.

TABLE 29

| | | | | Antibacterial properties | | | |
|---|---|---|---|---|---|---|---|
| | | Name of | Amount of | Amount of | Antibacterial properties | | |
| Ex. C. Ex. | Resin to be made antibacterial | antibacterial agent particle | antibacterial agent (pwb) | fluorescent brightener (pbw) | *Escherichia coli* cfu/ml | *Staphylococcus aureus* cfu/ml | Color |
| Ex. Y-II-42 | Unsaturated polyester resin | Y-A-3 | 1 | 0.001 | 10> | 10> | Achromatic (white) |
| | | Y-A-19 | 1 | 0.001 | 10> | 10> | Achromatic (white) |
| | | Y-A-31 | 1 | 0.001 | 10> | 10> | Achromatic (white) |
| Ex. Y-II-43 | Polypropylene fiber | Y-A-3 | 2 | 0.001 | 10> | 10> | Achromatic (white) |
| | | Y-A-19 | 2 | 0.001 | 10> | 10> | Achromatic (white) |
| | | Y-A-31 | 2 | 0.001 | 10> | 10> | Achromatic (white) |
| Ex. Y-II-44 | polypropylene nonwoven fabric | Y-A-3 | 2 | 0.001 | 10> | 10> | Achromatic (white) |
| | | Y-A-19 | 2 | 0.001 | 10> | 10> | Achromatic (white) |
| | | Y-A-31 | 2 | 0.001 | 10> | 10> | Achromatic (white) |

Ex.: Example,
pbw: part by weight

Manufacture of Rubber Molded Articles

Example Y-II-45

A composition comprising 100 parts by weight of EPDM (ethylene/propylene ratio=50/50), 0.5 part by weight of the antibacterial agent particles Y-A-3, 3 parts by weigh of dicumyl peroxide, 0.5 part by weight of poly(2,2,4-trimethyl-1,2-dihydroquinolyne), 1 part by weight of a silane coupling agent (Y-A-172 of Nippon Unicar Co., Ltd.), 0.5 part by weight of stearic acid and 1 part by weight of phosphor was kneaded by an open roll at 50° C. and cured at 160° C. for 30 minutes after 1 day to obtain a 2 mm-thick molded plate. 2 mm-thick molded plates were obtained from the particles Y-A-19 and Y-A-31 likewise.

The antibacterial properties of the molded plates were measured by the above method. The results are shown in Table-30.

It was confirmed that the obtained molded plates were achromatic (white) and had excellent antibacterial properties with substantially unimpaired transparency.

Coatings

Example Y-II-46

60 parts by weight of methyl methacrylate and 40 parts by weight of 2-ethylhexyl acrylate, 3 parts by weight of triethylene glycol dimethacrylate, 10 parts by weight of dialkyl phthalate, 0.003 part by weight of hydroquinone, 0.5 part by weight of paraffin wax having a melting point of 46° C., 0.5 part by weight of paraffin wax having a melting point of 54° C. and 0.7 part by weight of N,N-di-8-hydroxypropyl-9-P toluidine based on 100 parts by weight of the total of methyl methacrylate and 2-ethylhexyl acrylate were injected into an apparatus having a cooling unit, and 25 parts by weight of copolymer of a methyl methacrylate and n-butyl methacrylate (Tg=66° C., Mw=40,000) was added to the resulting mixture little by little under agitation, stirred at 60° C. for 2 hours and then cooled to 30° C.

A coating comprising 1 part by weight of the particles Y-A-3, 7 parts by weight of the P-400 toner of Mitsubishi Rayon Co., Ltd. as a colorant, 300 parts by weight of the KM17 of Mitsubishi Rayon Co., Ltd. as an aggregate and 2 parts by weight of diacyl peroxide as a polymerization initiator was added to the above product and left at 20° C. for 1 hour to form a coating film, and an antibacterial property test was made on the film by the above method (c) in the above paragraph (6). Coatings were obtained from the particles Y-A-19 and Y-A-31 likewise. The results are shown in Table-30. It was confirmed that the obtained coatings had excellent antibacterial properties.

Caulking Materials

Example Y-II-47

100 parts by weight of polydimethylsiloxane having a viscosity at 25° C. of 50,000 centipoise and a silanol group at a terminal and 1 part by weight of γ-aminopropyl bis(methylethylketoxyamino)methoxysilane were mixed together under vacuum for 10 minutes, 5 parts by weight of methyl tris (methylethylketoxyamino) silane was added to and mixed with the resulting mixture under vacuum for 15 minutes, and 5 parts by weight of fumed silica having a BET specific surface area of 200 $m^2/g$, 0.1 part by weight of dibutyltin laurate and 1 part by weight of the particles Y-A-3 were added to and mixed with the resulting mixture under vacuum for 10 minutes.

A 2 mm-thick test piece for the antibacterial property test was obtained by dropping this composition on a polyethylene sheet. Test pieces were obtained from the particles Y-A-19 and Y-A-31 likewise.

The antibacterial property test was made on these test pieces in accordance with the above method (e) in the paragraph (7). The results are shown in Table-30.

Ashes obtained by burning the molded articles, films, etc. of the above Examples Y-II-1 to Y-II-47 at 900° C. were dissolved in an acid to prepare solutions, and heavy metals contained in the molded articles, films, etc. of Examples were measured by atomic absorption spectrophotometry or ICP (Inductively Coupled Plasma) method. The contents of Pb, Cd, As and Ba in the resin molded articles, films and fibers of Examples Y-II-1 to Y-II-47 were all 0.1 ppm or less, the content of Fe was 5 ppm or less, and the contents of Mn, Cu, Cr and Ni were all 1 ppm or less. Therefore, it was found that the antibacterial resin composition of the present invention and products formed therefrom have high safety and excellent heat deterioration resistance.

TABLE 30

| | | | | | Antibacterial properties | |
|---|---|---|---|---|---|---|
| | | Name of | Amount of | Amount of | Antibacterial properties | |
| Ex. C. Ex. | Rubber or resin to be made antibacterial | antibacterial agent particle | antibacterial agent (pbw) | fluorescent brightener (pbw) | *Escherichia coli* cfu/ml | *Staphylococcus aureus* cfu/ml |
| Ex. Y-II-45 | Rubber; EPDM | Y-A-3 | 0.5 | 0.001 | 10> | 10> |
| | | Y-A-19 | 0.5 | 0.001 | 10> | 10> |
| | | Y-A-31 | 0.5 | 0.001 | 10> | 10> |
| Ex. Y-II-46 | Coating; acrylate-based coating | Y-A-3 | 1 | 0.001 | 10> | 10> |
| | | Y-A-19 | 1 | 0.001 | 10> | 10> |
| | | Y-A-31 | 1 | 0.001 | 10> | 10> |
| Ex. Y-II-47 | Caulking material; polydimethyl siloxane | Y-A-3 | 1 | 0.001 | 10> | 10> |
| | | Y-A-19 | 1 | 0.001 | 10> | 10> |
| | | Y-A-31 | 1 | 0.001 | 10> | 10> |

Ex.: Example
bbw: part by weight

Antifungal Agents

Examples Y-II-48 and Comparative Examples Y-II-1 and Y-II-2

As for the minimum growth prevention concentration in the standard method of the Japanese Society of Chemotherapy (2003 revised version) which differs from the present invention in that the culture medium is changed from a sensitive MHB culture medium to a potato dextrose agar medium manufactured by Nissui Pharmaceutical Co., Ltd., the antifungal performances of the antifungal agent particles of the present invention and the particles of Comparative Example were measured and expressed in ppm as the minimum growth prevention concentration. As this numerical value becomes smaller, the antifungal performance becomes higher.

The measurement results are shown in Table-31 below. The fungi used are *1: Caldosporium Caldosporides NBRC 6348 (black leather mold), *2: Colletotricum coccodes NBRC 5256 (bacterium of eggplant black dot root rot) and *3: Ustilaginoidia virens NBRC 9175 (bacterium of false smut).

TABLE 31

| Angifungal agents | | Antifungal sample Minimum growth prevention concentration ppm | | |
|---|---|---|---|---|
| | | ※1 | ※2 | ※3 |
| Example | Particle Y-A-3 | 300 or less | 30 or less | 15 or less |
| | Particle Y-A-5 | 300 or less | 30 or less | 15 or less |
| | Particle Y-A-8 | 300 or less | 30 or less | 15 or less |
| | Particle Y-A-10 | 300 or less | 30 or less | 15 or less |
| | Particle Y-A-11 | 300 or less | 30 or less | 15 or less |
| | Particle Y-A-18 | 300 or less | 30 or less | 15 or less |
| | Particle Y-A-19 | 300 or less | 30 or less | 15 or less |
| | Particle Y-A-31 | 300 or less | 30 or less | 15 or less |
| | Particle Y-A-1-2 | 300 or less | 30 or less | 15 or less |
| Comparative Example Y-II-1 Particles R1 (silver supporting zirconium phosphate) Average secondary particle diameter; 1 μm BET specific surface area; 4 m²/g Content of Ag; 3% ※The particles R1 were also used in the following experiments. | | 6400 | 3000 | 20 |

TABLE 31-continued

| Angifungal agents | Antifungal sample Minimum growth prevention concentration ppm | | |
|---|---|---|---|
| | ※1 | ※2 | ※3 |
| Comparative Example Y-II-2 Bordeaux scatter powders (commercially available Bordeaux scatter powder containing 11.1% of copper sulfate and 6.0% of copper) | 6400< | 6400< | 800 |

It was found that the antifungal agents of the present invention have much higher excellent antifungal performance than that of the antifungal agents in Comparative Examples.

Cosmetics

Example Y-II-49

Water-in-oil type creamy emulsion cosmetics comprising the components of Example and Comparative Examples shown in the table below were prepared. A mixture of oily materials denoted by 1 to 5, surfactants denoted by 6 and 7 and an antibacterial agent denoted by 10 was designated as A, a mixture of purified water denoted by 8 and a humectant denoted by 9 was designated as B, the mixtures A and B were heated at 70° C., the mixture B was poured into the mixture A under agitation, and the resulting product was emulsified and then cooled to room temperature to obtain water-in-oil type creamy emulsion cosmetics.

An antibacterial property test was carried out 30 days after emulsification by using *E. coli* NBRC 3972 in accordance with the method (c) in the above paragraph (7). Further, 1 g of each of the creams of Example and Comparative Example was applied to the armpit of a person always giving off a bad smell from under his/her arms, and 10 people were asked to check whether the person was still giving off a bad smell or not after 8 hours. The measurement results are shown in Table-32 below.

TABLE 32

| | Component | | | |
|---|---|---|---|---|
| No. | Substance | role | Example Y-II-49 | C. Ex. Y-II-3 |
| 1 | Dodecyl isostearate | oil | 25 | 25 |
| 2 | Squalane | oil | 15 | 15 |
| 3 | Bees wax | oil | 8 | 8 |
| 4 | Cholesteryl hydroxystearate | oil | 0.2 | 0.2 |
| 5 | Shea butter | oil | 5 | 5 |
| 6 | decaglyceryl pentaoleate | surfactant | 3 | 3 |
| 7 | decaglyceryl diisostearate | surfactant | 1 | 1 |
| 8 | purified water | matrix | balance | balance |
| 9 | glycerin | humectant | 3 | 3 |

TABLE 32-continued

| No. | Substance | | role | Example Y-II-49 | | | | | | | | C. Ex. Y-II-3 | |
|---|---|---|---|---|---|---|---|---|---|---|---|---|---|
| 10 | Products of Present Invention | Particle Y-A-3 | antibacterial agent | 0.5 | 0 | 0 | 0 | 0 | 0 | 0 | 0 | 0 | 0 |
| | | Particle Y-A-5 | antibacterial agent | 0 | 0.5 | 0 | 0 | 0 | 0 | 0 | 0 | 0 | 0 |
| | | Particle Y-A-8 | antibacterial agent | 0 | 0 | 0.5 | 0 | 0 | 0 | 0 | 0 | 0 | 0 |
| | | Particle Y-A-10 | antibacterial agent | 0 | 0 | 0 | 0.5 | 0 | 0 | 0 | 0 | 0 | 0 |
| | | Particle Y-A-11 | antibacterial agent | 0 | 0 | 0 | 0 | 0.5 | 0 | 0 | 0 | 0 | 0 |
| | | Particle Y-A-18 | antibacterial agent | 0 | 0 | 0 | 0 | 0 | 0.5 | 0 | 0 | 0 | 0 |
| | | Particle Y-A-19 | antibacterial agent | 0 | 0 | 0 | 0 | 0 | 0 | 0.1 | 0 | 0 | 0 |
| | | Particle Y-A-31 | antibacterial agent | 0 | 0 | 0 | 0 | 0 | 0 | 0 | 1 | 0 | 0 |
| | | Particle Y-A-1-2 | antibacterial agent | 0 | 0 | 0 | 0 | 0 | 0 | 0 | 1 | 0 | 0 |
| | Particle R1 | | antibacterial agent | 0 | 0 | 0 | 0 | 0 | 0 | 0 | 0 | 0.5 | 0 |
| *Escherichia coli* NBRC3972 cfu/ml | | | | 10> | 10> | 10> | 10> | 10> | 10> | 10> | 10> | $1 \times 10^6$ | $2 \times 10^6$ |
| number of people who smell a bad smell | | | | 0/10 | 0/10 | 0/10 | 0/10 | 0/10 | 0/10 | 0/10 | 0/10 | 10/10 | 10/10 |

C. Ex.: Comparative Example

It was confirmed that the cosmetics of Examples had the excellent antibacterial properties and suppressive effects for bad smell. On the other hand, the cosmetics of Comparative Examples had no antibacterial properties nor suppressive effects for bad smell at all, though the cosmetics of Comparative Examples differ from those of Examples only in that the particles R1 were in place of the antibacterial agent of the Examples or no antibacterial agent was added in Comparative Examples.

Antibacterial Deodorizing Sprays

Example Y-II-50 and Comparative Examples Y-II-4 and Y-5-13

2.3 parts by weight of dipropylene glycol was injected into a container heated at 70° C., and further 2.5 parts by weight of lauric acid, 1 part by weight of myristic acid and 3.2 parts by weight of triethanolamine were added to the container to prepare a solution.

This solution was added to 90 parts by weight of ion exchange water heated at 70° C. little by little to be emulsified so as to prepare a foam matrix solution which was then cooled to 25° C.

1 part by weight of the antibacterial agent particles of the present invention was added to and mixed with the foam matrix solution under agitation to prepare an antibacterial deodorizing foam aerosol composition.

180 g of this composition and 20 g of an injection agent (LPG 0.34 MPa) were charged into a spray tin can to prepare an antibacterial deodorizing foam aerosol spray.

After a person always giving off a bad smell from under his/her arms took plenty of exercise, his/her sweat was collected with a cotton handkerchief measuring 15 cm×15 cm to be increased by weighing 0.5 g and 5 g, respectively. After 1 g of the antibacterial deodorizing foam aerosol spray was applied to the front and rear sides of the handkerchief which was then left in a thermostat tank at 30° C. for 10 days, people were asked to smell the handkerchief. The measurement results are shown in Table-33 below.

TABLE 33

| An increase in weight of handkerchief, antibacterial agent | | odor test people who smell a bad smell | |
|---|---|---|---|
| An increase in weight of handkerchief | | 0.5 g | 5 g |
| Example X-II-50 | Particle Y-A-3 1 pbw | 0/10 | 0/10 |
| | Particle Y-A-5 1 pbw | 0/10 | 0/10 |

TABLE 33-continued

| An increase in weight of handkerchief, antibacterial agent | | odor test people who smell a bad smell | |
|---|---|---|---|
| | Particle Y-A-8 1 pbw | 0/10 | 0/10 |
| | Particle Y-A-10 1 pbw | 0/10 | 0/10 |
| | Particle Y-A-11 1 pbw | 0/10 | 0/10 |
| | Particle Y-A-18 1 pbw | 0/10 | 0/10 |
| | Particle Y-A-19 1 pbw | 0/10 | 0/10 |
| | Particle Y-A-31 1 pbw | 0/10 | 0/10 |
| | Particle Y-A-1-2 1 pbw | 0/10 | 0/10 |
| Comparative Example Y-II-4 particles R1 (silver supporting zirconium phosphate) 1 pbw | | 5/10 | 10/10 |
| Comparative Example Y-II-5 (without an antibacterial agent) | | 10/10 | 10/10 | pbw: part by weight

It was found that the antibacterial agents of the present invention had much higher performance for preventing bad smell than those of the Comparative Examples.

Antibacterial Paper

Example Y-II-51 and Comparative Examples Y-II-6 and Y-II-7

1% of the antibacterial agent of the present invention, 5% of starch (dry paper reinforcing agent), 5% of urea-formaldehyde resin (wet paper reinforcing agent), 2% of titanium dioxide (inorganic filler) and 5% of a polyamide resin-based ink (adhesive binder) were mixed into 82% of bleached chemical pump to make 0.1 mm-thick paper by a paper machine. A 5 cm×5 cm piece was cut out from this paper to carry out an antibacterial property test on the piece in accordance with the above method (a) in the paragraph (7). The results are shown in Table-34 below.

TABLE 34

| Antibacterial agent | | Antibacterial test *Escherichia coli* number of colony cfu/ml *E.coli* NBRC 3972 |
|---|---|---|
| Example X-II-51 | Particle Y-A-3 5% | 10> |
| | Particle Y-A-5 5% | 10> |
| | Particle Y-A-8 5% | 10> |
| | Particle Y-A-10 5% | 10> |
| | Particle Y-A-11 5% | 10> |
| | Particle Y-A-18 5% | 10> |
| | Particle Y-A-19 5% | 10> |

TABLE 34-continued

| Antibacterial agent | Antibacterial test Escherichia coli number of colony cfu/ml E.coli NBRC 3972 |
|---|---|
| Particle Y-A-31 5% | 10> |
| Particle Y-A-1-2 5% | 10> |
| Comparative Example Y-II-6 particles R1 (silver supporting zirconium phosphate) 5% | $1 \times 10^5$ |
| Comparative Example Y-II-7 (without an antibacterial agent) 0% | $2 \times 10^6$ |

It was found that the antibacterial agents of the present invention had much higher antibacterial performance than those of the comparative Examples.

Agricultural Chemicals (Antifungal Agents)

Example Y-II-52 and Comparative Examples Y-II-8 and Y-II-9

In Example, 10 parts by weight of the particles of the present invention, 30 parts by weight of surface modifying precipitated calcium carbonate as a silane coupling agent (inorganic powder), 5 parts by weight of polyoxyethylene alkyl allyl ether (surfactant), 10 parts by weight of ethylene glycol (surfactant), 0.2 part by weight of xanthane rubber (emulsification stabilizer) and 44.8 parts by weight of water were uniformly mixed together by a homomixer, and the resulting mixture was uniformly wet ground by a ball mill to obtain an aqueous suspended agricultural chemical composition. This was diluted with water to 1/100 and injected into a commercially available plastic spray.

In Comparative Examples, the procedure of Example was repeated except that the following particles or Bordeaux scatter powder was used in place of the particles of Example.

Meanwhile, an eggplant and a rice plant grown as large as about 20 cm were prepared.

1 g of a suspension of Colletotricum coccodes NBRC 5256 (bacterium of eggplant black dot root rot) having $1 \times 10^6$ cfu/ml was sprayed over the leaf, stem and base of the eggplant, 1 g of the above aqueous suspended agricultural chemical composition diluted to 1/100 was sprayed after one day, and an outbreak of black dot root rot in the eggplant was checked after 30 days. The test on the eggplant was carried out by putting soil into a pot having a diameter of 33 cm and a depth of 30 cm to a height of 27 cm.

1 g of a suspension of Ustilaginoidia virens NBRC 9175 (bacterium of false smut) having $1 \times 10^6$ cfu/ml was sprayed over the leaf, stem and base of the rice plant, 1 g of the aqueous suspended agricultural chemical composition diluted to 1/100 was sprayed after 1 day, and an outbreak of false smut in the rice plant was checked after 30 days. The test on the rice plant was carried out by putting soil into a pot having a diameter of 33 cm and a depth of 30 cm to a height of 27 cm under the condition that water barely covered the surface of the soil but a sufficient amount of water was existent in the soil. The measurement results are shown in Table-35 below.

TABLE 35

| Antifungal agents | | Plant | |
|---|---|---|---|
| | | eggplant black dot root rot | rice plant false smut |
| Example Antifungal agents used in present invention | Particle Y-A-3 | Not observed Grown well | Not observed Grown well |
| | Particle Y-A-5 | Not observed Grown well | Not observed Grown well |
| | Particle Y-A-8 | Not observed Grown well | Not observed Grown well |
| | Particle Y-A-10 | Not observed Grown well | Not observed Grown well |
| | Particle Y-A-11 | Not observed Grown well | Not observed Grown well |
| | Particle Y-A-18 | Not observed Grown well | Not observed Grown well |
| | Particle Y-A-19 | Not observed Grown well | Not observed Grown well |
| | Particle Y-A-31 | Not observed Grown well | Not observed Grown well |
| | Particle Y-A-1-2 | Not observed Grown well | Not observed Grown well |
| Comparative Example particles R1 (silver supporting zirconium phosphate) | | Observed in the whole root and withered | Observed in the whole root and withered |
| Comparative Example (Bordeaux scatter powder) (commercially available Bordeaux scatter powder containing 11.1% of copper sulfate and 6.0% of copper) | | Observed in the whole root and withered | Observed in the whole root and withered |

It was found that the agricultural chemicals in the present invention showed the much higher agricultural performance than those of the comparative Examples.

The invention claimed is:

1. An antibacterial agent composed of silver-containing aluminum sulfate hydroxide particles represented by the following formula (X-I):

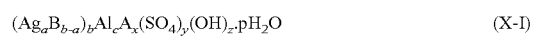

$$(Ag_aB_{b-a})_bAl_cA_x(SO_4)_y(OH)_z \cdot pH_2O \quad (X\text{-}I)$$

wherein a, b, c, x, y, z and p satisfy $0.001 \leq a \leq 0.3$, $0.7 \leq b \leq 1.35$, $2.7 < c < 3.3$, $0.001 \leq x \leq 0.5$, $1.7 < y < 2.5$, $4 < z < 7$ and $0 \leq p \leq 5$, respectively, B is at least one monovalent cation selected from the group consisting of $Na^+$, $NH_4^+$, $K^+$ and $H_3O^+$, the total value (1b+3c) obtained by multiplying the valences by the numbers of mols of the cations satisfies $8 < (1b+3c) < 12$, and A is an organic acid anion.

2. The antibacterial agent according to claim 1 which has an average secondary particle diameter measured by a laser diffraction scattering method of 0.1 to 12 μm.

3. The antibacterial agent according to claim 1 which has a BET specific surface area of 0.1 to 250 m²/g.

4. The antibacterial agent according to claim 1 which is surface treated with at least one member selected from the group consisting of a higher fatty acid, silane-based coupling agent, titanate-based coupling agent, aluminate-based coupling agent, alcohol phosphate and surfactant.

5. A resin composition having antibacterial properties which comprises 0.001 to 300 parts by weight of the antibacterial agent of claim 1 and 100 parts by weight of a resin.

6. An antibacterial resin composition which comprises 0.001 to 2 parts by weight of the antibacterial agent of claim 1 and 100 parts by weight of a resin, wherein the antibacterial resin composition has transparency.

7. An antibacterial resin molded article formed from the resin composition of claim 5.

8. An antibacterial film formed from the resin composition of claim 5.

9. An antibacterial fiber formed from the resin composition of claim 5.

10. An antibacterial nonwoven fabric formed from the resin composition of claim 5.

11. An antibacterial coating formed from the resin composition of claim 5.

12. An antibacterial caulking material formed from the resin composition of claim 5.

13. The antibacterial resin product according to claim 5 which further comprises 0.000001 to 0.1 part by weight of a fluorescent brightener based on 100 parts by weight of the resin, to improve whiteness.

14. An antifungal agent comprising the antibacterial agent composed of silver-containing aluminum sulfate hydroxide particles represented by the formula (X-I) of claim 1.

15. A cosmetic containing the antibacterial agent composed of silver-containing aluminum sulfate hydroxide particles represented by the formula (X-I) of claim 1.

16. Antibacterial paper containing the antibacterial agent composed of silver-containing aluminum sulfate hydroxide particles represented by the formula (X-I) of claim 1.

17. An antibacterial deodorizing spray containing the antibacterial agent composed of silver-containing aluminum sulfate hydroxide particles represented by the formula (X-I) of claim 1.

18. An agricultural chemical containing the antibacterial agent composed of silver-containing aluminum sulfate hydroxide particles represented by the formula (X-I) of claim 1.

19. The antibacterial agent according to claim 1, wherein the organic acid anion A in the formula (X-I) is at least one selected from anions based on an organic carboxylic acid and an organic oxycarboxylic acid.

20. The antibacterial agent according to claim 1, wherein the organic acid anion A in the formula (X-I) is at least one selected from anions based on an organic carboxylic acid and organic oxycarboxylic acid having 1 to 15 carbon atoms.

21. The antibacterial agent according to claim 1, wherein B in the formula (X-I) is at least one monovalent cation selected from the group consisting of $Na^+$, $H_3O^+$ and $NH_4^+$.

22. The antibacterial agent according to claim 1 which is prepared by replacing ½ or less of the "c" mols of aluminum in the formula (X-I) with the total number of mols of $Zn^{2+}$ and/or $Ti^{4+}$.

23. The antibacterial agent according to claim 1, wherein part of $SO_4^{2-}$ of $(SO_4)_y$ in the formula (X-I) is replaced with at least one other inorganic acid ion selected from the group consisting of $PO_4^{3-}$, $CO_3^{2-}$, $NO^{3-}$, $SiO_4^{4-}$ and $BO_3^{3-}$.

24. The antibacterial agent according to claim 1, wherein the particles are represented by the formula (X-I) and have a sharpness (Dr) of the particle size distribution
defined as $Dr=D_{75}/D_{25}$ ($D_{25}$ is the particle diameter of the 25% value and $D_{75}$ is the particle diameter of the 75% value of a volume-based cumulative particle size distribution curve measured by a laser diffraction scattering method) of 1.0 to 1.8.

25. The antibacterial agent according to claim 1, wherein the particles are represented by the formula (X-I) and spherical, disk-like ("go" stone-like), paired (hamburger-like), rice grain-like, rectangular parallelepiped, hexagonal plate-like, columnar (cask-like) or octahedral when observed from a SEM photomicrograph.

26. The antibacterial agent according to claim 1, wherein the particles have an average secondary particle diameter measured by the laser diffraction scattering method of 0.1 to 5 μm.

27. The antibacterial agent according to claim 1, wherein the particles have a BET specific surface area of 1 to 100 $m^2/g$.

28. The antibacterial agent according to claim 1, wherein a, b, c, x, y, z and p in the formula (X-I) satisfy $0.001 \leq a < 0.3$, $0.9 \leq b \leq 1.2$, $2.7 < c < 3.3$, $0.001 \leq x \leq 0.2$, $1.7 < y < 2.3$, $5 < z < 7$ and $0 \leq p < 3$, respectively, B is at least one monovalent cation selected from the group consisting of $Na^+$, $NH_4^+$ and $H3O^+$, and the total value (1+3c) obtained by multiplying the valences by the numbers of tools of the cations satisfies 9 (1b+3c) 11.

29. The antibacterial agent according to claim 1, wherein A in the formula (X-I) is at least one organic acid anion selected from the group consisting of oxalic acid ion, citric acid ion, malic acid ion, tartaric acid ion, glyceric acid ion, gallic acid ion and lactic acid ion.

30. A method of manufacturing the silver- and organic acid anion- containing aluminum sulfate hydroxide particle antibacterial agent of claim 1, comprising the steps of:
adding an aqueous solution of an alkali having a monovalent cation and an organic acid to a mixed aqueous solution of aluminum sulfate and a sulfate and/or a nitrate having a monovalent cation to carrying out a thermal reaction so as to form organic acid anion- containing aluminum sulfate hydroxide particles; and
bringing the obtained particles into contact with an aqueous solution containing silver under agitation to ion exchange some of the cations of the particles with silver.

* * * * *